US010507162B2

(12) United States Patent
Kang et al.

(10) Patent No.: US 10,507,162 B2
(45) Date of Patent: Dec. 17, 2019

(54) MASSAGE BATHING MAINTENANCE SYSTEM AND MAINTENANCE METHOD OF THE SAME

(71) Applicant: Dartpoint Tech. Co., Ltd., Taipei (TW)

(72) Inventors: Chi-Lin Kang, New Taipei (TW); Chung-Hsin Hsieh, Taipei (TW); Chao-Yuan Huang, Taipei (TW)

(73) Assignee: DARTPOINT TECH. CO., LTD., Taipei (TW)

( * ) Notice: Subject to any disclaimer, the term of this patent is extended or adjusted under 35 U.S.C. 154(b) by 914 days.

(21) Appl. No.: 14/721,022

(22) Filed: May 26, 2015

(65) Prior Publication Data

US 2015/0335524 A1 Nov. 26, 2015

Related U.S. Application Data

(60) Provisional application No. 62/002,946, filed on May 26, 2014.

(30) Foreign Application Priority Data

Apr. 17, 2015 (TW) ............................ 104112392 A

(51) Int. Cl.
*A61H 33/00* (2006.01)
*G01M 99/00* (2011.01)
*G16H 40/40* (2018.01)

(52) U.S. Cl.
CPC ........... *A61H 33/005* (2013.01); *G16H 40/40* (2018.01); *A61H 2201/5043* (2013.01); *A61H 2201/5097* (2013.01)

(58) Field of Classification Search
None
See application file for complete search history.

(56) References Cited

U.S. PATENT DOCUMENTS 8,280,535 B2 * 10/2012 Hsieh .................. G05B 19/042 307/11
2003/0149546 A1 8/2003 Kim
(Continued)

FOREIGN PATENT DOCUMENTS

| | | |
|---|---|---|
| CN | 102130438 | 7/2011 |
| TW | 236137 | 12/1994 |
| TW | 407064 | 7/2011 |

*Primary Examiner* — Robert K Carpenter
(74) *Attorney, Agent, or Firm* — Mark M. Friedman

(57) ABSTRACT

A massage bathing maintenance system suitable for a massage bathing equipment is provided. The system comprises at least one attached device, at least one slave control device, a master control device, and an analyzing unit. The at least one attached device is configured to actuate with regard to the massage bathing equipment. The at least one slave control device comprises a control unit configured to generate and transmit at least one actuating message according to at least one actuating-status of the at least one attached device. The master control device comprise a log-collecting unit configured to record the at least one actuating message of the at least one slave control device into a logs table. The analyzing unit is configured to analyze the at least one actuating message of the logs table so as to determine whether the actuation of at least one attached device is abnormal.

16 Claims, 46 Drawing Sheets

(56) References Cited

U.S. PATENT DOCUMENTS

| | | | | |
|---|---|---|---|---|
| 2010/0168928 | A1 | 7/2010 | Hsieh | |
| 2010/0219962 | A1* | 9/2010 | Brochu | G05B 23/0235 340/635 |
| 2011/0046796 | A1 | 2/2011 | Brochu et al. | |

* cited by examiner

MASSAGE BATHING MAINTENANCE SYSTEM AND MAINTENANCE METHOD OF THE SAME

CROSS-REFERENCE TO RELATED APPLICATIONS

This application claims the benefit of U.S. Provisional Application No. 62/002,946, filed on May 26, 2014, which is hereby incorporated by reference for all purposes as if fully set forth herein.

FIELD OF THE INVENTION

The present invention relates to a massage bathing maintenance system and maintenance method of the same, and in particular is related to the technical field of massage bathing equipment such as a massage bathtub/hot tub, a SPA pool, or a swimming pool.

BACKGROUND OF THE INVENTION

In the prior art, when a massage bathing equipment or peripheral devices relative to the massage bathing equipment malfunctions, a technical staff is unable to prepare relative spare parts before performing on the spot tests, which will prolong a repair time. Of course, the technical staff can prepare ail the spare parts; however, this is not economical. So, requiring the technical staff to derive most of the malfunctioning issues beforehand in order to prepare the possible spare parts is a drawback which needs to be solved.

Hence, it is essential to provide a massage bathing maintenance system and a maintenance method to solve the drawback as mentioned above.

SUMMARY OF THE INVENTION

In order to solve, the aforementioned drawbacks of the prior art, an objective of the present invention is to provide a massage bathing maintenance system, which is applied for a massage bathing equipment, and is configured to rapidly derive an operational status of the whole system in order to provide quick and suitable maintenance. The massage bathing maintenance system comprises at least one attached device, at least one slave control device, a master control device, and an analyzing unit. The at least one attached device is provided for relatively actuating to the massage bathing equipment. The at least one slave control device comprises a control unit configured to generate and transmit at least one actuating message according to at least one actuating-status of the at least one attached device. The master control device is configured to control the at least one slave control device through a master-slave connection therebetween and to receive the at least one actuating message, and the master control device comprises a log-collecting unit configured to record the at least one actuating message of the at least one slave control device into a logs table. The analyzing unit is configured to analyze the at least one actuating message of the logs table so as to determine whether the actuation of at least one attached device being abnormal.

In a preferred embodiment, the at least one slave control device is a massage bathing control unit and/or the analyzing unit is disposed inside the master control device.

In a preferred embodiment, the at least one attached device is disposed inside the at least one slave control device.

In a preferred embodiment, the master control device further comprises a memory unit for storing the logs table, the logs table is further configured to locate communication records between the master control device and the at least one slave control device.

In a preferred embodiment, the analyzing unit looks up a built-in table according to the at least one actuating message, to determine whether an abnormal situation and/or aging situation has occurred.

In a preferred embodiment, the actuating message is an abnormal code, a physical value, or a chemical value.

In a preferred embodiment, the physical value is a voltage value or a current value.

In a preferred embodiment, the control unit of the at least one slave control device generates the at least one actuating message according to at least one preset self-detecting operation process and transmits the at least one actuating message to the master control device or other slave control device.

In a preferred embodiment, the master control device generates at least one controlling message to the at least one slave control device, for requesting the control unit of the at least one slave control device to generate and feed back the at least one actuating message.

In a preferred embodiment, the master control device generates an informing message according to a determined result with respect to the at least one actuating message.

In a preferred embodiment, the system further comprises an operation panel unit, which is electrically connected with the master control device, and the operation panel unit comprises a display screen to show the informing message.

In a preferred embodiment, the system further comprises at least one wireless communication transceiver, which is respectively connected with the master control device and the at least one slave control device, to proceed a remote trouble shooting maintenance.

In a preferred embodiment, the system further comprises at least one wireless communication transceiver and a cloud server, the cloud server comprises at least one cloud database, a certificate managing unit, a device-managing unit, an instant-message transceiving management unit, and a remote detecting and maintaining management unit, the remote detecting and maintaining management unit comprises the analyzing unit, the at least one cloud database is configured to store a corresponding serial number of the massage bathing equipment, and the at least one wireless communication transceiver is configured to be connected with the cloud server, for transmitting the logs table via the master control device to the at least one cloud database of the cloud server, and for storing the logs table in the at least one cloud database of the cloud server.

In a preferred embodiment, the cloud server sends a request to the master control device to collect the at least one actuating message from the at least one slave control device and record into the logs table, then stores the logs table in the master control device and/or transmits the logs table from the master control device to the at least one cloud database of the cloud server, for storage of maintenance usage.

In a preferred embodiment, the cloud server makes the remote detecting and maintaining management unit to proceed at least one preset remote detecting and maintaining management process according to a determined result, made by the analyzing unit, with respect to the at least one actuating message of the logs table.

In a preferred embodiment, the master control device generates the at least one controlling message to the at least one slave control device according to the at least one preset remote detecting and maintaining management process, and the master control device requests the control unit of the at least one slave control device to proceed warm reboots and a detection, so that the at least one slave control device generate the at least one actuating message, including the detection result.

In a preferred embodiment, the master control device proceeds at least one maintaining operation according to the at least one preset remote detecting and maintaining management process, and after the maintaining operation is processed, the master control device requests the control unit of the at least one slave control device to proceed the detection so that the at least one slave control device generates the at least one actuating message including the detection result, wherein the at least one maintaining operation comprises one or a combination of several of wrong setup corrections, cold reboots, source code reinstallations, and software version updates.

In order to solve the aforementioned drawbacks, another objective of the present invention is to provide a massage bathing maintenance system, which is applied for a massage bathing equipment and comprises at least one attached device, at least one slave control device, a master control device, and an analyzing unit.

The at least one attached device is provided for relatively actuating to the massage bathing equipment. The at least one slave control device comprises a control unit and a detection-feedback device, the control unit is configured to generate and transmit at least one actuating message according to at least one actuating-status of the at least one attached device. The master control device is configured to control the at least one slave control device through a master-slave connection therebetween and to receive the at least one actuating message, and the master control device comprises a log-collecting unit configured to record the at least one actuating message of the at least one slave control device into a logs table. The analyzing unit is configured to analyze the at least one actuating message of the logs table so as to determine whether the actuation of at least one attached device being abnormal. The control unit controls the detection-feedback device to detect the at least one attached device, generates the at least one actuating message including the detection result and transmits the at least one actuating message to the master control device.

In a preferred embodiment, the at least one slave control device is a massage bathing control unit.

In a preferred embodiment, the at least one attached device comprises one or a combination of several of a blower, a motor, an air valve, a sensor, a pump, an ozone generator, a light controlling device, and a heater.

In a preferred embodiment, the master control device request the at least one slave control device transmits the at least one actuating message.

In a preferred embodiment, the at least one attached device is disposed inside the at least one slave control device.

In a preferred embodiment, the system further comprises at least one wireless communication transceiver and a cloud server, the cloud server comprises at least one cloud database, a certificate managing unit, a device-managing unit, an instant-message transceiving management unit, and a remote detecting and maintaining management unit, the remote detecting and maintaining management unit comprises the analyzing unit, the at least one cloud database is configured to store a corresponding serial number of the massage bathing equipment, and the at least one wireless communication transceiver is configured to be connected with the cloud server, for transmitting the logs table via the master control device to the at least one cloud database of the cloud server, and for storing the logs table in the at least one cloud database of the cloud server.

In a preferred embodiment, the remote detecting and maintaining management unit of the cloud server sends a request to the master control device to request the at least one slave control device to feed the at least one actuating message back to the cloud server.

In a preferred embodiment, the cloud server makes the remote detecting and maintaining management unit to proceed at least one preset remote detecting and maintaining management process according to a determined result, made by the analyzing unit, with respect to the at least one actuating message of the logs table.

In a preferred embodiment, the master control device generates the at least one controlling message to the at least one slave control device according to the preset remote detecting and maintaining management process, and the master control device requests the control unit of the at least one slave control device to proceed warm reboots and a detection, so that the at least one slave control device generate the at least one actuating message including the detection result.

In a preferred embodiment, the master control device proceeds at least one maintaining operation according to the at least one preset remote detecting and maintaining management process. After the maintaining operation is proceeded, the master control device requests the control unit of the at least one slave control device to proceed the detection so that the at least one slave control device generates the at least one actuating message including the detection result, wherein the at least one maintaining operation comprises one or a combination of several of wrong setup corrections, cold reboots, source code reinstallations, and software version updates.

In a preferred embodiment, the master control device proceeds the at least one maintaining operation via a maintain interface.

In a preferred embodiment, the maintain interface is one or both of JTAG (Joint Test Action Group) and RESET.

In a preferred embodiment, the detection-feedback device comprises at least one switch unit and at least one sensing unit, the at least one switching unit is controlled by the control unit to turn on or off a power source supplied to the at least one attached device, the at least one sensing unit detects a specific physical value between the at least one switch unit and the at least one attached device, and transmits the specific physical value to the control unit, and the control unit treats the physical value as the detection result to generate the at least one actuating message according to the detection result and provides the at least one actuating message to the master control device.

In a preferred embodiment, the detection-feedback device comprises at least one switch unit and at least one sensing unit, the at least one switching unit is controlled by the control unit to turn on or off a power source supplied to the at least one attached device, the at least one sensing unit detects a specific physical value of the at least one attached device, and transmits the specific physical value to the control unit, and the control unit treats the physical value as the detection result to generate the at least one actuating message according to the detection result and provides the at least one actuating message to the master control device.

In a preferred embodiment, the detection-feedback device comprises at least one switch unit and at least one sensing unit, the at least one switching unit is controlled by the control unit to turn on or off a power source supplied to the at least one attached device, the at least one sensing unit detects a specific physical value between the power source supplied to the at least one attached device and the at least one attached device, and transmits the specific physical value to the control unit, and the control unit treats the physical value as the detection result to generate the at least one actuating message according to the detection result and provides the at least one actuating message to the master control device.

In a preferred embodiment, the at least one switch unit is relay, the physical value is a current value or a logical determined value.

In a preferred embodiment, the detection-feedback device further comprises a temperature-measurement-offset confirming device, which is electrically connected with the control unit, and is configured to detect a temperature status of a temperature meter to be the detection result, and the control unit generates the at least one actuating message according to the detection result and transmits the at least one actuating message to the master control device.

In a preferred embodiment, the temperature-measurement-offset confirming device comprises a temperature sensor and a voltage detection unit, both of which detect data for determining whether the temperature sensor is abnormal.

In a preferred embodiment, the analyzing unit looks up a built-in table according to the at least one actuating message, to determine whether an abnormal situation and/or aging situation has occurred.

In order to solve the aforementioned drawbacks, another objective of the present invention is to provide a massage bathing maintenance method which comprising:

First, at least one slave control device generating at least one actuating message according to an actuation of at least one attached device relatively to the massage bathing equipment, and storing the at least one actuating message in at least one logs table built in a master control device, wherein the master control device is connected with the at least one slave device through a master-slave connection therebetween. Then, looking up the at least one actuating message of the at least one attached device from the logs table which is stored in the master control device. Then, analyzing the at least one actuating message of the at least one attached device of the logs table by an analyzing unit to determine whether an abnormal situation and/or aging situation has occurred on the at least one attached device and to transmit an informing message. Then, confirming by the master control device whether the abnormal situation is eliminated.

In a preferred embodiment, first, deriving a serial number of the massage bathing equipment from at least one cloud database of a cloud server. Then, determining whether the serial number is valid by the cloud server. Then, establishing an internet connection between the cloud server and the master control device through at least one wireless communication transceiver.

In a preferred embodiment, first, establishing the master-slave connection between the at least one slave control device and the master control device.

In a preferred embodiment, while the cloud server confirms the serial number is invalid or the internet connection between the cloud server and the master control device is unable to be established, then the cloud server transmitting the informing message to inform for artificial site maintenance.

In a preferred embodiment, while the internet connection between the cloud server and the master control device is established, then, looking up the at least one actuating message of the at least one attached device in the logs table through the master control device by the cloud server. Then, the analyzing unit of the cloud server determining whether an abnormal situation occurs on the at least one attached device according to the at least one actuating message. While confirming an abnormal situation has occurred on the at least one attached device, proceeding a preset remote detecting and maintaining management process to the at least one slave control device by the cloud server.

In a preferred embodiment, first, determining whether a setup is wrong on the at least one slave control device, wherein while confirming the setup is wrong on the at least one slave control device, correcting the setup of the at least one slave control device according to the setup of the cloud server. Then, generating and transmitting an actuating message after the correction to the cloud server. Then, determining whether the at least one slave control device works normally. Then, determining whether there is another abnormal situation. Finally, the method is ended.

In a preferred embodiment, while the at least one slave control works abnormally, the method further comprises:

First, the cloud server transmitting the informing message to inform for artificial site maintaining. Finally, ending the method.

In a preferred embodiment, while determining the at least one slave control device works normally or another abnormal situations have occurred, the method further comprises:

First, determining whether the peripheral-communication is abnormal. Then, controlling the at least one slave control device to proceed warm reboots. Then, generating the at least one actuating message. Then, confirming whether the at least one slave control device works normally. Then, confirming whether there is no other abnormal situation.

In a preferred embodiment, while confirming the at least one slave control device works abnormally, the method further comprises:

First, controlling the at least one slave control device to proceed cold reboots. Then, generating the at least one actuating message. Then, confirming whether the at least one slave control device works normally. Then, determining whether there is another abnormal situation.

In a preferred embodiment, while confirming there is other abnormal situations have occurred or the peripheral-communication is normal, the method further comprises:

First, reinstalling the at least one slave control device with a current software version. Then, confirming whether the at least one slave control device works normally.

In a preferred embodiment, while the at least one slave control device works abnormally, the method further comprising:

First, confirming whether the software version of the at least one slave control device is older. While the software version is older, then, updating the software version of the at least one slave control device. Then, generating the at least one actuating message and storing the at least one actuating message in the logs table. Then, confirming whether the at least one slave control device works normally.

In a preferred embodiment, while confirming the software version is updated or the at least one slave control device works abnormally, the method further comprises the step of:

Transmitting by the cloud server the informing message to inform for artificial site maintenance, and finally ending the method.

In order to solve the aforementioned drawbacks, another objective of the present invention is to provide a self-detection method of the massage bathing maintenance system, the massage bathing maintenance system comprises an operating panel unit, a master control device, at least one attached device, an analyzing unit, and a massage bathing control unit. The operating panel unit is electrically connected with the master control device, and comprises a display screen to show an actuating status of the at least one attached device with regard to a massage bathing equipment. The master control device is electrically connected with the massage bathing control unit and comprises a logs-collecting unit. The massage bathing control unit is electrically connected with the at least one attached device and comprises a detection-feedback device and a control unit. The detection-feedback device is configured to detect the at least one attached device, and the control unit is configured to control the detection-feedback device to generate and transmit at least one actuating message to the master control device according to at least one detection result of the at least one attached device, to make the log-collecting unit of the master control device record the at least one actuating message into a logs table. The analyzing unit analyzes the at least one actuating message to determine whether an abnormal situation and/or an aging situation has occurred on the at least one attached device. Each of the at least one detection-feedback devices comprises at least one switching unit and at least one sensing unit. The at least one switching unit comprises a first switching unit, a second switching unit, and a third switching unit. The method comprising:

First, proceeding at least one turn-on test process of the at least one switching unit by the control unit. Then, proceeding at least one aging and malfunctioned process of the at least one attached device by the control unit. Then, proceeding at least one turn-off test process of the at least one switching unit by the control unit. Finally, ending the method.

In a preferred embodiment, the at least one turn-on test process of the at least one switching unit further comprises:

First, making the first switching unit, the second switching unit and the third switching unit in non-conducted state. Then, making orderly or disorderly the first switching unit, the second switching unit and the third switching unit in conducted state. Then, determining whether at least one of the first switching unit, the second switching unit, and the third switching unit is normally conducted. Then, recording in the logs table and/or displaying on the display screen.

In a preferred embodiment, the at least one aging-malfunctioned test process of the at least one attached device further comprises:

First, calculating an aging slope of a current-time curve of the at least one attached device according to the logs table by the analyzing unit. Then, determining whether to exchange the at least one attached device according to the aging slope by the analyzing unit. Then, determining whether the current of the at least one attached device is less than a preset current by the analyzing unit.

In a preferred embodiment, the at least one turn-off test process of the at least one switching unit further comprises the following steps of:

First, making the first switching unit, the second switching unit, and the third switching unit in conducted state. Then, making orderly or disorderly the first switching unit, the second switching unit, and the third switching unit in non-conducted state. Then, determining whether at least one of the first switching unit, the second switching unit, and the third switching unit is normally non-conducted. Then, recording in the logs table and/or displaying on the display screen.

In a preferred embodiment, while one or a combination of several of the first switching unit, the second switching unit, and the third switching unit which is/are unable to perform normally non-conduction is confirmed, the method further comprises:

First, generating the at least one actuating message to record in the logs table and/or displaying on the display screen. Finally, ending the method.

In a preferred embodiment, while the analyzing unit confirms that the at least one attached device needs to be exchanged according to the aging slope, the method further comprises:

First, generating the at least one actuating message to record in the logs table and/or displaying on the display screen. Finally, ending the method.

In a preferred embodiment, while the analyzing unit confirms that the current of the at least one attached device is greater than or equal to the preset current, the method further comprises:

First, generating the at least one actuating message to record in the logs table and/or displaying on the display screen. Finally, ending the method.

In a preferred embodiment, while one or a combination of several of the first switching unit, the second switching unit, and the third switching unit which is/are unable to perform normally conduction is confirmed, the method further comprises:

First, generating the at least one actuating message to record in the logs table and/or displaying on the display screen. Finally, ending the method.

In a preferred embodiment, the at least one attached device comprises a heater.

In a preferred embodiment, the at least one switching unit is a relay, the at least one sensing unit is a current sensor and/or a photo coupler.

In order to solve the aforementioned drawbacks, another objective of the present invention is to provide a self-detection method of the message bathing maintenance system, the massage bathing maintenance system comprises an operating panel unit, a master control device, at least one attached device, an analyzing unit, and a massage bathing control unit, the operating panel unit is electrically connected with the master control device, and comprises a display screen to show an actuating status of the at least one attached device with regard to a massage bathing equipment, the master control device is electrically connected with the massage bathing control unit and comprises a logs-collecting unit, the massage bathing control unit is electrically connected with the at least one attached device and comprises a detection-feedback device and a control unit, the detection-feedback device is configured to detect the at least one attached device, and the control unit is configured to control the detection-feedback device to generate and transmit at least one actuating message to the master control device according to at least one detection result of the at least one attached device, to make the log-collecting unit of the master control device record the at least one actuating message into a logs table, and the analyzing unit analyzes the at least one actuating message to determine whether an abnormal situation and/or aging situation occurs on the at least one attached device, each of the at least one detection-feedback devices comprise at least one switching unit and at least one sensing unit, the at least one switching unit comprises a first switching unit and a second switching unit, the method comprising:

First, proceeding at least one turn-on test process of the at least one switching unit by the control unit. Then, proceeding at least one aging-malfunctioned test process of the at least one attached device by the control unit. Then, proceeding at least one turn-off test process of the at least one switching unit by the control unit. Finally, ending the method.

In a preferred embodiment, the at least one turn-on test process of the at least one switching unit further comprising:

First, making the first switching unit and the second switching unit in non-conducted state. Then, making orderly or disorderly the first switching unit and the second switching unit in conducted state. Then, determining whether at least one of the first switching unit and the second switching unit is normally conducted. Then, recording in the logs table and/or displaying on the display screen.

In a preferred embodiment, the at least one aging-malfunctioned test process of the at least one attached device further comprising:

First, calculating an aging slope of a current-time curve of the at least one attached device according to the logs table by the analyzing unit. Then, determining whether to exchange the at least one attached device according to the aging slope by the analyzing unit. Then, determining whether the current of the at least one attached device is less than a preset current by the analyzing unit.

In a preferred embodiment, the at least one turn-off test process of the at least one switching unit further comprising:

First, making the first switching unit and the second switching unit in conducted state. Then, making orderly or disorderly the first switching unit and the second switching unit in non-conducted state. Then, determining whether at least one of the first switching unit and the second switching unit is normally non-conducted. Then, recording in the logs table and/or displaying on the display screen.

In a preferred embodiment, while one or a combination of several of the first switching unit and the second switching unit which is/are unable to perform normally non-conduction is confirmed, the method further comprising:

First, generating the at least one actuating message to record in the logs table and/or displaying on the display screen. Finally, ending the method.

In a preferred embodiment, while the analyzing unit confirms that the at least one attached device needs to be exchanged according to the aging slope, the method further comprising:

First, generating the at least one actuating message to record in the logs table and/or displaying on the display screen. Finally, ending the method.

In a preferred embodiment, while the analyzing unit confirms that the current of the at least one attached device is greater than or equal to the preset current, the method further comprising:

First, generating the at least one actuating message to record in the logs table and/or displaying on the display screen. Finally, ending the method.

In a preferred embodiment, while a current of the at least one attached device has one or a combination of several of a high frequency variation, an instant impulse, and a low frequency variation, the method further comprising:

First, generating the at least one actuating message to record in the logs table and/or displaying on the display screen. Finally, ending the method.

In a preferred embodiment, while one or both of the first switching unit and the second switching unit which is/are unable to perform normally conduction is confirmed, the method further comprising:

First, generating the at least one actuating message to record in the logs table and/or displaying on the display screen. Finally, ending the method.

In a preferred embodiment, the at least one attached device comprises a combination of several of a blower, a motor, an air valve, a sensor, a pump, an ozone generator, a light controlling device and a heater.

In a preferred embodiment, the at least one switching unit is a relay, the at least one sensing unit is a current sensor and/or a photo coupler.

In order to solve the aforementioned drawbacks, another objective of the present invention is to provide a self-detection method of the massage bathing maintenance system, the massage bathing maintenance system comprises an operating panel unit, a master control device, at least one attached device, an analyzing unit, and a massage bathing control unit, the operating panel unit is electrically connected with the master control device, and comprises a display screen to show actuating status of the at least one attached device with regard to a massage bathing equipment, the master control device is electrically connected with the massage bathing control unit and comprises a logs-collecting unit, the massage bathing control unit is electrically connected with the at least one attached device and comprises a detection-feedback device and a control unit, the detection-feedback device is configured to detect the at least one attached device, and the control unit is configured to control the detection-feedback device to generate and transmit at least one actuating message to the master control device according to at least one detection result of the at least one attached device, to make the log-collecting unit of the master control device record the at least one actuating message into a logs table, and the analyzing unit analyzes the at least one actuating message to determine whether an abnormal situation and/or aging situation has occurred in the at least one attached device, each of the at least one detection-feedback device comprises at least one switching unit and at least one sensing unit, the at least one switching unit comprises a first switching unit, the method comprising:

First, proceeding at least one turn-on test process of the at least one switching unit by the control unit. Then, proceeding at least one aging-malfunctioned test process of the at least one attached device by the control unit. Then, proceeding at least one turn-off test process of the at least one switching unit by the control unit. Finally, ending the method.

In a preferred embodiment, the at least one turn-on test process of the at least one switching unit further comprises:

First, making the at least one switching unit in non-conducted state. Then, making orderly or disorderly the at least one switching unit in conducted state. Then, determining whether at least one switching unit is normally conducted. Then, recording in the logs table and/or displaying on the display screen.

In a preferred embodiment, the at least one aging-malfunctioned test process of the at least one attached device further comprises:

First, calculating an aging slope of a current-time curve of the at least one attached device according to the logs table by the analyzing unit. Then, determining whether to exchange the at least one attached device according to the aging slope by the analyzing unit. Then, determining whether the current of the at least one attached device is less than a preset current by the analyzing unit.

In a preferred embodiment, the at least one turn-off test process of the at least one switching unit further comprises:

First, making the at least one switching unit in conducted state. Then, making orderly or disorderly the at least one switching unit in non-conducted state. Then, determining whether the at least one switching unit is normally non-conducted. Then, recording in the logs table and/or displaying on the display screen.

In a preferred embodiment, while the at least one switching unit which is/are unable to perform normally non-conduction is confirmed, the method further comprises:

First, generating the at least one actuating message to record in the logs table and/or displaying on the display screen. Finally, ending the method.

In a preferred embodiment, while the analyzing unit confirms that the at least one attached device needs to be exchanged according to the aging slope, the method further comprising:

First, generating the at least one actuating message to record in the logs table and/or displaying on the display screen. Finally, ending the method.

In a preferred embodiment, while the analyzing unit confirms that the current of the at least one attached device is greater than or equal to the preset current, the method further comprising:

First, generating the at least one actuating message to record in the logs table and/or displaying on the display screen. Finally, ending the method.

In a preferred embodiment, while a current of the at least one attached device has one or a combination of several of a high frequency variation, an instant impulse, and a low frequency variation, the method further comprising:

First, generating the at least one actuating message to record in the logs table and/or displaying on the display screen. Finally, ending the method.

In a preferred embodiment, while the at least one switching units which is unable to perform normally conduction is confirmed, the method further comprising:

First, generating the at least one actuating message to record in the logs table and/or displaying on the display screen. Finally, ending the method.

In a preferred embodiment, the at least one attached device comprises one or a combination of several of a blower, a motor, an air valve, a sensor, a pump, an ozone generator, a light controlling device, and a heater.

In a preferred embodiment, the at least one switching unit is a relay, the at least one sensing unit is a current sensor and/or a photo coupler.

DETAILED DESCRIPTION OF THE PREFERRED EMBODIMENTS

Figure 1:
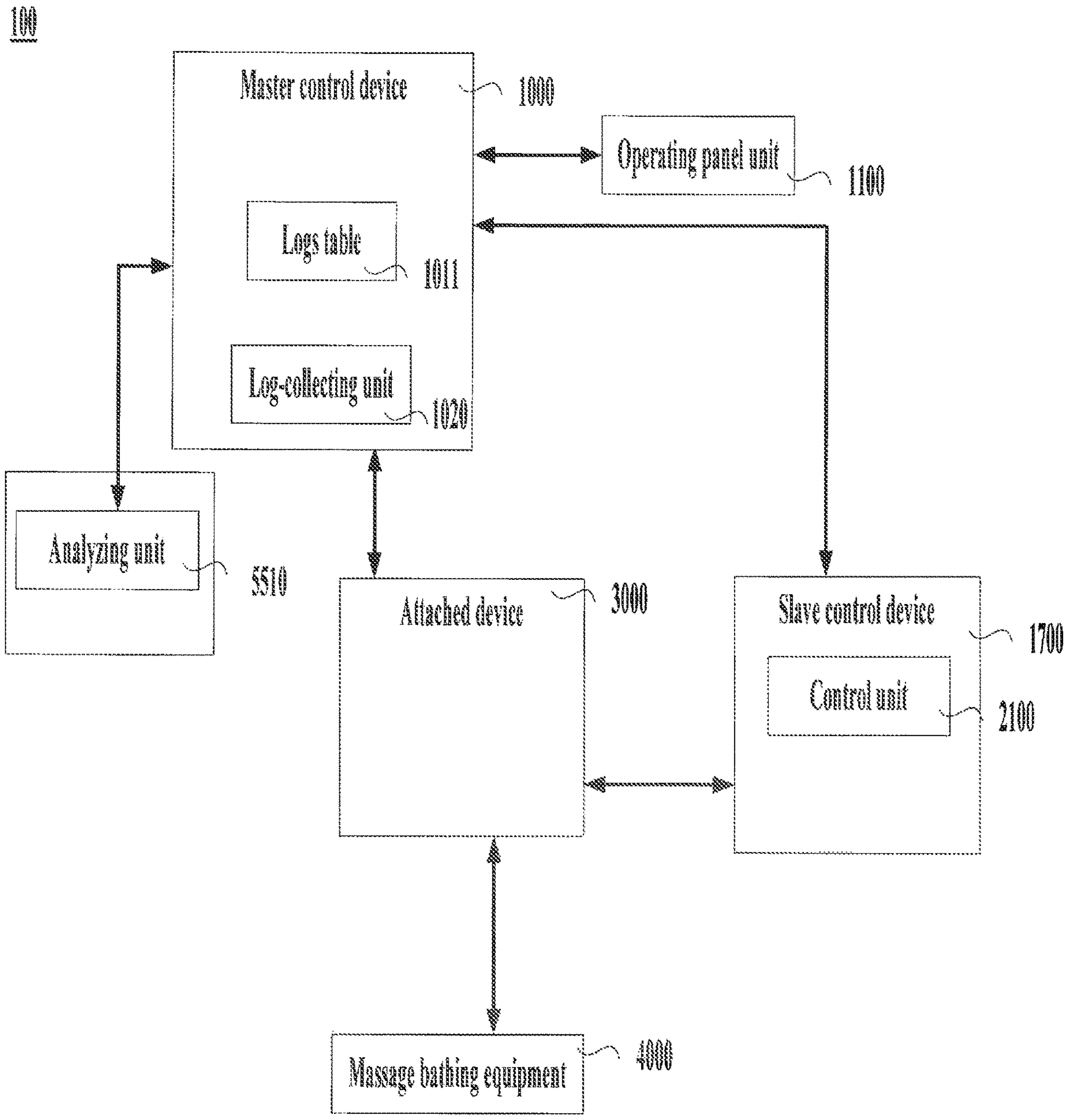
FIG. 1 is an illustrative view of a massage bathing maintenance system according to a first preferred embodiment of the present invention.

This description of the exemplary embodiments is intended to be read in connection with the accompanying drawings, which are to be considered part of the entire written description. In the description, relative terms such as “lower”, “upper”, “horizontal”, “vertical”, “above”, “below”, “up”, “down”, “top”, and “bottom”, as well as derivatives thereof (e.g., “horizontally”, “downwardly”, “upwardly”, etc.) should be construed with reference of the orientation as then described or as shown in the drawing under discussion. These relative terms are for convenience of description and do not require that the apparatus be constructed or operated in a particular orientation, and do not limit the scope of the invention.

Refer to FIG. 1, which is an illustrative view of a massage bathing maintenance system 100 according to a first preferred embodiment of the present invention. In the massage bathing maintenance system 100, which is applied for a massage bathing equipment 4000, the massage bathing equipment 4000 can be a massage bathtub/hot tub, a SPA pool, or a swimming pool. The massage bathing maintenance system 100 comprises an operating panel unit 1100, at least one attached device 3000, at least one slave control device 1700, a master control device 1000, and an analyzing unit 5510. Even though the massage bathing maintenance system 100 comprises several same-level devices, such as several attached devices 3000 or several slave control devices 1700, by using a graphic of single device as a representative in following figs, but is not to limit the numbers of the devices.

Please refer to FIG. 1, the at least one attached device 3000 is configured to actuate to the massage bathing equipment 4000; in other embodiments, the at least one attached device 3000 can be disposed into the at least one slave control device 1700. The at least one slave control device 1700 comprises a control unit 2100 configured to generate and transmit at least one actuating message according to at least one actuating-status, the at least one actuating-status means what is done to the massage bathing equipment 4000 by the at least one attached device 3000. The actuating message is an abnormal code, a physical value (such as voltage value, current value, or logical determined value), or a chemical value. The master control device 1000 controls the at least one slave control device 1700 through a master-slave connection therebetween, for receiving the at least one actuating message. The master control device 100 comprises a logs table 1011 and a log-collecting unit 1020. The log-collecting unit 1020 is configured to record the at least one actuating message of the at least one slave control device 1700 into a logs table 1011.

The analyzing unit 5510 is configured to analyze the at least one actuating message of the logs table 1011 of the master control device 1000 so as to determine whether the actuation of the at least one attached device 3000 is abnormal. In the embodiment, the analyzing unit 5510 checks or compares a corresponding content recorded in a built-in table according to the at least one actuating message to determine whether an abnormal situation and/or aging situation has occurred in some specific elements (such as the at least one attached device 3000). In the embodiment of FIG. 1, although the analyzing unit 5510 is disposed inside an operational local or remote device, which is outside the master control device 1000, the local or remote device can be, for example, a computer or server or mobile phone, or a tablet PC or other portable electronic product, the analyzing unit 5510 could be one or a combination of software, hardware, and firmware. Meanwhile, in other embodiments, the analyzing unit 5510 is able to be disposed inside one of the master control device 1000, the slave control device 1700, and other device. Hence, the disposed position of the analyzing unit 5510 is not limited in the present invention, it is only needed that the analyzing unit 5510 is able to cooperate with the master control device 1000. Besides, in other function sides, the control unit 2100 of the at least one slave control device 1700 is able to further generate the at least one actuating message according to at least one preset self-detecting operation process and feed the at least one actuating message back to the master control device 1000 or the other slave control device 1700. The master control device 1000 generates at least one controlling message to the at least one slave control device 1700, to ask the control unit 2100 of the at least one slave control device 1700 to generate and feed back the at least one actuating message. The master control device 1000 is able to generate an informing message according to a determined result with respect to the at least one actuating message, and to transmit the notice information to an operator through the operating panel unit 1100, or wireless communication internet, or cable internet. Besides, the operator is able to proceed various operations or setups or to receive the actuating message feedback from the devices or operating the feedback information, by using the operating panel unit 1100 to actuate the slave control device 1700 or the attached device 3000 through the master control device 1000.

Figure 2:
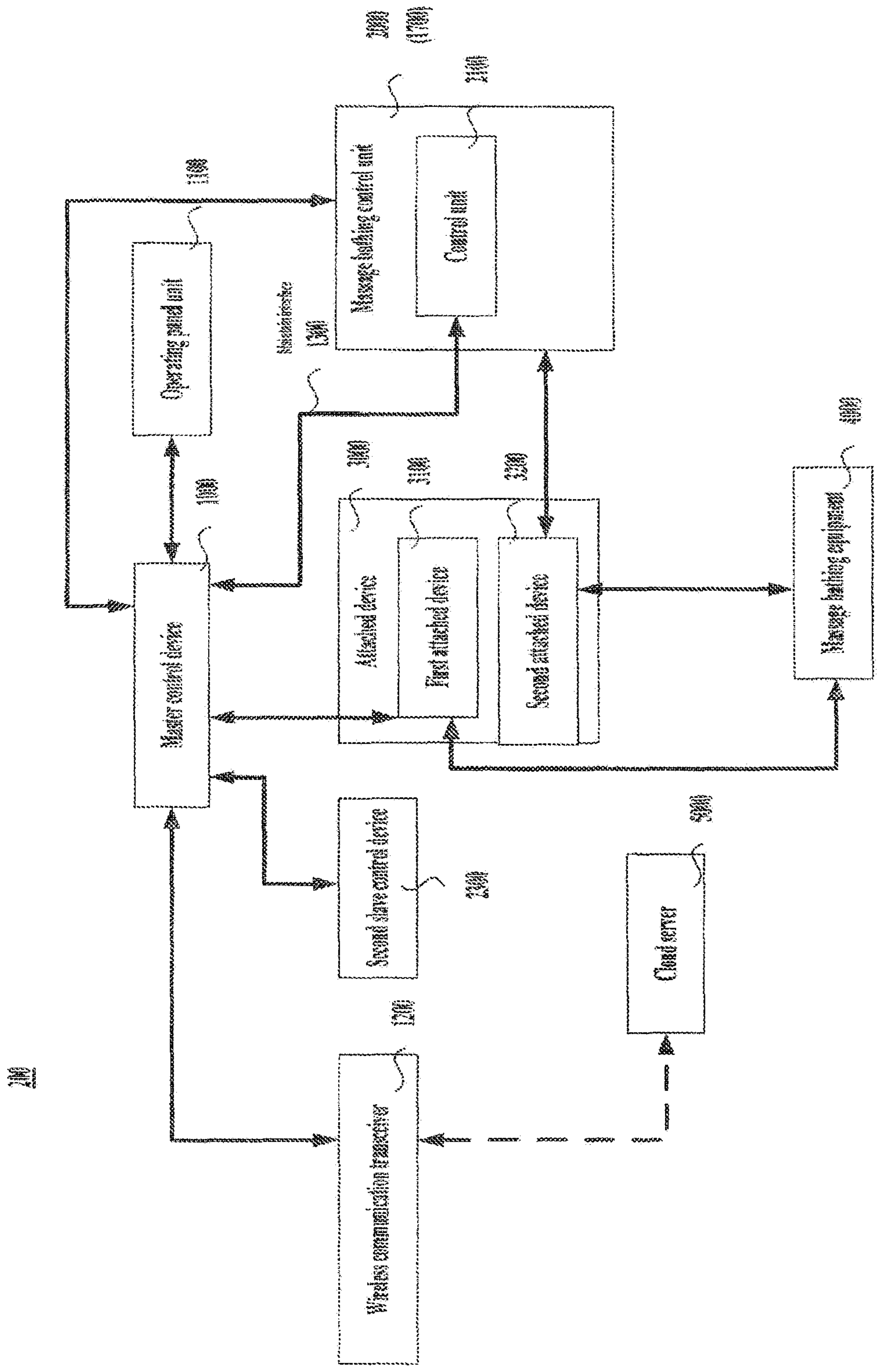
FIG. 2 is an illustrative view of a massage bathing maintenance system according to a second preferred embodiment of the present invention.

With reference to FIG. 1 and FIG. 2, FIG. 2 is an illustrative view of a massage bathing maintenance system 200 according to a second preferred embodiment of the present invention. The difference between the second preferred embodiment and the first preferred embodiment is: the second preferred embodiment adds at least one wireless communication transceiver 1200, at least one second slave control device 2300, and a maintain interface 1300. The at least one slave control device 1700 of the first preferred embodiment is practically a massage bathing control unit 2000 (like a SPA controller). In the second preferred embodiment, the massage bathing maintenance system 200 further selectively disposes a cloud server 5000 or not, so the connecting line between the cloud server 5000 and the wireless communication transceiver 1200 is drawn as dashed line. The cloud server 5000 is respectively connected to the master control device 1000 and the at least one slave control device 1700 via the at least one wireless communication transceiver 1200, to proceed a remote trouble shooting/maintenance operation. The master control device 1000 can work independently, regardless of whether the massage bathing maintenance system 200 is connected with the cloud server 5000 or not. The master control device 1000 proceeds at least one maintaining operation via the maintain interface 1300 which is one or both of JTAG and RESET.

The drawings of FIGS. 1 and 2, which are a schematic diagram of functional blocks of each elements of the massage bathing maintenance system 100, 200, but do not to limit the actual physical position, the master control device 1000 and any one of the slave control devices 1700 (such as the massage bathing control unit 2000) can be incorporated into one device, or the master control device 1000 and the operating panel unit 1100 can be incorporated into one device.

Figure 3:
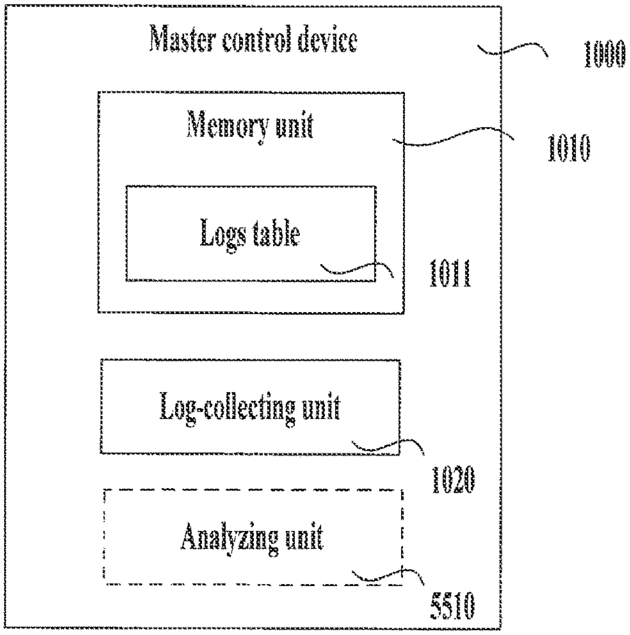
FIG. 3 is a composing view of the master control device of FIG. 2.

With reference to FIGS. 2 and 3, FIG. 3 is a composing view of the master control device 1000 of FIG. 2. The master control device 1000 further comprises a memory unit 1010 for storing the logs table 1011, the logs table 1011 is further configured to locate communication records between the master control device 1000 and the at least one slave control device 1700 (such as the massage bathing control unit 2000). The master control device 1000 further selectively disposes an analyzing unit or not (drawn as dashed line). In one embodiment, the master control device 1000 is connected with the cloud server 5000, the analyzing unit 5510 can selectively not to be disposed inside the master control device 1000 or in the cloud server 5000. In one embodiment, the master control device 1000 does not connect with the cloud server 5000, and the analyzing unit 5510 can selectively be disposed inside the master control device 1000.

Figure 4:
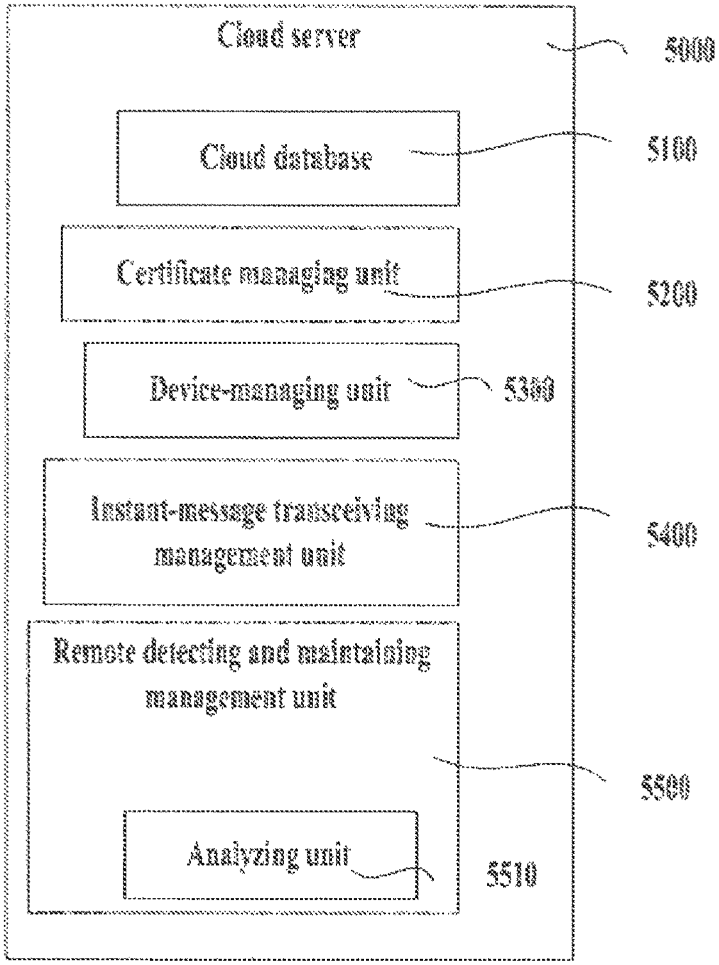
FIG. 4 is a composing view of the cloud server of FIG. 2.

With reference to FIGS. 2 and 4, FIG. 4 is a composite view of the cloud server 5000 of FIG. 2. The cloud server 5000 comprises at least one cloud database 5100, a certificate managing unit 5200, an unit managing unit 5300, an instant-message transceiving management unit 5400, and a remote detecting and maintaining management unit 5500, the remote detecting and maintaining management unit 5500 comprises the analyzing unit 5510, the at least one cloud database 5100 is configured to store a corresponding serial number of the massage bathing equipment 4000.

With reference to FIGS. 2, 3, and 4, the massage bathing maintenance system uses the at least one wireless communication transceiver 1200 to connect the cloud server 5000, and to transmit the logs table 1011 from the master control device 1000 to the at least one cloud database 5100 of the cloud server 5000 for storing. The cloud server 5000 sends a request to the master control device 1000, which collects the at least one actuating message from the at least one slave control device 1700 (such as the massage bathing control unit 2000), to the logs table 1011, then stores the logs table 1011 in the master control device 1000 and/or transmits the logs table 1011 from the master control device 1000 to the at least one cloud database 5100 of the cloud server 5000, for storage of for maintenance usage. The cloud server 5000 makes the remote detecting and maintaining management unit 5500 to proceed at least one preset remote detecting and maintaining management process 7000 (please refer to FIG. 18) according to a determined result, made by the analyzing unit 5510, with respect to the at least one actuating message of the logs table 1011. The master control device 1000 generates the at least one controlling message to the at least one slave control device 1700 according to the preset remote detecting and maintaining management process 7000 (please refer to FIG. 18), and the master control device 1000 requests the control unit 2100 of the at least one slave control device 1700 to proceed warm reboots and a detection so that the at least one slave control device 1700 generates the at least one actuating message including the detection result. The master control device 1000 proceeds at least one maintenance operation according to the preset remote detecting and maintaining management process 7000 (please refer to FIG. 18), and after the at least one maintenance operation 7000 is proceeded, the master control device 1000 requests the control unit 2100 of the at least one slave control device 1700 to proceed the detection, then the at least one slave control device 1700 generates the at least one actuating message including the detection result, wherein the at least one maintaining operation comprises one or a combination of several of wrong setup corrections, cold reboots, source code reinstallations, and software version updates.

Figure 5:
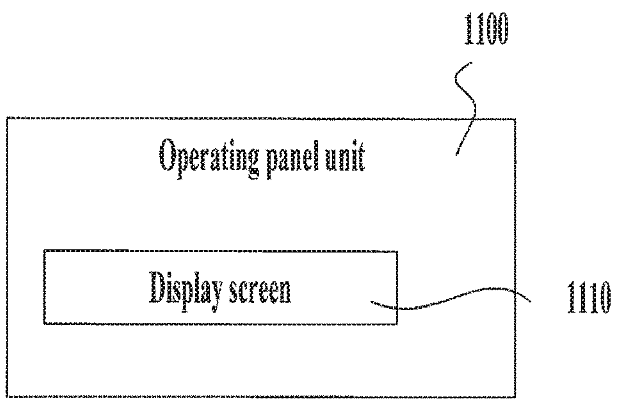
FIG. 5 is a composing view of the operating panel unit of FIG. 1.

With reference of FIGS. 1 and 5, FIG. 5 is a composing view of the operating panel unit 1100 of FIGS. 1, 2. The operating panel unit 1100 is electrically connected with the master control device 1000, and comprises a display screen to show the informing message.

Figure 6:
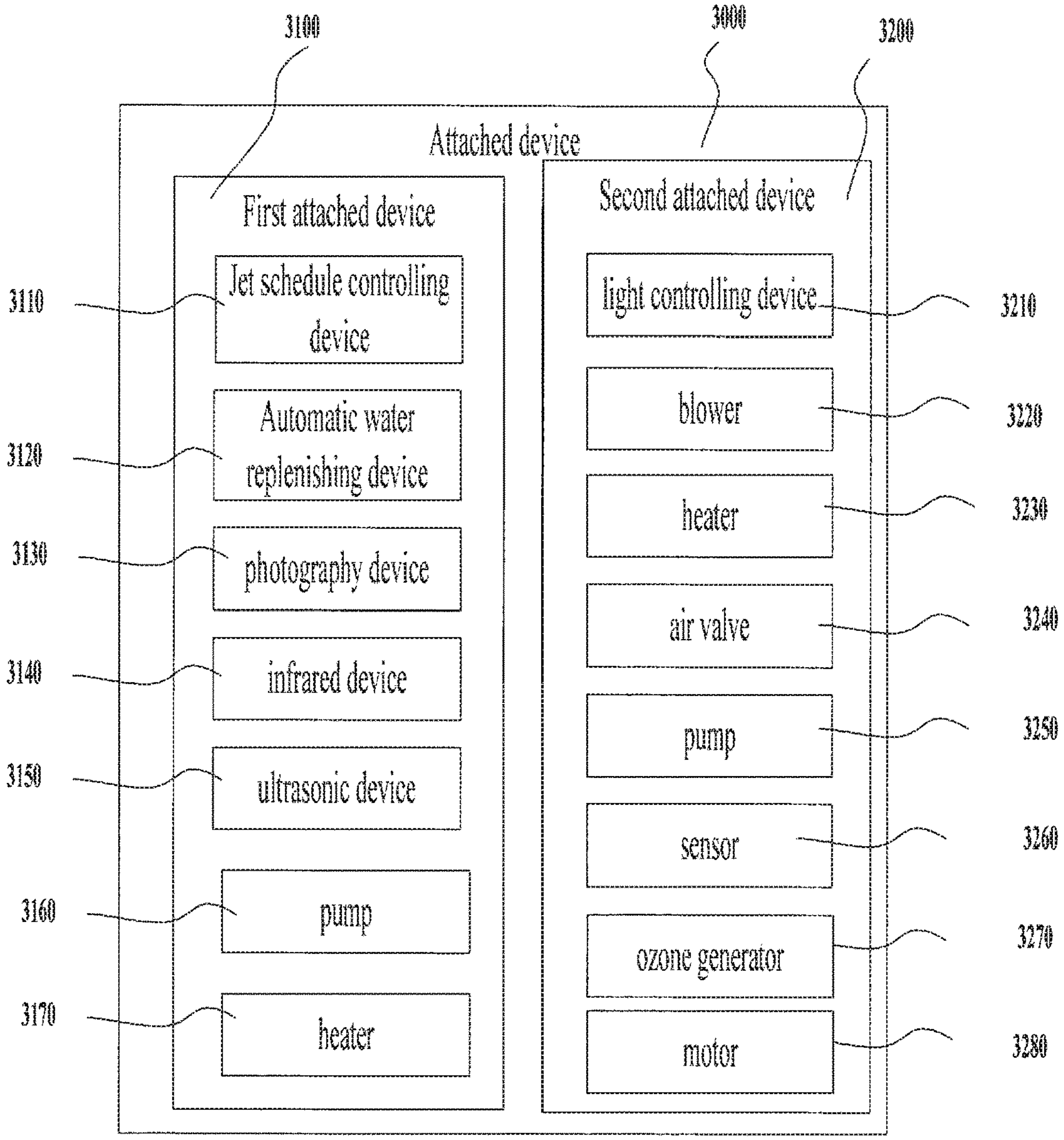
FIG. 6 is a composing view of the attached device of FIGS. 1, 2.

FIG. 6 is a composite view of the attached device 3000 of FIGS. 1, 2. The attached device 3000 comprises at least one first attached device 3100 and at least one second attached devices 3200. The at least one first attached devices comprise a jet schedule controlling device 3110, an automatic water replenishing device 3120, a photography device 3130, an infrared device 3140, an ultrasonic device 3150, a pump 3160, and a heater 3170. The at least one second attached device comprises a light controlling device 3210, a blower 3220, a heater 3230, an air valve 3240, a pump 3250, a sensor 3260, an ozone generator 3270, and a motor 3280.

Figure 7:
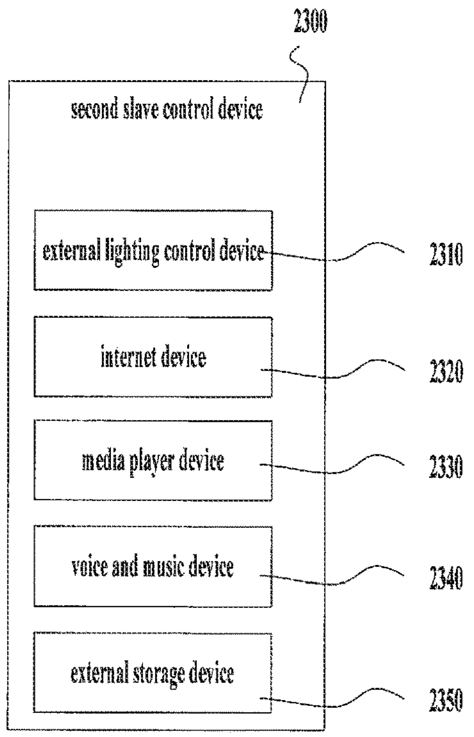
FIG. 7 is a composing view of the second slave control device of FIG. 2.

FIG. 7 is a composite view of the second slave control device 2300 of FIG. 2. The at least one second slave control device 2300 comprises an external lighting control device 2310, an internet device 2320, a media player device 2330, a voice and music device 2340, and an external storage device 2350.

Figure 8:
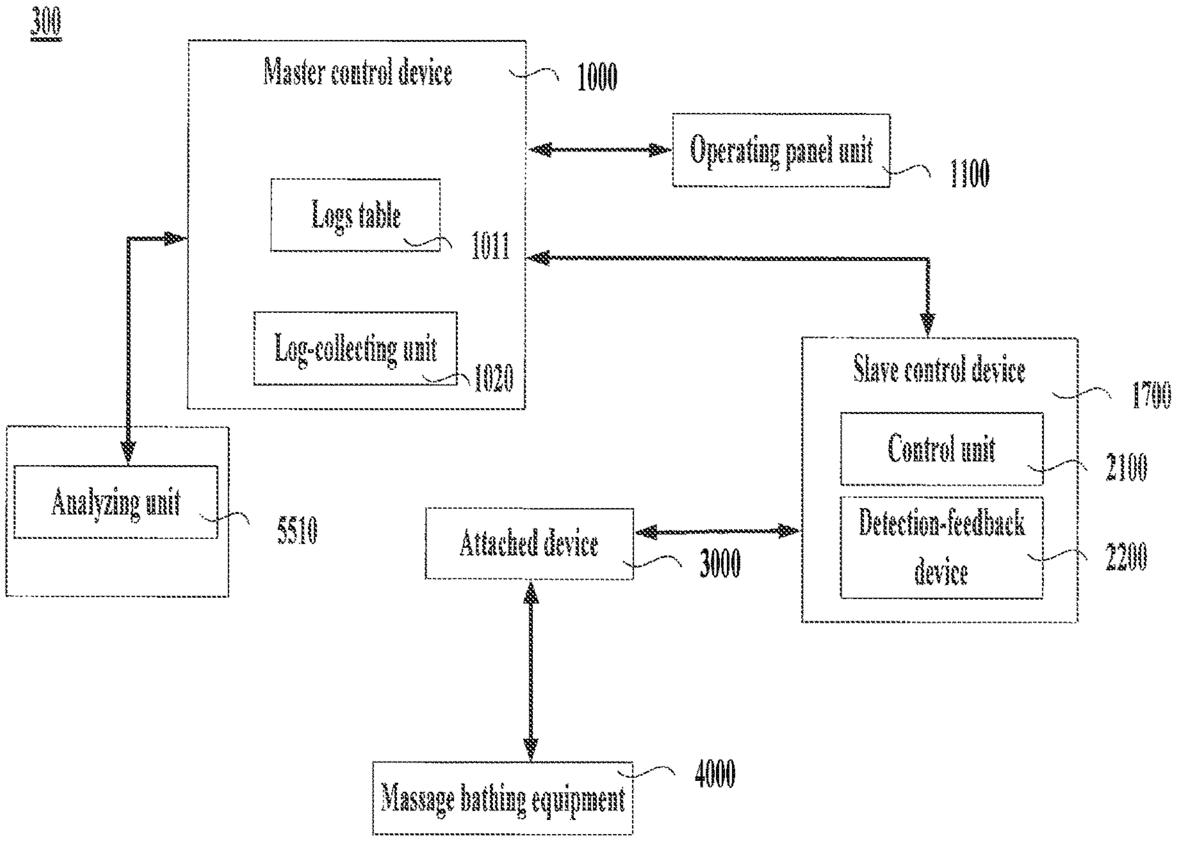
FIG. 8 is an illustrative view of a massage bathing maintenance system according to a third preferred embodiment of the present invention.

With reference of FIGS. 1 and 8, FIG. 8 is an illustrative view of a massage bathing maintenance system 300 according to a third preferred embodiment of the present invention. The difference between the third preferred embodiment and the first preferred embodiment is: the third preferred embodiment adds a detection-feedback device 2200, wherein the control unit 2100 is configured to control the detection-feedback device 2200 to detect the at least one attached device 3000 and to generate and transmit at least one actuating message to the master control device 1000.

Figure 9:
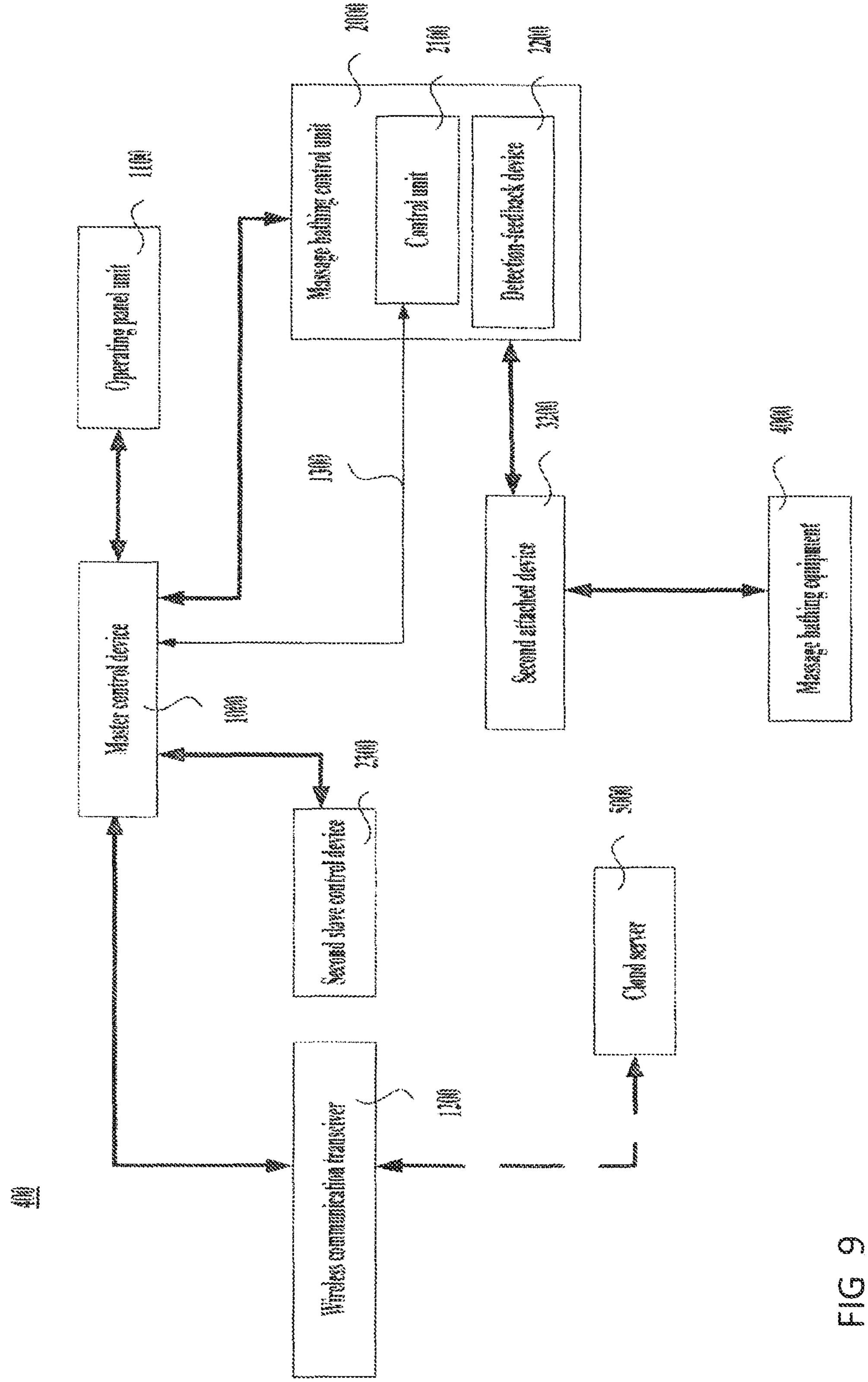
FIG. 9 is an illustrative view of a massage bathing maintenance system according to a fourth preferred embodiment of the present invention.

FIG. 9 is an illustrative view of a massage bathing maintenance system 400 according to a fourth preferred embodiment of the present invention. The difference between the fourth preferred embodiment and the third preferred embodiment is: the fourth preferred embodiment adds at least one wireless communication transceiver 1200, at least one second slave control device 2300, and a maintain interface 1300. The fourth preferred embodiment is able to selectively dispose a cloud server 5000 or not (drawn as dashed line). The other components are like the first preferred embodiment and the second preferred embodiment, the relative content can be referred to the above description.

Figure 10:
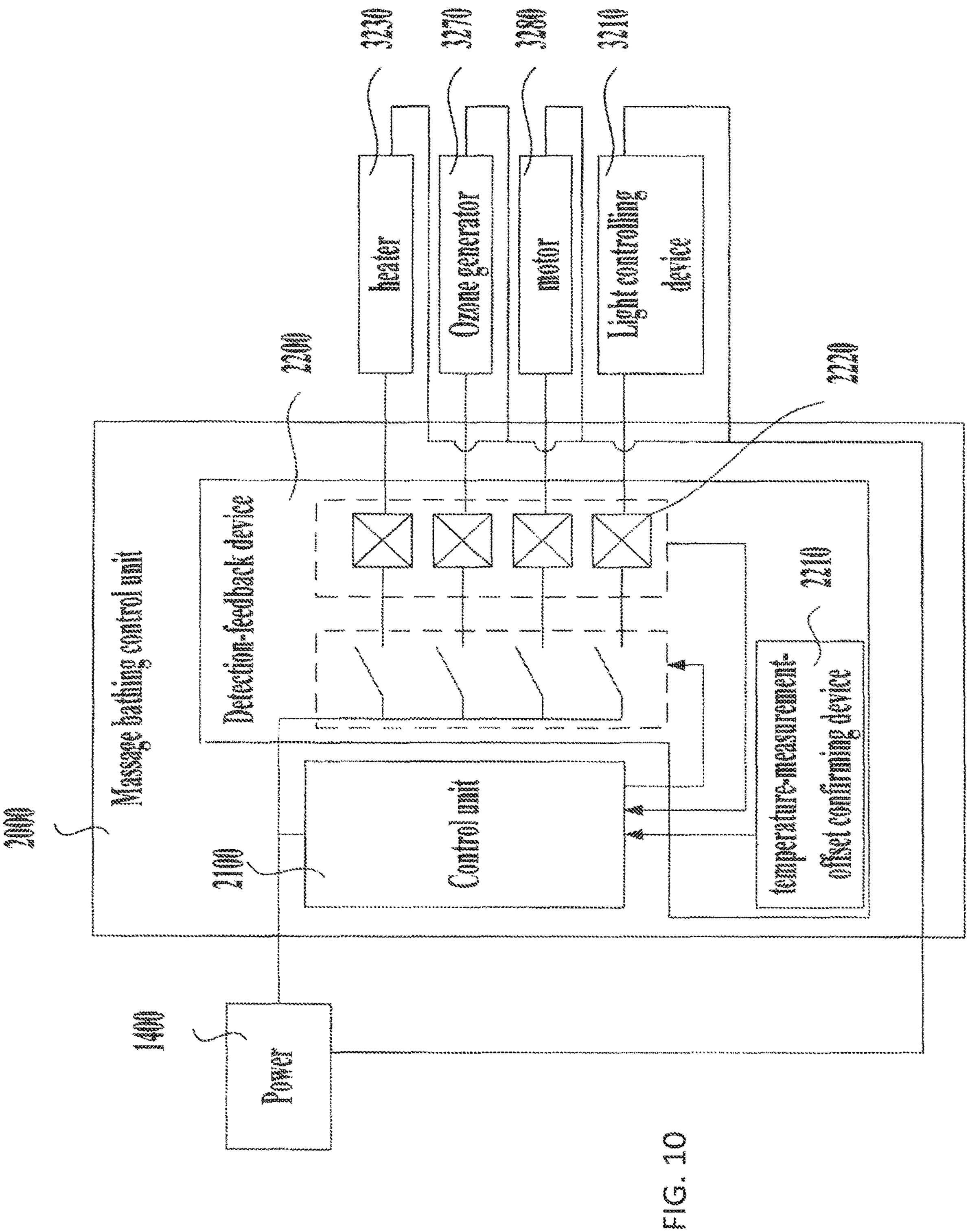
FIG. 10 is an illustrative view of a first composite type of the massage bathing control unit and each of the second attached devices of the massage bathing maintenance system of FIG. 9.
Figure 11:
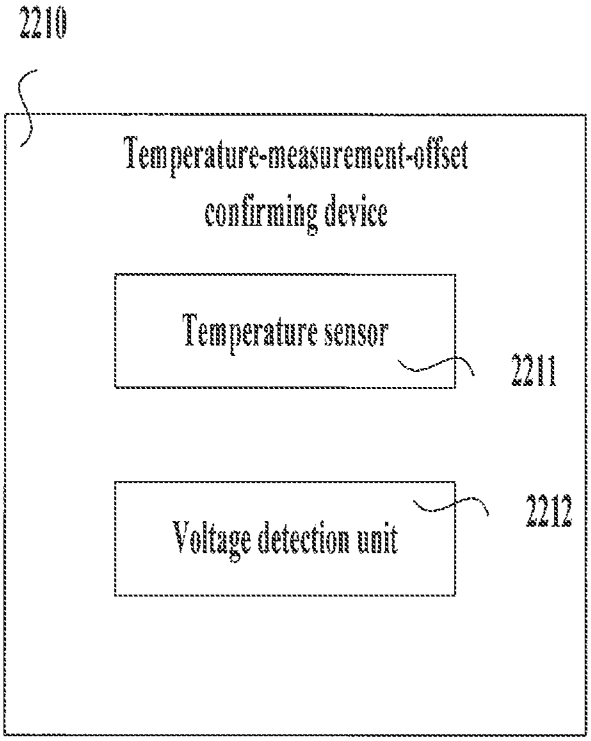
FIG. 11 is a composing view of the temperature-measurement-offset confirming device of FIG. 10.

With reference of FIGS. 9 and 10, FIG. 10 is an illustrative view of a first composite type of the massage bathing control unit 2000 and each of the second attached devices of the massage bathing maintenance system 400 of FIG. 9. The first composite type comprises a power 1400, a massage bathing control unit 2000, and several second attached devices 3210-3280. Herein, the devices of the second attached device 3200 of FIG. 6 are represented as example, but are not to limited to connecting with the at least one attached device 3000 (including the first attached device 3100 and the second attached device 3200). The massage bathing control unit 2000 comprises a control unit 2100, a detection-feedback device 2200, and a temperature-measurement-offset confirming device 2210. The detection-feedback device 2200 comprises at least one switching unit and at least one sensing unit 2220. The at least one switching unit can be a relay. The at least one switching unit is controlled by the control unit 2100 to turn on or turn off the power 1400 which is configured to provide the at least one second attached device. In the preferred embodiment, the at least one switching unit is established by four switching units, the at least one sensing unit 2220 comprises four sensing units 2220 to respectively dispose at different positions between the switching units and the second attached devices 3200 (including the heater 3230, the ozone generator 3270, the motor 3280, and the light controlling device 3210), to detect a specific physical value between the he switching units and the second attached devices 3200, and to transmit the specific physical value to the control unit 2100. The control unit 2100 generates the at least one actuating message according to the specific physical value as the detection result and provides the at least one actuating message to the master control device 1000. The specific physical value is a current value or a logical determined value. FIG. 11 is a composite view of the temperature-measurement-offset confirming device 2210 of FIG. 10. The temperature-measurement-offset confirming device 2210 comprises a temperature sensor 2211 and a voltage detection unit 2212, the temperature-measurement-offset confirming device 2210 uses data detected by the temperature sensor 2211 and the voltage detection unit 2212 for determining whether the temperature sensor 2211 is abnormal.

Figure 12:
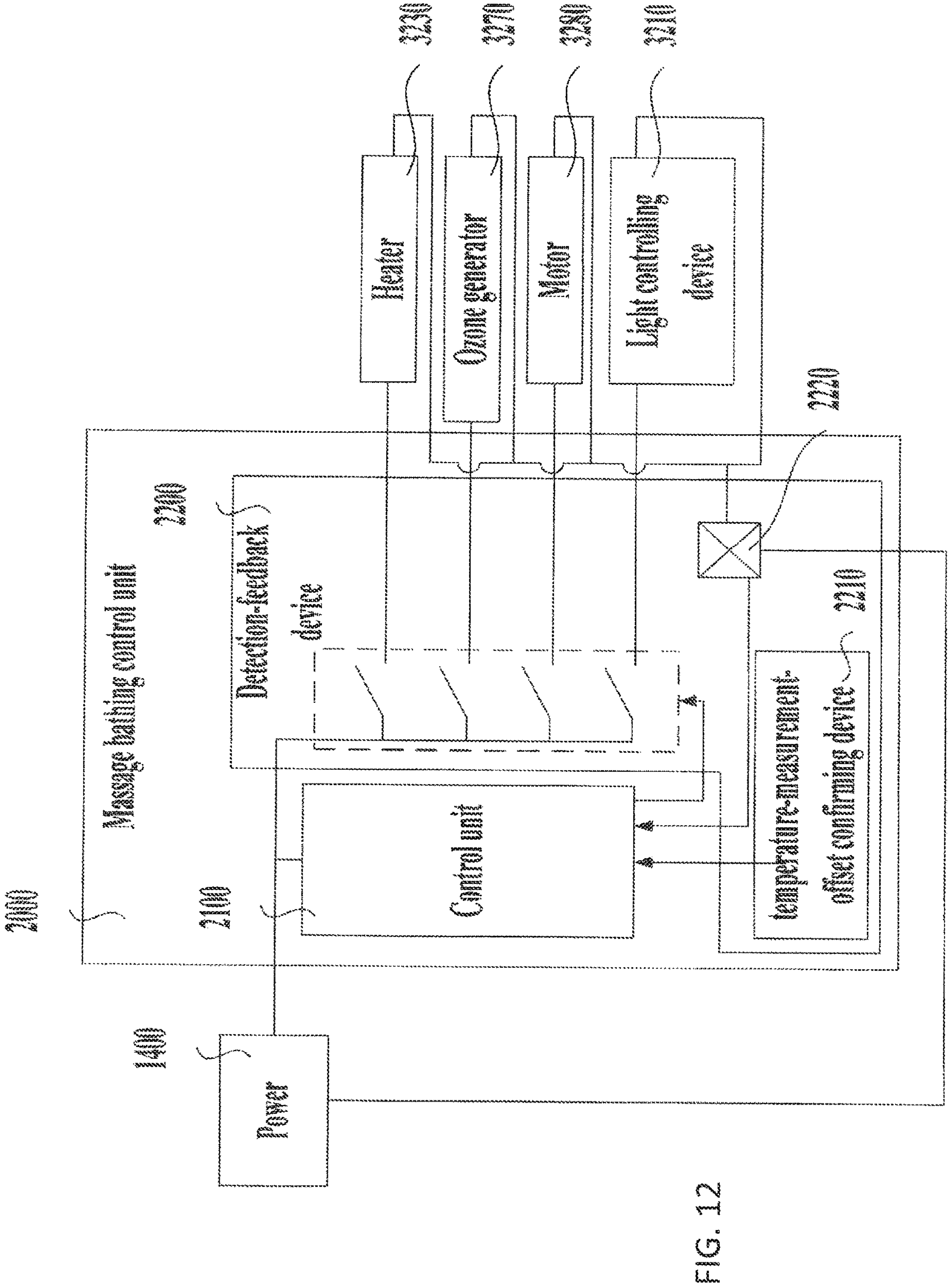
FIG. 12 is an illustrative view of a second composite type of the massage bathing control unit and each of the second attached devices according to the massage bathing maintenance system of FIG. 9.

With reference of FIGS. 9 and 12, FIG. 12 is an illustrative view of a second composite type of the massage bathing control unit 2000 and each of the second attached devices according to the massage bathing maintenance system 400 of FIG. 9. The difference from the first composite type of FIG. 10 is: The detection-feedback device 2200 of the massage bathing control unit 2000 disposes a sensing unit 2220 between the several second attached devices 3200 (including the heater 3230, the ozone generator 3270, motor 3280, and light controlling device 3210) and the control unit 2100, to detect specific physical values, and to transmit the specific physical values to the control unit 2100, then the control unit 2100 generates the at least one actuating message according to the detection result (based on the detected specific physical values) and provides the at least one actuating message to the master control device 1000 as in FIG. 9.

Figure 13:
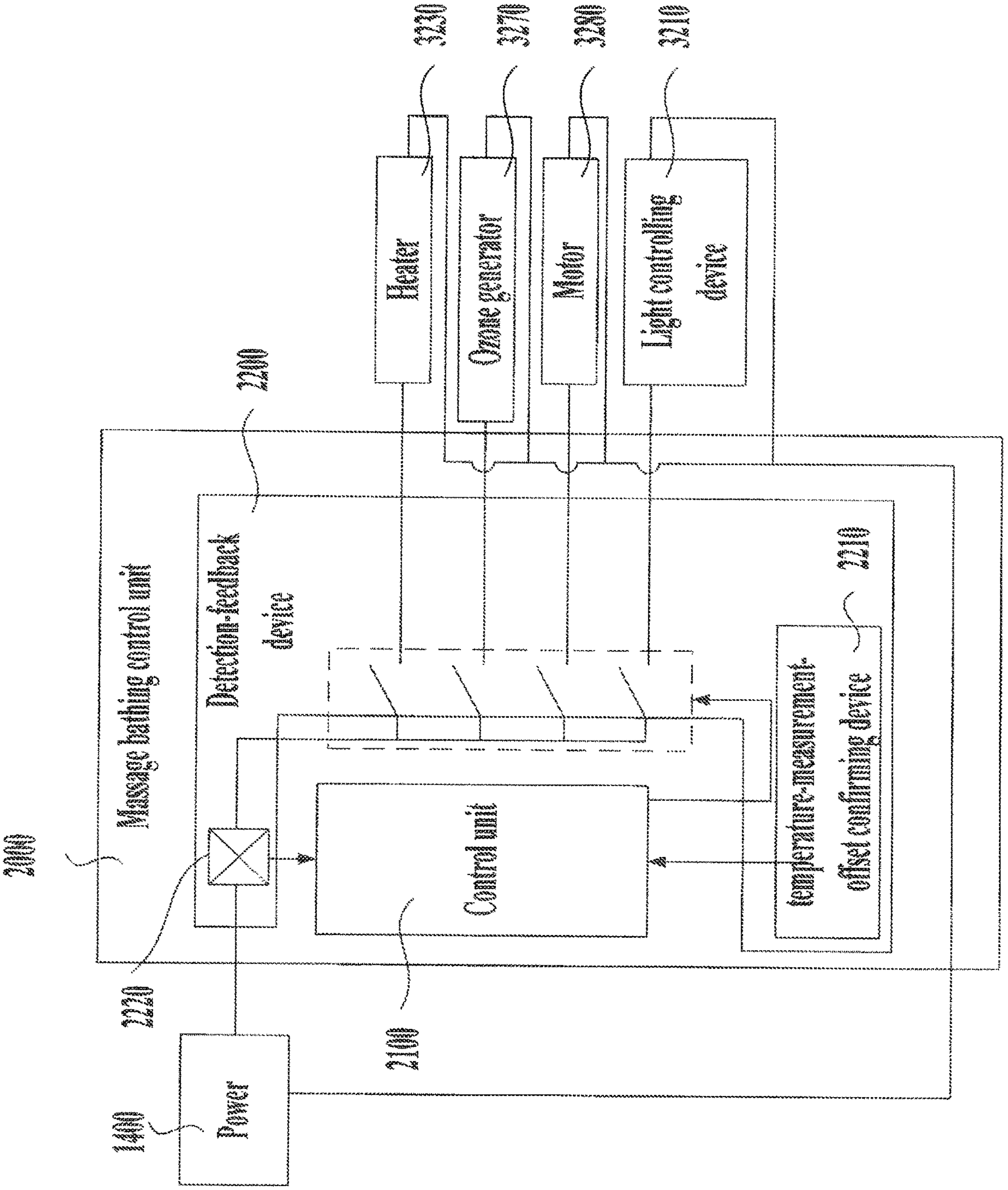
FIG. 13 is an illustrative view of a third composite type of the massage bathing control unit and each of the second attached devices according to the massage bathing maintenance system of FIG. 9.

With reference of FIGS. 9 and 13, FIG. 13 is an illustrative view of a third composite type of the massage bathing control unit 2000 and each of the second attached devices according to the massage bathing maintenance system 400 of FIG. 9. The difference from the first composite type of FIG. 10 is: the detection-feedback device 2200 of the massage bathing control unit 2000 disposes a sensing unit 2220 between the switching units and the power 1400, to detect the specific physical values between the power 1400 of the several second attached devices 3200 (including the heater 3230, the ozone generator 3270, motor 3280, and light controlling device 3210) and the at least one second attached device 3200, and to transmit the specific physical values to the control unit 2100, then the control unit 2100 generates the at least one actuating message according to the detection result (based on the detected specific physical values) and provides the at least one actuating message to the master control device 1000.

Figure 14:
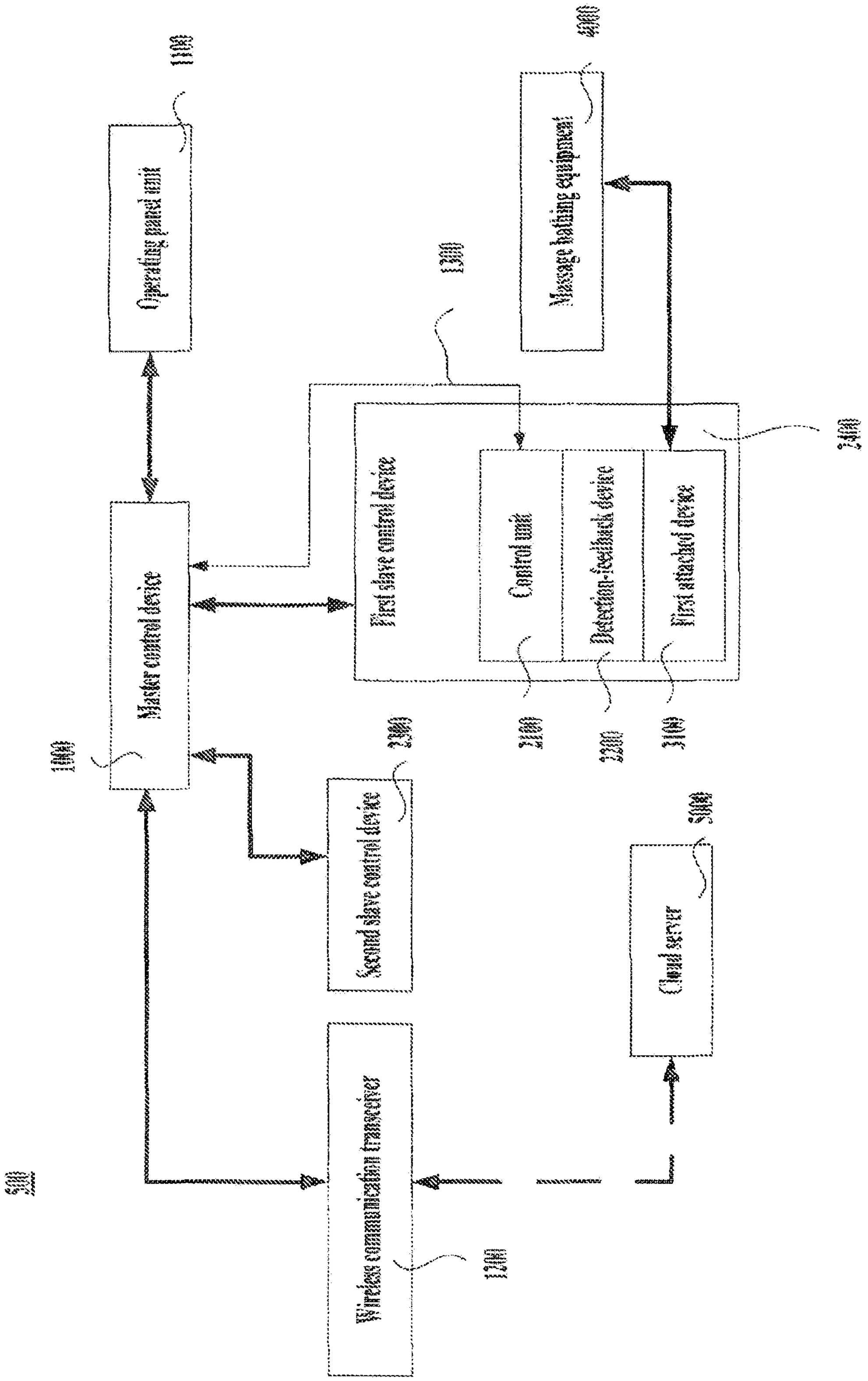
FIG. 14 is an illustrative view of a massage bathing maintenance system according to a fifth preferred embodiment of the present invention.

With reference of FIGS. 9 and 14, FIG. 14 is an illustrative view of a massage bathing maintenance system 500 according to a fifth preferred embodiment of the present invention. The difference between the fifth preferred embodiment and the fourth preferred embodiment of FIG. 9 is: The fifth preferred embodiment disposes no massage bathing control unit and the second attached device, but disposes at least one first slave control device 2400. Each of the at least one first slave control devices comprises a control unit 2100, a detection-feedback device 2200, and at least one first attached device 3100. In the preferred embodiment, each first attached device 3100 (refer to FIG. 6), the control unit 2100, and the detection-feedback device 2200 establish each of the first slave control devices 2400. The control unit 2100 and the detection-feedback device 2200 are the same as the above preferred embodiment, no description is given here.

Figure 15:
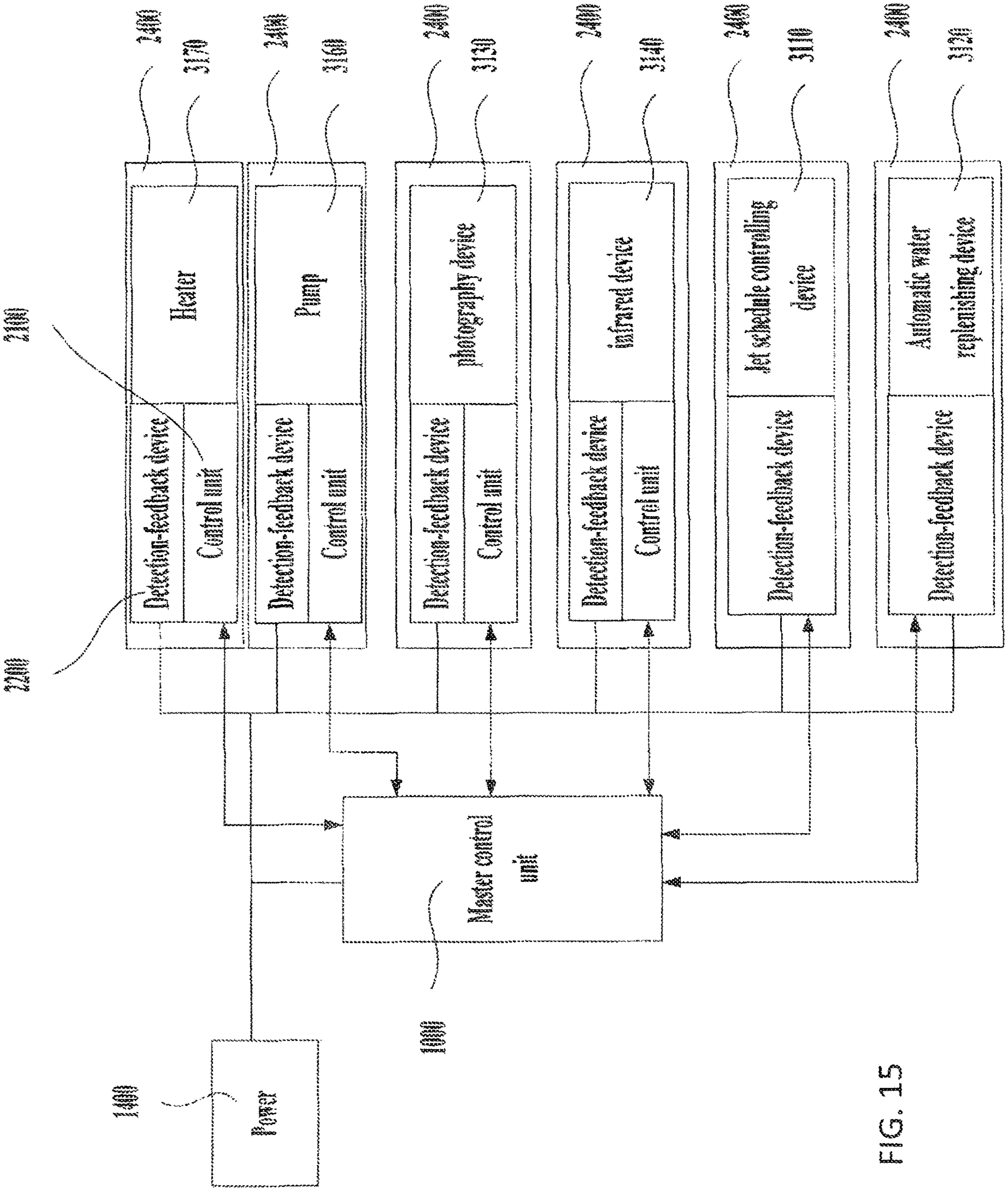
FIG. 15 is a composing view of master control device and the several first slave control devices of the massage bathing maintenance system of FIG. 14.

FIG. 15 is a composite view of master control device 1000 and the several first slave control devices 2400 of the massage bathing maintenance system 500 of FIG. 14. In the composite view, a part of the at least one first attached device 3100 (including the photography device 3130, infrared device 3140, the pump 3160, and the heater 3170) is combined with a detection-feedback device 2200 and a control unit 2100 to establish several first slave control devices 2400, the other of the at least one first attached device 3100 (including the jet schedule controlling device 3110 and the automatic water replenishing device 3120) is built with a control unit, so the other of the at least one first attached devices 3100 only need to be combined with the detection feedback device 2200 to establish several first slave control devices 2400, then electrically connect with the master control device 1000 and the power 1400.

Figure 16:
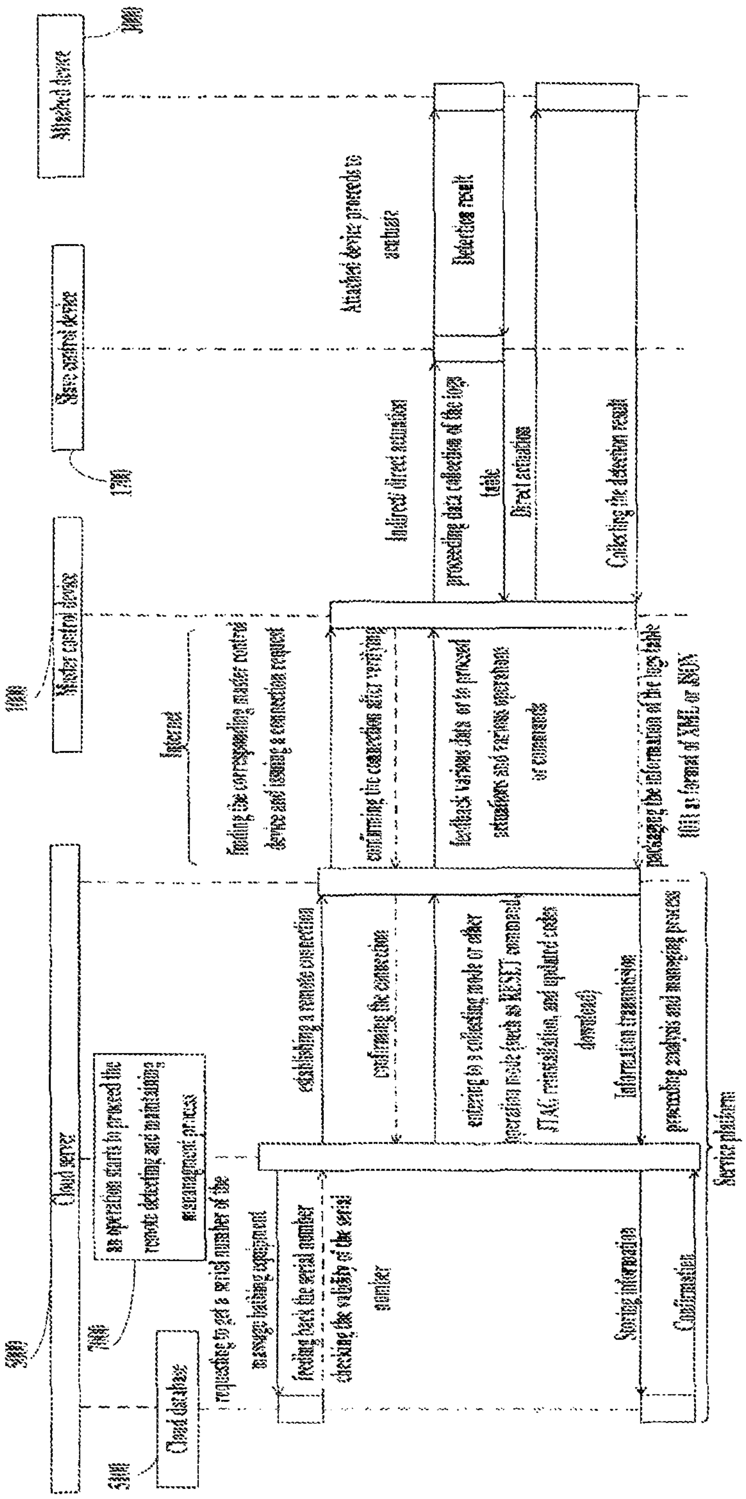
FIG. 16 is a first time domain control diagram of a massage bathing maintenance system of the present invention.
Figure 17:
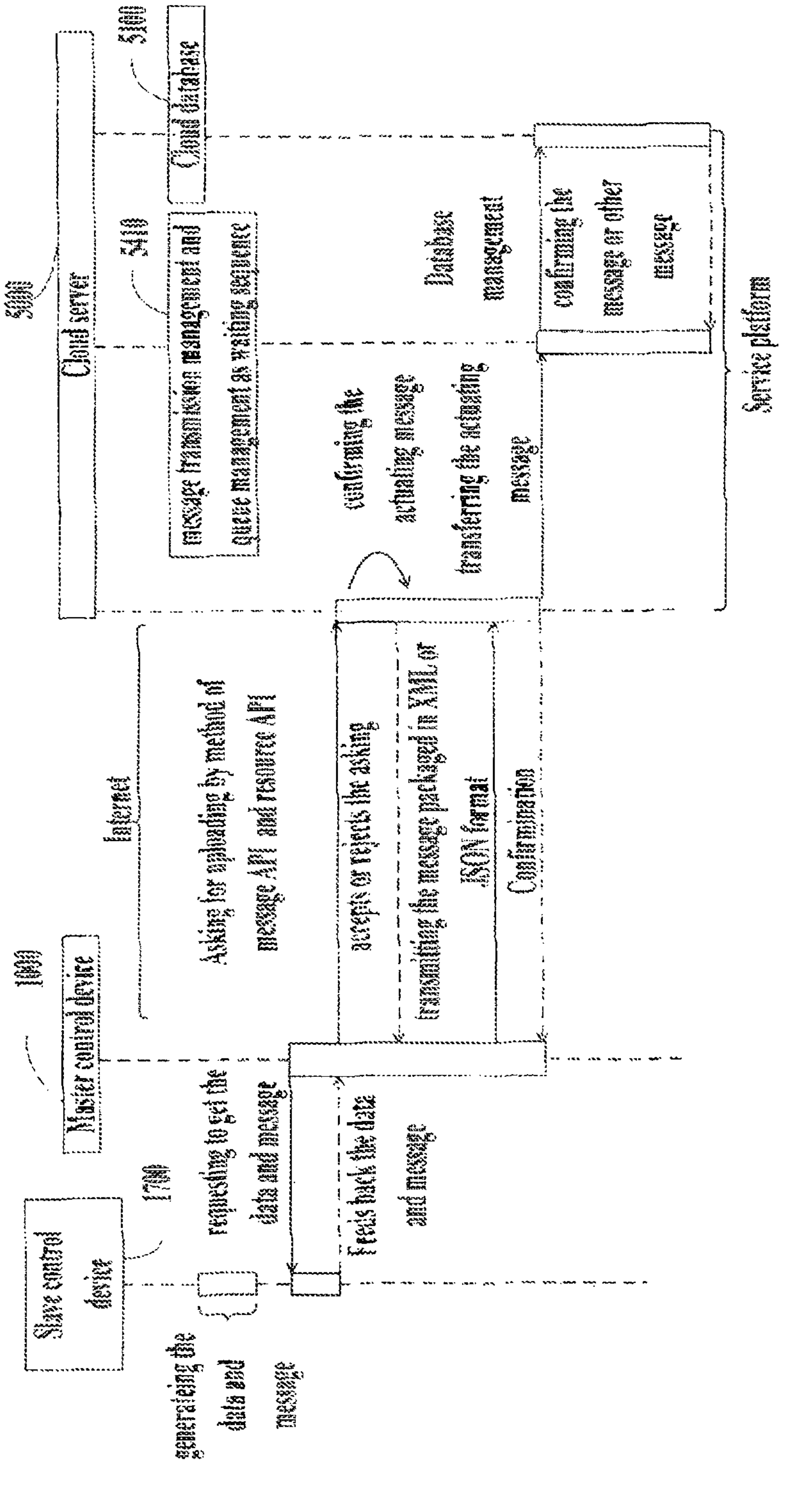
FIG. 17 is a second time domain control diagram of a massage bathing maintenance system of the present invention.

With reference of FIGS. 16 and 17, FIG. 16 is a first time domain control diagram of a massage bathing maintenance system 100, 200, 300, 400, 500 of the present invention. FIG. 17 is a second time domain control diagram of a massage bathing maintenance system 100, 200, 300, 400, 500 of the present invention. In order to easily understand the description of each time domain control diagram, please refer to the numerals of the items drawn in FIGS. 2, 9, and 14. The first time domain control diagram of FIG. 16 and the second time domain control diagram of FIG. 17 represent two kinds of time domain control methods, one kind of method is to activate the remote detecting and maintaining management process via a remote terminal (cloud server 5000), the other is to activate the remote detecting and maintaining management process via a local terminal (master control device 1000).

Referring to FIG. 16, first, while the cloud server 5000 of the remote terminal activates the remote detecting and maintaining management process 7000, an operation starts to proceed the remote detecting and maintaining management process 7000. Then, the remote detecting and maintaining management process 7000 requests the cloud database 5100 for a corresponding serial number of the massage bathing equipment 4000. Then, the serial number of the massage bathing equipment 4000 is feeding back. Then, the remote detecting and maintaining management process 7000 checks the validity of the serial number of the massage bathing equipment 4000. Then, the remote detecting and maintaining management process 7000 establishes a remote connection between the master control device 1000 and the cloud server 5000. Then, the cloud server 5000 finds out the corresponding master control device 1000 and issues a connection request through a network (such as the internet). Then, the connection is confirmed after verification of the master control device 1000. Then, the cloud server 5000 confirms the connection. Then, the remote detecting and maintaining management process 7000 enters a logs-table 1011 collecting mode or other operation mode (such as RESET request, STAG reinstallation, or updated codes download). Then, the cloud server 5000 requests the master control device 1000 to feedback various data of the logs table 1011, or to proceed actuations and various operations or requests. Then, the master control device 1000 controls the at least one slave control device 1700 and the at least one attached device 3000 to proceed direct or indirect operation (such as detection). Then, the slave control device 1700 and the attached device 3000 proceed the operation (such as detection) according to the control request. Then, the attached devices 3000 generate at least one detection result such as data and situation of the detection, and the slave control device 1700 generates the at least one actuating message including the detection result to be data of the logs table 1011. Then, the master control device 1000 receives the at least one actuating message (data of the logs table) to proceed data collection of the logs table 1011. Then, the master control device 1000 packages the information of the logs table 1011 in XML or JSON format. Then, the cloud server 5000 proceeds the information transmission of the logs table 1011. Then, the information of the logs table 1011 is stored in the cloud server 5000. Then, the cloud server 5000 proceeds the verification. Then, the analyzing unit 5510 proceeds an analysis and managing process of the logs table 1011.

FIG. 17 illustrates that while the cloud server 5000 of the local terminal activates the remote detecting and maintaining management process 7000, first, the slave control device 1700 generates the data and message (such as the at least one actuating message including the at least one detection result) of the logs table. The at least one actuating message includes the at least one detection result comprising records and daily detection records generated by the FIG. 19. Then, the master control device 1000 requests the slave control device 1700 to provide data and message of the logs table. Then, the slave control device 1700 feeds back the data and message of the logs table. Then, the master control device 100 requests the cloud server 5000 for the service of uploading the logs table through the internet, by the methods of message API (Application Programming Interface) and resource API. Then, the cloud server 5000 confirms the actuating message. Then, the cloud server 5000 accepts or rejects the asking. Then, the master control device 1000 transmits the message packaged in XML or JSON format (the same as the logs table). Then, the cloud server 5000 confirms the actuating message, to transfer the message into message transmission management and queue management 5410 as a waiting sequence. Then, the cloud database 5100 proceeds database management. Then, the cloud database 5100 proceeds to confirm the message or other messages.

Figure 18:
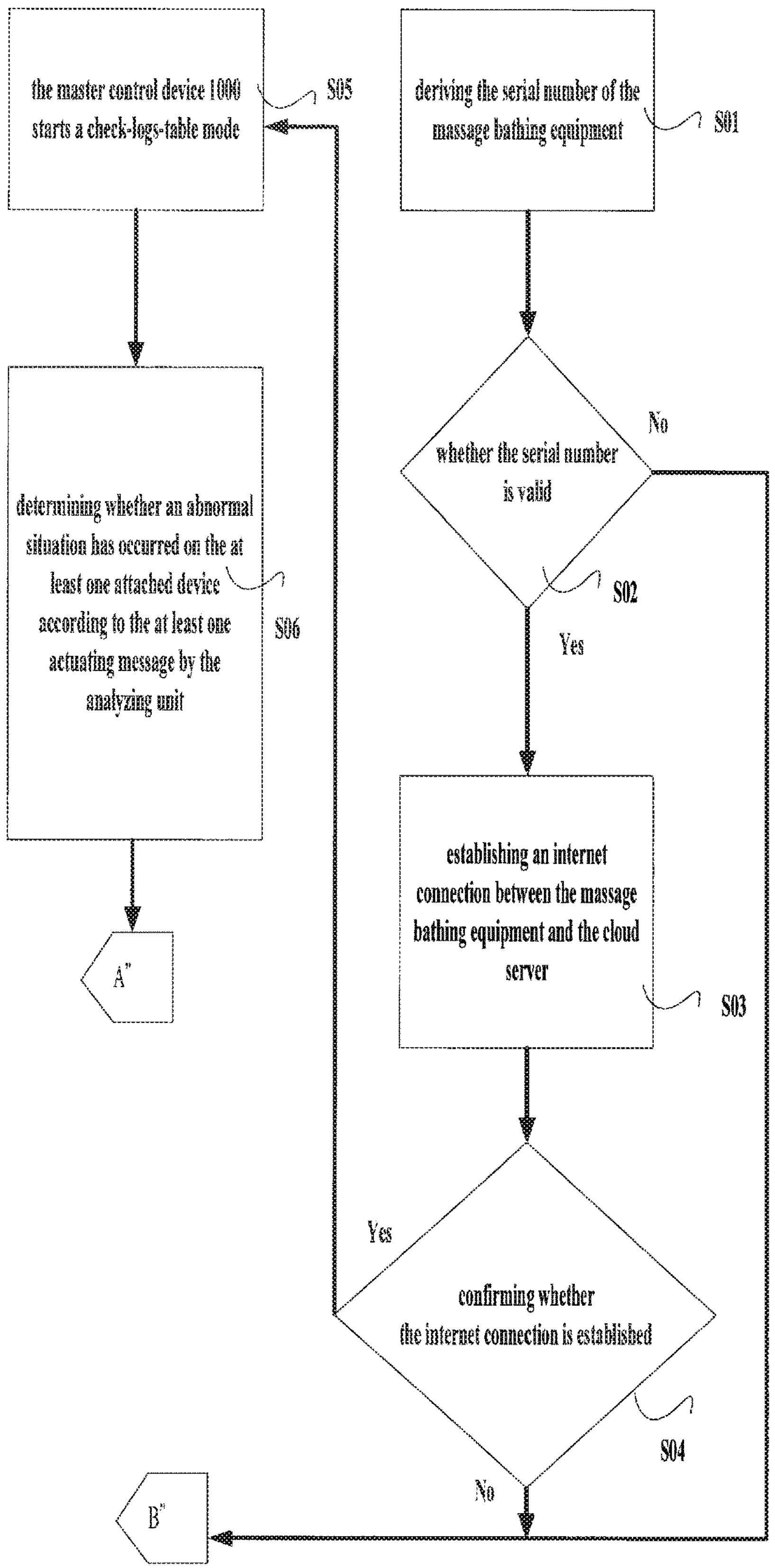
FIG. 18 is a flow diagram of a massage bathing maintenance method of a massage bathing maintenance system of the present invention.
Figure 18:
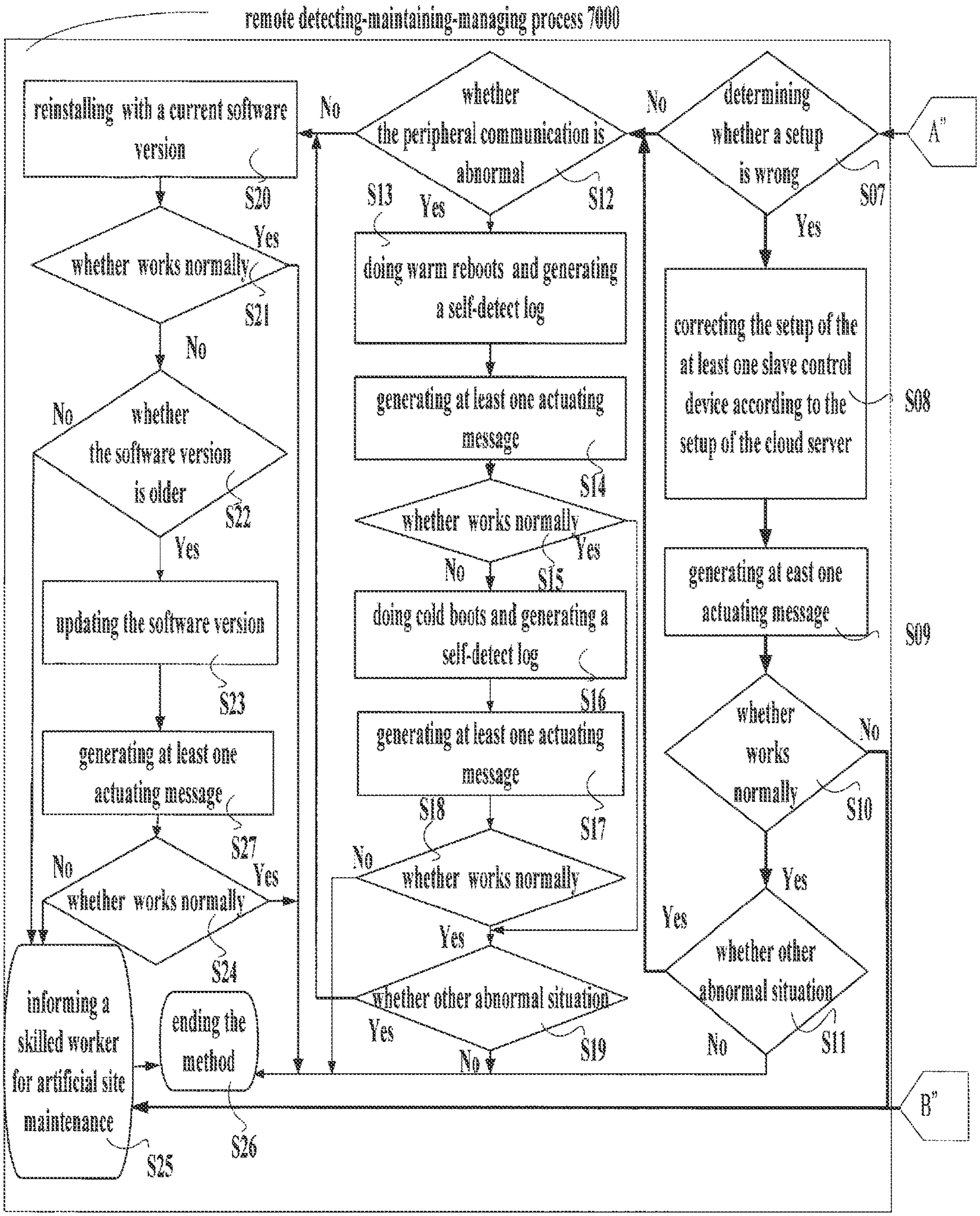

FIG. 18 is a flow diagram of a massage bathing maintenance method of a massage bathing maintenance system of the present invention. In step S01, deriving the serial number of the massage bathing equipment 4000. Then, in step S02, determining whether the serial number is valid. In step S02, if no, then proceeding to step S25, informing a skilled worker for artificial site maintenance. In step S02, if yes, then proceeding to step S03, establishing an Internet connection between the massage bathing equipment 4000 and the cloud server 5000. Then, step S04, confirming whether the internet connection is established. In step S04, if no, then step proceeding to S25, informing the skilled worker for artificial site maintenance. In step S04, if yes, then proceeding to step S05, the master control device 1000 starts a check-logs-table mode. Then, step S06, determining whether an abnormal situation has occurred on the at least one attached device 3000 according to the at least one detecting message by the analyzing unit 5510. Then, step S07, determining whether a setup is wrong on the at least one slave control device 1700. In step S07, if no, then proceeding to step S12, determining whether a peripheral communication is abnormal. In step S07, if yes, then proceeding to step S08, correcting the setup of the at least one slave control device 1700 according to the setup of the cloud server 5000. Then, step S09, generating at least one actuating message. Then, step S10, determining whether the at least one slave control device 1700 works normally. In step S10, if no, then proceeding to step S25, informing the skilled worker for artificial site maintenance. In step S10, if yes, then proceeding to step S11, determining whether there is another abnormal situation. In step S11, if no, then proceeding to step S26, ending the method. In step S11, if yes, then proceeding to step S12, determining whether the peripheral communication is abnormal. In step S12, if no, then proceeding to step S20, reinstalling the at least one slave control device 1700 with a current software version. In step S12, if yes, then proceeding to step S13, doing warm reboots request and generating a self-detect log. Then, step S14, generating at least one actuating message. Then, step S15, determining whether the at least one slave control device 1700 works normally. In step S15, if yes, then proceeding to step S19, determining whether there is another abnormal situation. In step S15, if no, then proceeding to step S16, doing cold reboots request and generating a self-detect log. Then, step S17, generating at least one actuating message. Then, step S18, determining whether the at least one slave control device 1700 works normally. In step S18, if no, then proceeding to step S25, informing the skilled worker for artificial site maintenance. In step S18, if yes, then proceeding to step S19, determining whether there is another abnormal situation. In step S19, if no, then proceeding to step S26, ending the method. In step S19, if yes, then proceeding to step S20, reinstalling the at least one slave control device 1700 with a current software version. Then, step S21, determining whether the at least one slave control device 1700 works normally. In step S21, if yes, then proceeding to step S26, ending the method. In step S21, if no, then proceeding to step S22, confirming whether the software version of the at least one slave control device 1700 is older. In step S22, if no, then proceeding to step S25, informing the skilled worker for artificial site maintenance. In step S22, if yes, then proceeding to step S23, updating the software version of the at least one slave control device 1700. Then, step S27, at least one slave control device generating at least one actuating message. Then, step S24, determining whether the at least one slave control device 1700 works normally. In step 24, if yes, then proceeding to step S26, ending the method. In step 24, if no, then proceeding to step S25, informing the skilled worker for artificial site maintenance. Steps S07-S27 are the remote detecting and maintaining management process.

Figure 19:
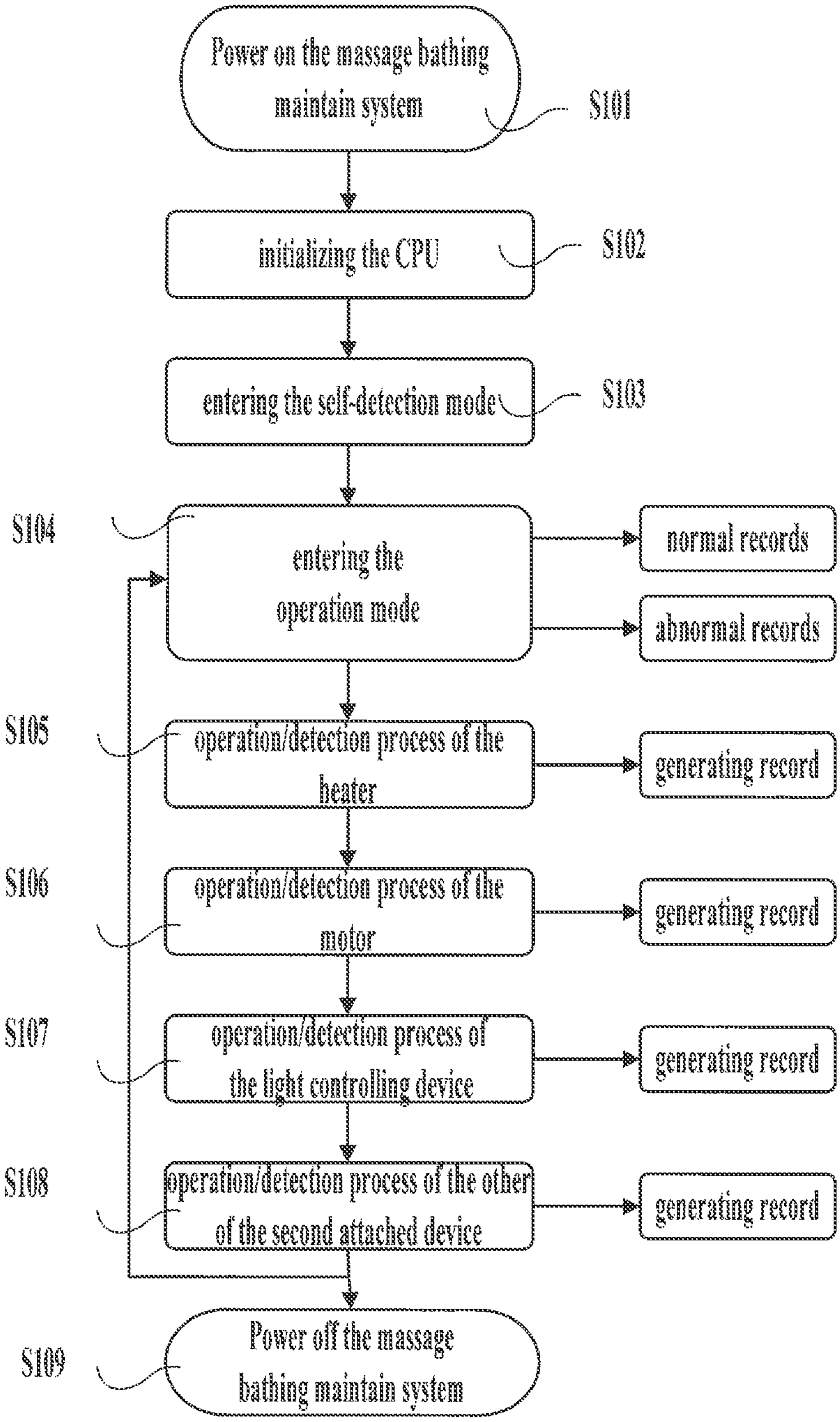
FIG. 19 is a flow diagram of an detection method of a massage bathing maintenance system of the present invention.

FIG. 19 is a flow diagram of an detection method of a massage bathing maintenance system of the present invention. First, step S101, turn-on the massage bathing maintenance system. Then, step S102, initializing the CPU (Central Processing Unit). Then, step S103, entering self-detection mode. Then, step S104, entering operation mode and generating normal records and abnormal records. Then, Step S105, actuating the operation/detection process of the heater and recording. Then, step S106, actuating the operation/detection process of the motor and recording. Then, step 3107, actuating the operation/detection process of the light controlling device and generating record. Then, step 3108, actuating the operation/detection process of the other of the second attached device and recording. Then, if the massage bathing maintenance system continues to be used, then repeat to step S104, if the massage bathing maintenance system stops being used, then proceeding to step S109, power off the massage bathing maintenance system.

Figure 20:
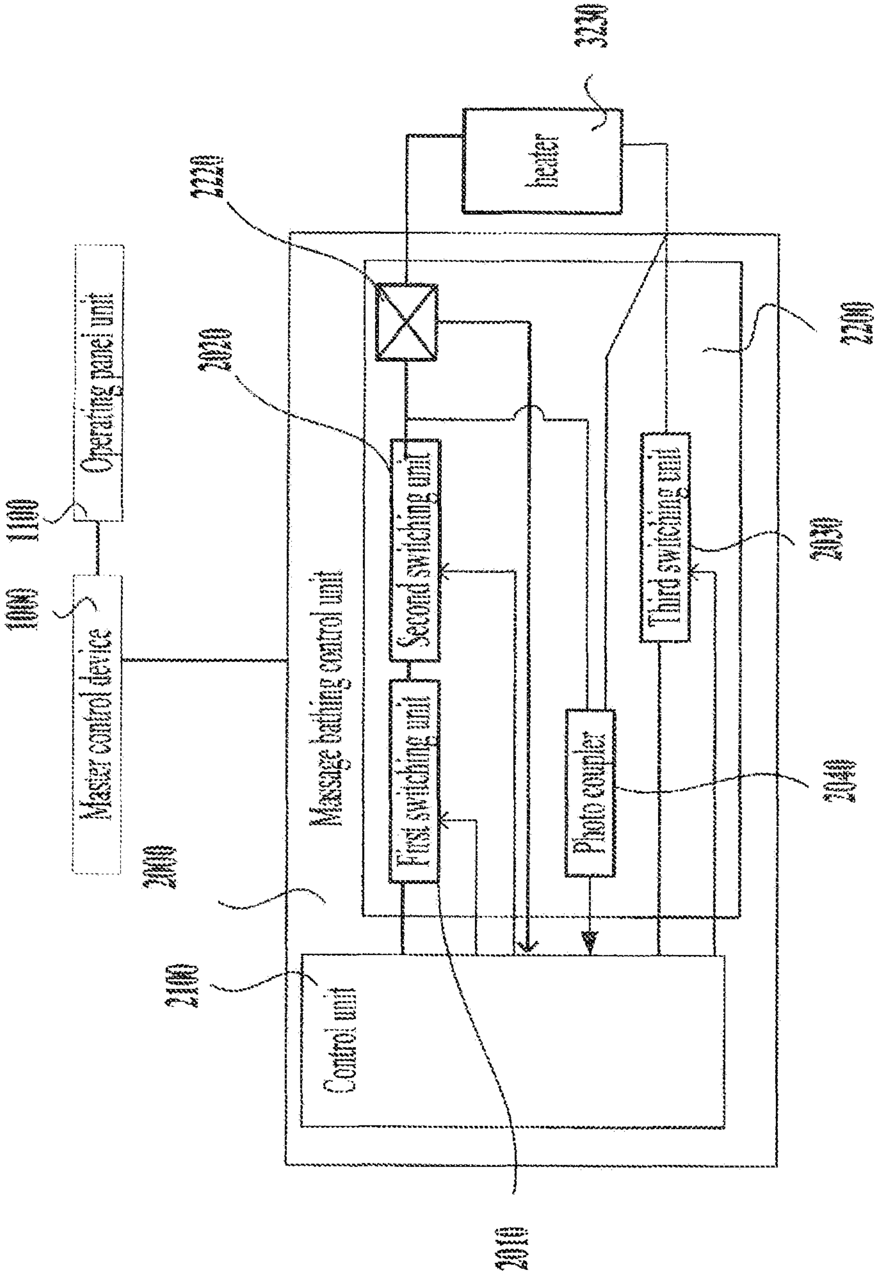
FIG. 20 is a first composing view of the massage bathing control unit of a massage bathing maintenance system of the present invention.

FIG. 20 is a first composite view of the massage bathing control unit of a massage bathing maintenance system of the present invention. In the composite view, the detection-feedback device 2200 comprises at least one switching unit and at least one sensing unit 2220. In the invention, the at least one switching unit comprises a first switching unit 2010, a second switching unit 2020, and a third switching unit 2030; the switching units 2010, 2020, 2030 can be relays. The at least one sensing unit 2220 comprises two sensing units 2220 (a first sensing unit 2220 and a second sensing unit 2220), the second sensing unit 2220 is a photo coupler. The composite takes the heater 3230 for an example. The control unit 2100 connects to the first switching unit 2010, the first switching unit 2010 connects to the second switching unit 2020, the second switching unit 2020 connects to a first terminal of the first sensing unit 2220, a second terminal of the first sensing unit 2220 connects to the control unit 2100, a third terminal of the first sensing unit 2220 connects to a first terminal of the second attached device 3200 (heater 3230), a second terminal of the second attached device 3200 connects to the third switching unit 2030, and the third switching unit 2030 connects to the control unit 2100. A first terminal of the photo coupler 2220 connects to the control unit 2100, a second terminal of the photo coupler 2220 connects to the first terminal of the first sensing unit 2220, and a third terminal of the photo coupler 2220 connects to the second terminal of the second attached device 3200.

Figure 21:
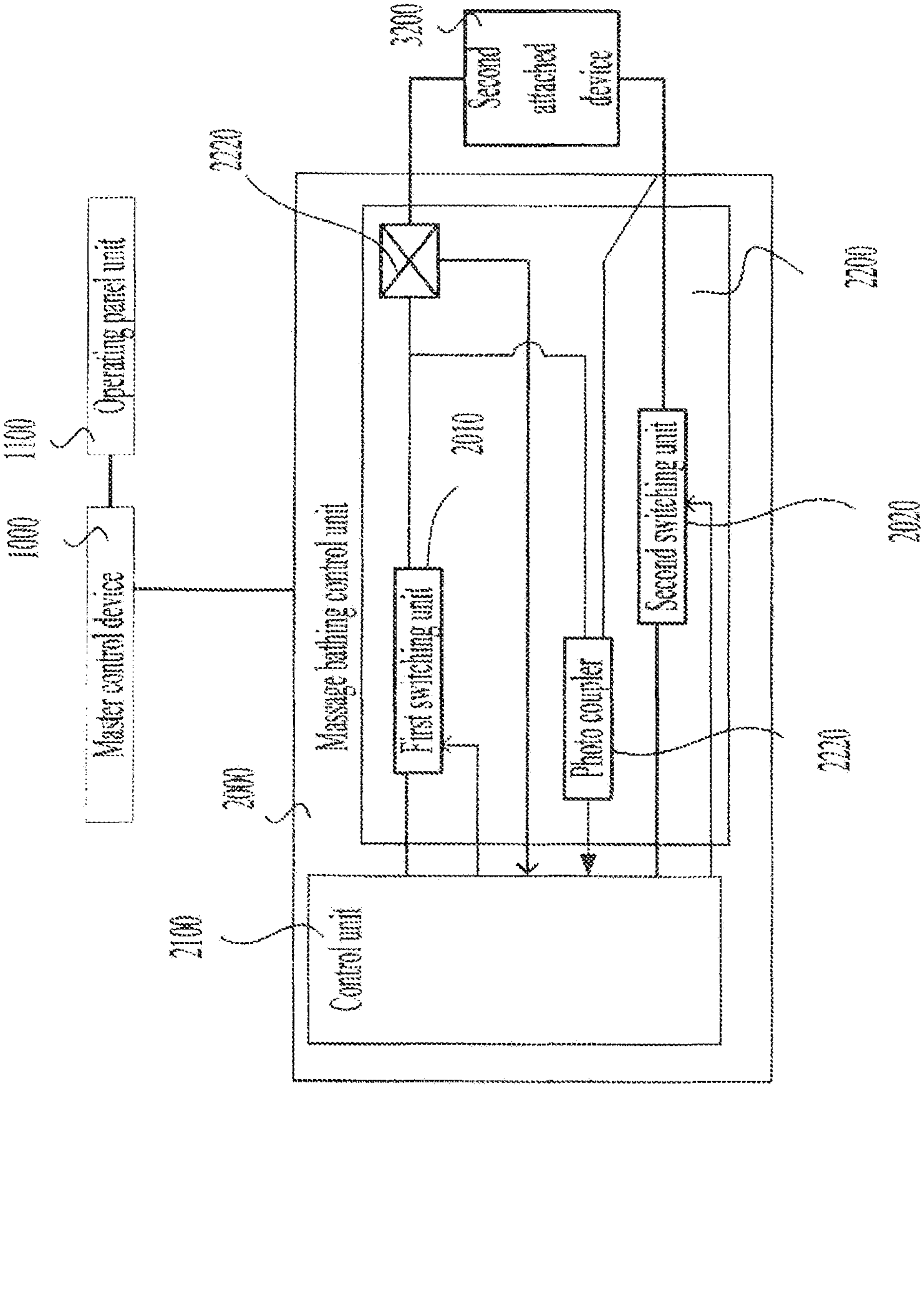
FIG. 21 is a second composing view of the massage bathing control unit of a massage bathing maintenance system of the present invention.

FIG. 21 is a second composing view of the massage bathing control unit of a massage bathing maintenance system of the present invention. The difference between the second composing and the first composing of FIG. 20 is: the second composing lacks the third switching unit 2030 and changes the wiring method. The control unit 2100 connects to the first switching unit 2010, the first switching unit 2010 connects to a first terminal of the first sensing unit 2220, a second terminal of the first sensing unit 2220 connects to the control unit 2100, a third terminal of the first sensing unit 2220 connects to a first terminal of the second attached device 3200, a second terminal of the second attached device 3200 connects to the second switching unit 2020, the second switching unit 2020 connects to the control unit 2100. A first terminal of the photo coupler 2220 connects to the control unit 2100, a second terminal of the photo coupler 2220 connects to the first terminal of the first sensing unit 2220, a third terminal of the photo coupler 2220 connects to the second terminal of the second attached device 3200.

Figure 22:
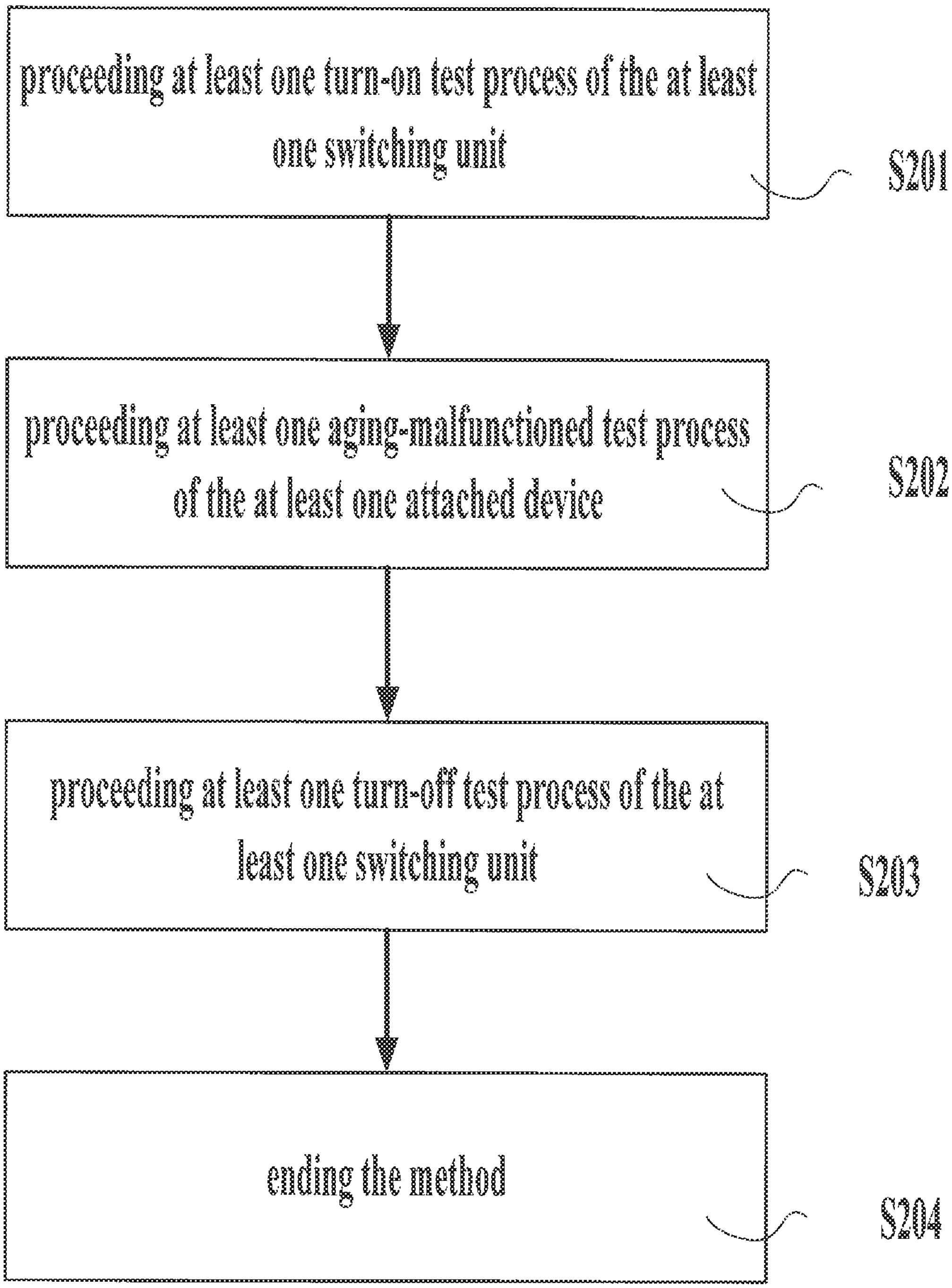
FIG. 22 is a rough flow diagram of a self-detection method of the massage bathing maintenance system according to one embodiment of the present invention.

FIG. 22 is a rough flow diagram of a self-detection method of the massage bathing maintenance system according to one embodiment of the present invention. First, step 3201, proceeding at least one turn-on test process of the at least one switching unit. Then, step S202, proceeding at least one aging-malfunctioned test process of the at least one attached device. Then, Step S203, proceeding at least one turn-off test process of the at least one switching unit. Finally, step 3204, ending the method.

Figure 23:
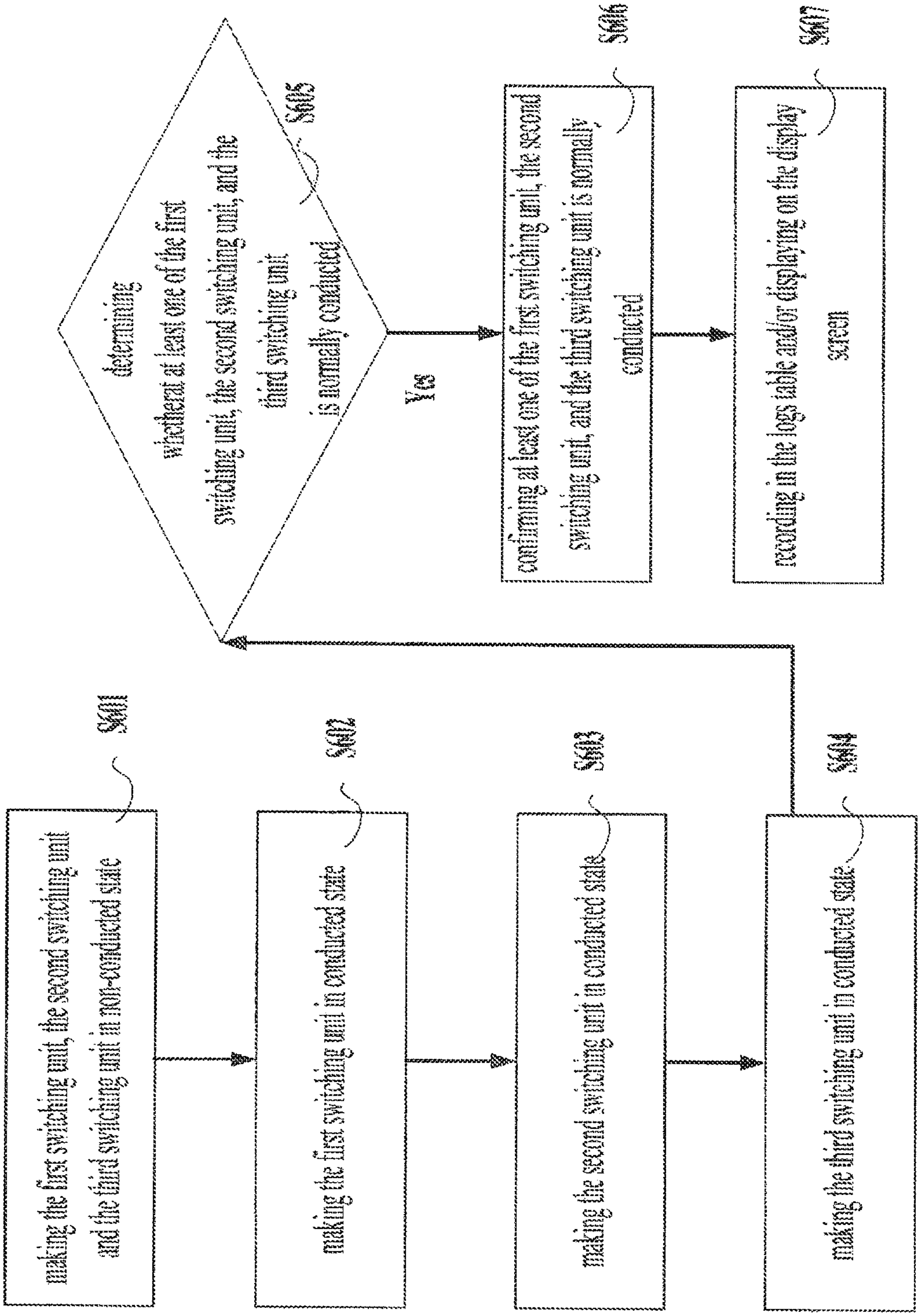
FIG. 23 is a detailed flow diagram while using three switching units of the step S201 of FIG. 22.

FIG. 23 is a detailed flow diagram while using three switching units in the step S201 of FIG. 22. In the flow diagram, a detailed description to the turn-on test process of using three switching units is made. First, Step 3801, making the first switching unit, the second switching unit and the third switching unit in non-conducted state. Then, step S602, making the first switching unit in conducted state. Then, step 3603, making the second switching unit in conducted state. Then, step S604, making the third switching unit in conducted state. Then, step S605, determining whether at least one of the first switching unit, the second switching unit, and the third switching unit is normally conducted. In step 3605, if yes, then step 3606, confirming at least one of the first switching unit, the second switching unit, and the third switching unit is normally conducted. Then, step S607, recording in the logs table 1011 and/or displaying on the display screen 1110. A sequence of steps 602-604 is able to change according to demands. In step S605, if no, indicating the at least one attached device 3000 and/or the massage bathing control unit 2000 needs to be exchanged, and generating the at least one actuating message for recording in the logs table 1011 and/or displaying on the display screen 1110.

Figure 24:
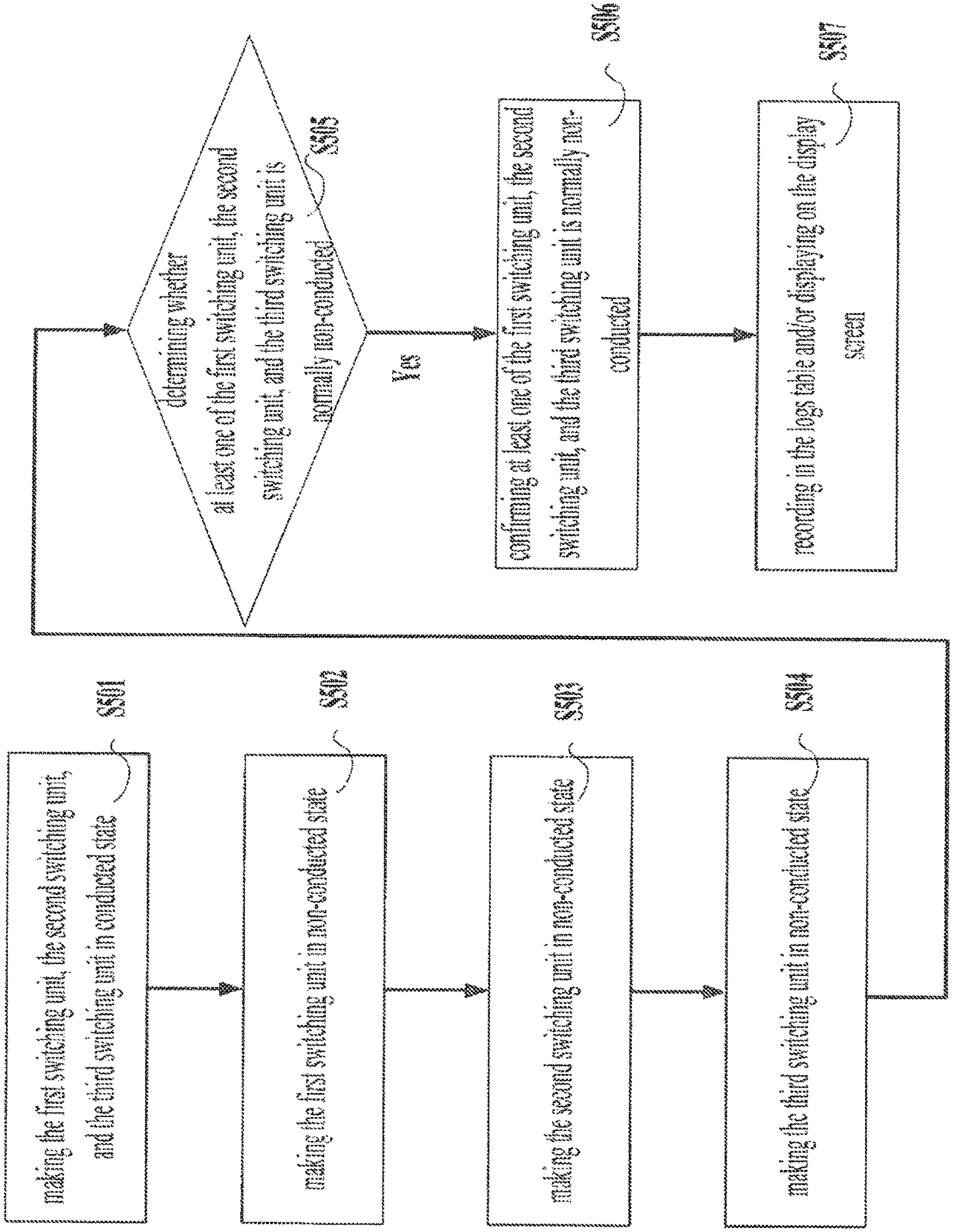
FIG. 24 is a detailed flow diagram while using three switching units of the step 3203 of FIG. 22.

FIG. 24 is a detailed flow diagram while using three switching units in the step S203 of FIG. 22. In the flow diagram, a detailed description of the turn-off test process of using three switching units is made. First, Step S501, making the first switching unit, the second switching unit, and the third switching unit in conducted state. Then, step S502, making the first switching unit in non-conducted state. Then, step S503, making the second switching unit in non-conducted state. Then, step S504, making the third switching unit in non-conducted state. Then, step S505, determining whether at least one of the first switching unit, the second switching unit, and the third switching unit is normally non-conducted. In step S505, if yes, then step 3506, confirming at least one of the first switching unit, the second switching unit, and the third switching unit is normally non-conducted. Then, step S507, recording in the logs table 1011 and/or displaying on the display screen 1110. A sequence of steps 502-504 is able to change according to demands. In step S505, if no, indicating the at least one attached device 3000 and/or the massage bathing control unit 2000 needs to be exchanged, and generating the at least one detecting message for recording in the logs table 1011 and/or displaying on the display screen 1110.

Figure 25:
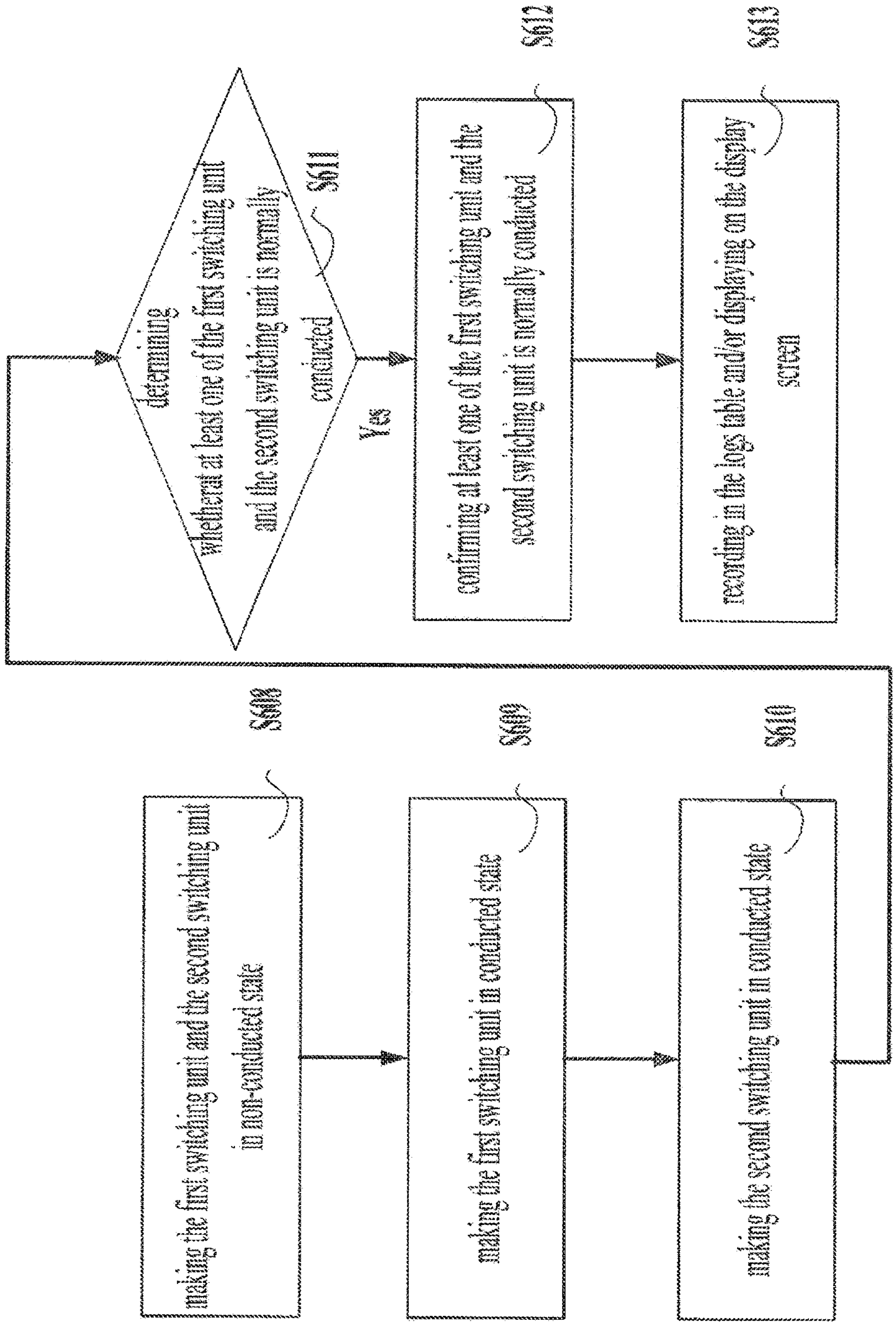
FIG. 25 is a detailed flow diagram while using two switching units of the step S201 of FIG. 22.

FIG. 25 is a detailed flow diagram while using two switching units in the step S201 of FIG. 22. In the flow diagram, a detailed description of the turn-on test process of using two switching units is made. First, Step S608, making the first switching unit and the second switching unit in non-conducted state. Then, step S609, making the first switching unit in conducted state. Then, step S610, making the second switching unit in conducted state. Then, step S611, determining whether at least one of the first switching unit and the second switching unit is normally conducted. In step 3611, if yes, then proceeding to step S612, confirming at least one of the first switching unit and the second switching unit is normally conducted. Then, step S613, recording in the logs table 1011 and/or displaying on the display screen 1110. A sequence of steps 609-610 is able to change according to demands. In step 3611, if no, indicating the at least one attached device 3000 and/or the massage bathing control unit 2000 needs to be exchanged, and generating the at least one detecting message for recording in the logs table 1011 and/or displaying on the display screen 1110.

Figure 26:
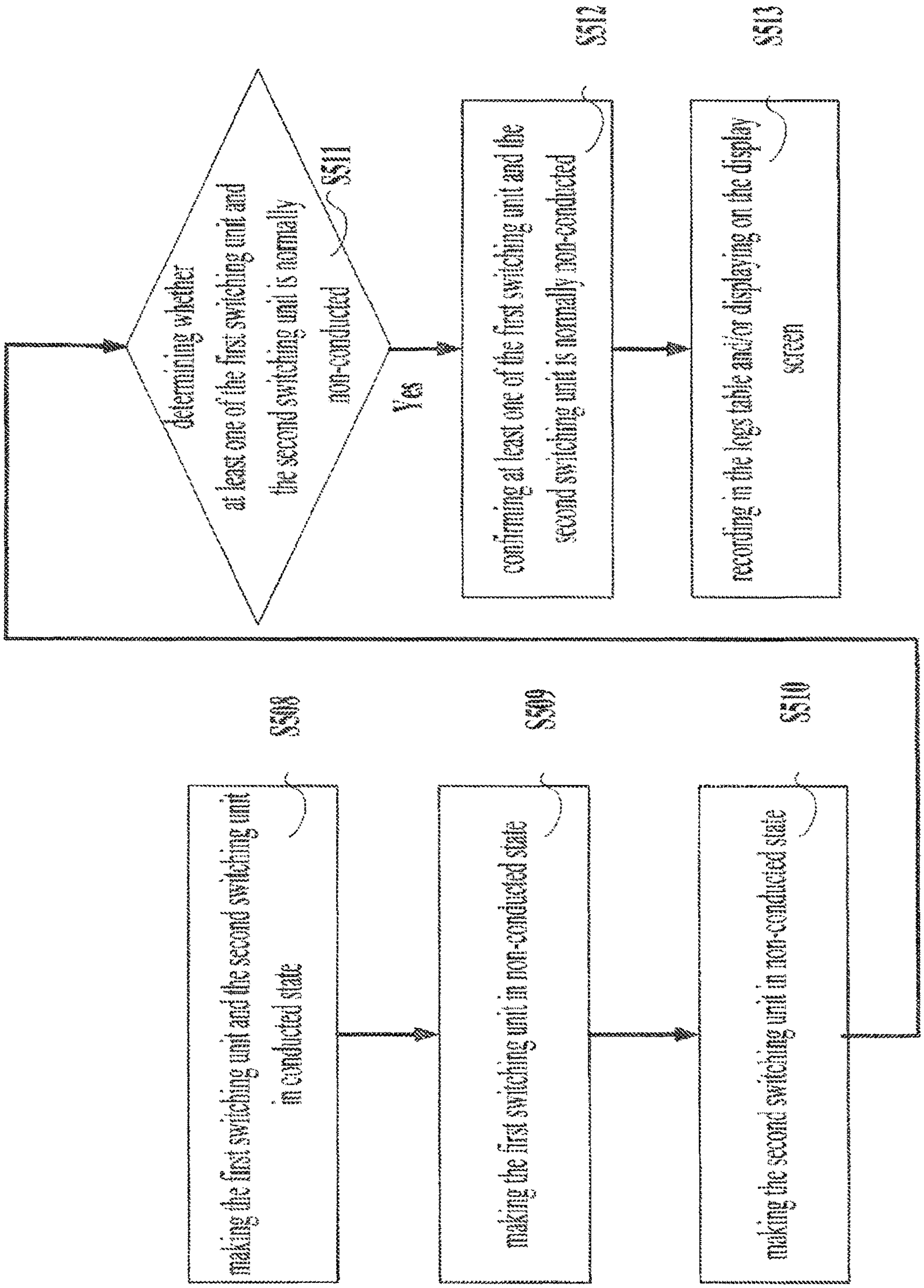
FIG. 26 is a detailed flow diagram while using two switching units of the step S203 of FIG. 22.

FIG. 26 is a detailed flow diagram while using two switching units in the step S203 of FIG. 22. In the flow diagram, a detailed description to the turn-off test process of using two switching units is made. First, Step S508, making the first switching unit and the second switching unit in conducted state. Then, step S509, making the first switching unit in non-conducted state. Then, step 3510, making the second switching unit in non-conducted state. Then, step S511, determining whether at least one of the first switching unit and the second switching unit is normally non-conducted. In step S511, if yes, then proceeding to step 3512, confirming at least one of the first switching unit and the second switching unit is normally non-conducted. Then, step S513, recording in the logs table 1011 and/or displaying on the display screen 1110. A sequence of steps 509-510 is able to change according to demands. In step S511, if no, indicating the at least one attached device 3000 and/or the massage bathing control unit 2000 needs to be exchanged, and generating the at least one detecting message for recording in the logs table 1011 and/or displaying on the display screen 1110.

Figure 27:
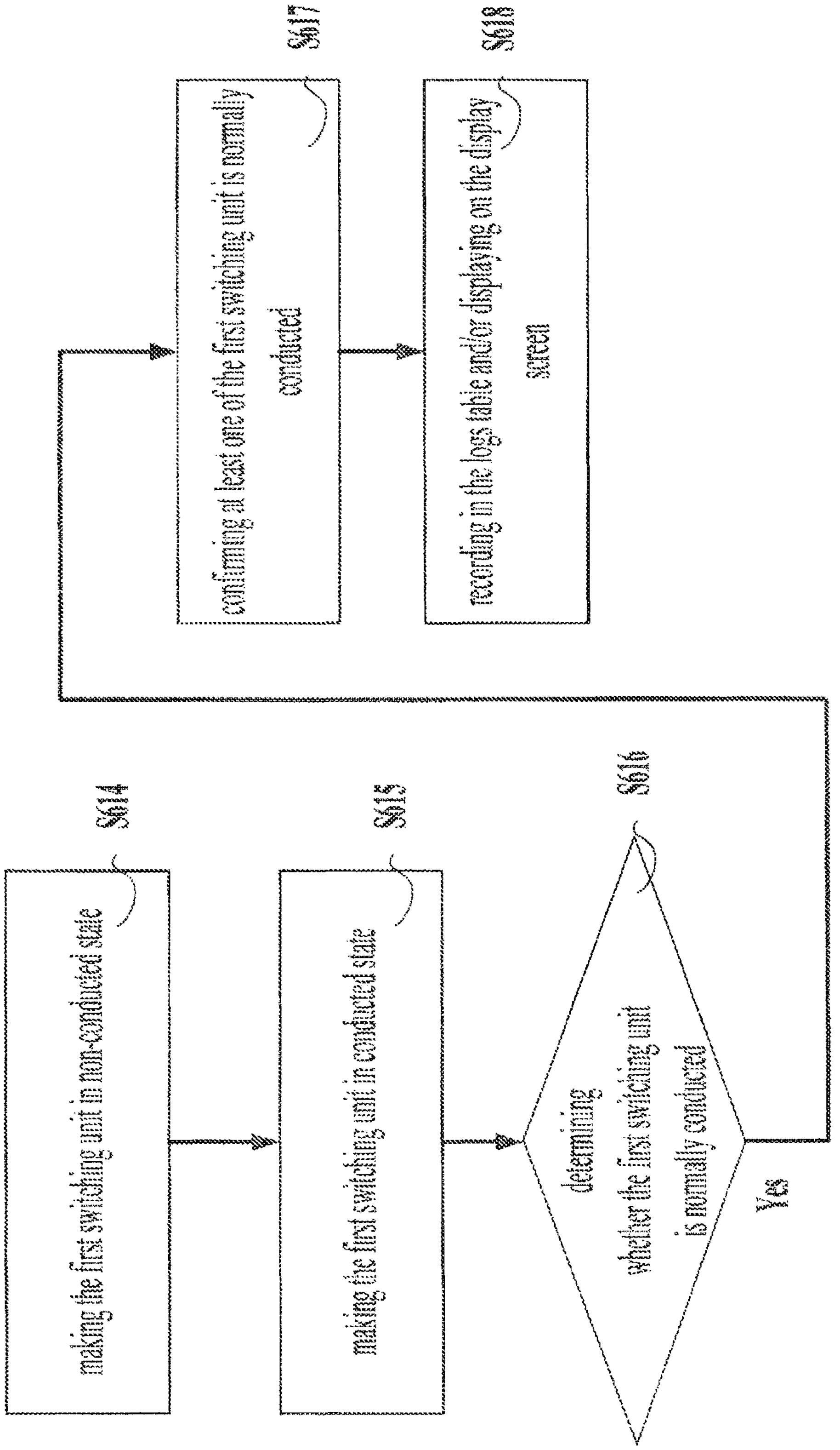
FIG. 27 is a detailed flow diagram while using one switching units of the step 3201 of FIG. 22.

FIG. 27 is a detailed flow diagram while using one switching units in the step 3201 of FIG. 22. In the flow diagram, a detailed description of the turn-on test process of using one switching units is made, First, step 3614, making the first switching unit in non-conducted state. Then, step S615, making the first switching unit in conducted state. Then, step S616, determining whether the first switching unit is normally conducted. In step S616, if yes, then proceeding to step 3617, confirming the first switching unit is normally conducted. Then, step S618, recording in the logs table 1011 and/or displaying on the display screen 1110. In step 3616, if no, indicating the at least one attached device 3000 and/or the massage bathing control unit 2000 needs to be exchanged, and generating the at least one detecting message for recording in the logs table 1011 and/or displaying on the display screen 1110.

Figure 28:
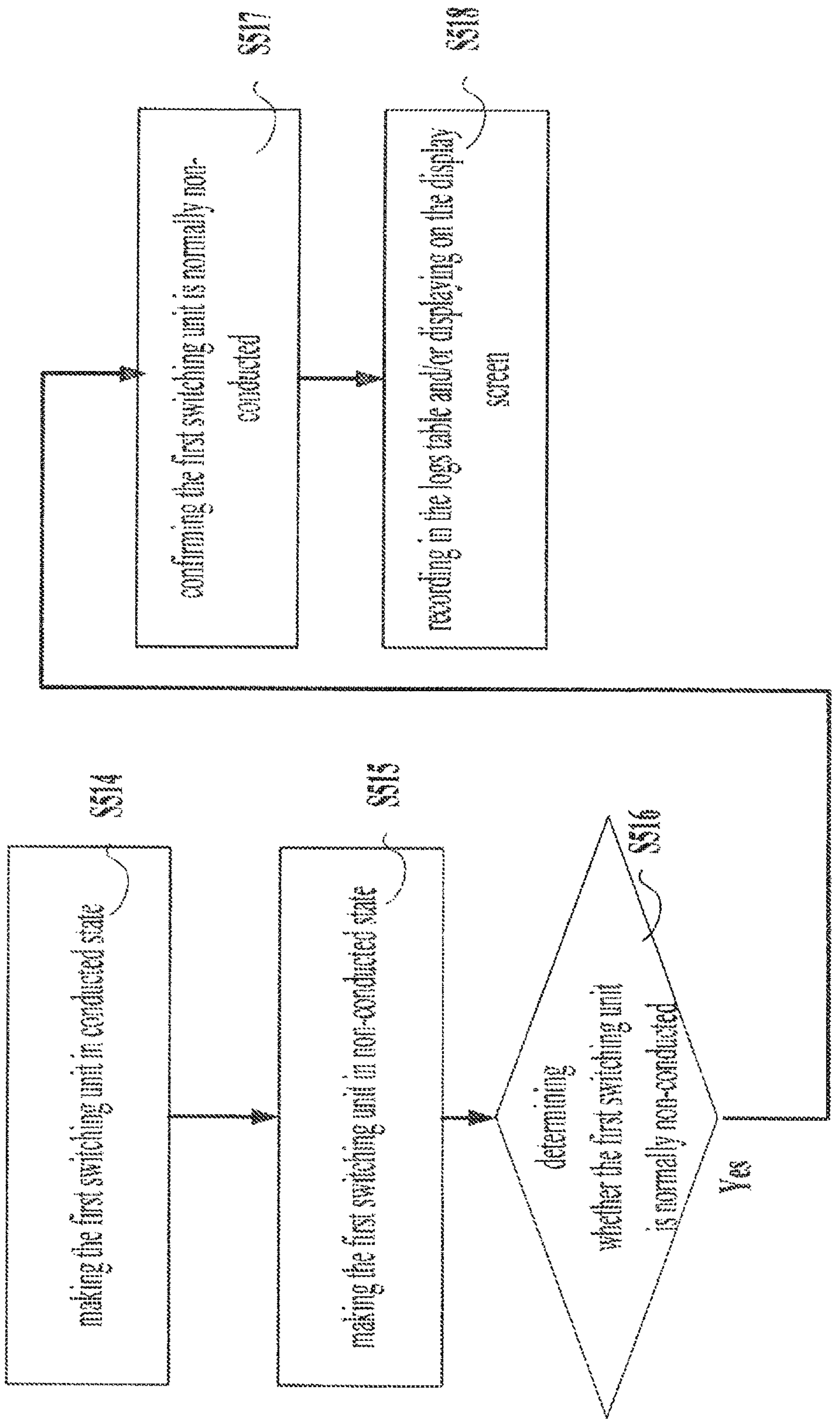
FIG. 28 is a detailed flow diagram while using one switching units of the step S203 of FIG. 22.

FIG. 28 is a detailed flow diagram while using one switching units in the step S203 of FIG. 22, In the flow diagram, a detailed description of the turn-off test process of using one switching units is made, First, Step 3514, making the first switching unit in conducted state. Then, step S515, making the first switching unit in non-conducted state. Then, step S516, determining whether the first switching unit is normally non-conducted. In step S516, if yes, then proceeding to step 3517, confirming the first switching unit is normally non-conducted. Then, step S518, recording in the logs table 1011 and/or displaying on the display screen 1110. In step S516, if no, indicating the at least one attached device 3000 and/or the massage bathing control unit 2000 needs to be exchanged, and generating the at least one detecting message for recording in the logs table 1011 and/or displaying on the display screen 1110.

Figure 29:
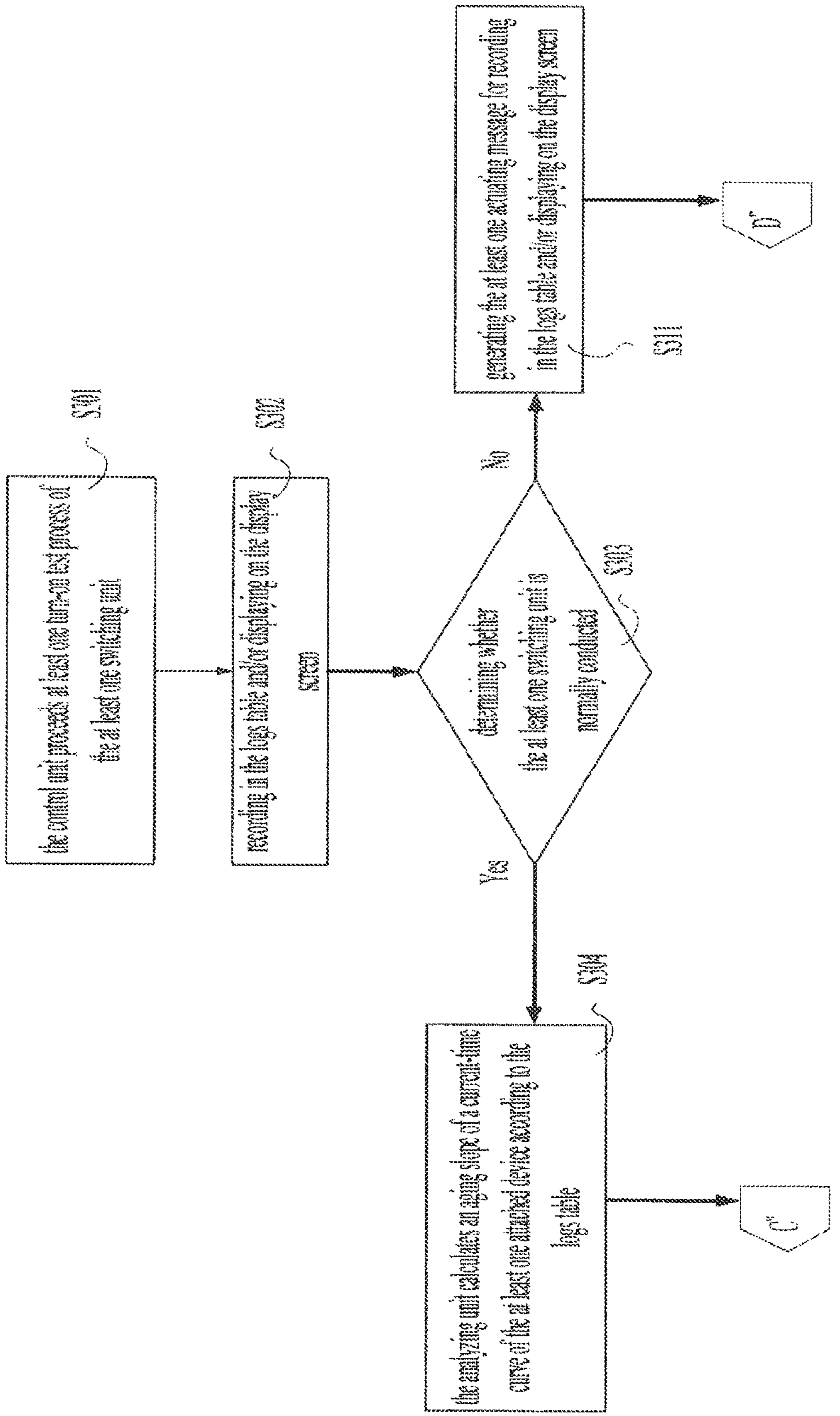
FIG. 29 is a detailed flow diagram of a self-detection method of the massage bathing maintenance system according to one embodiment of the present invention.
Figure 29:
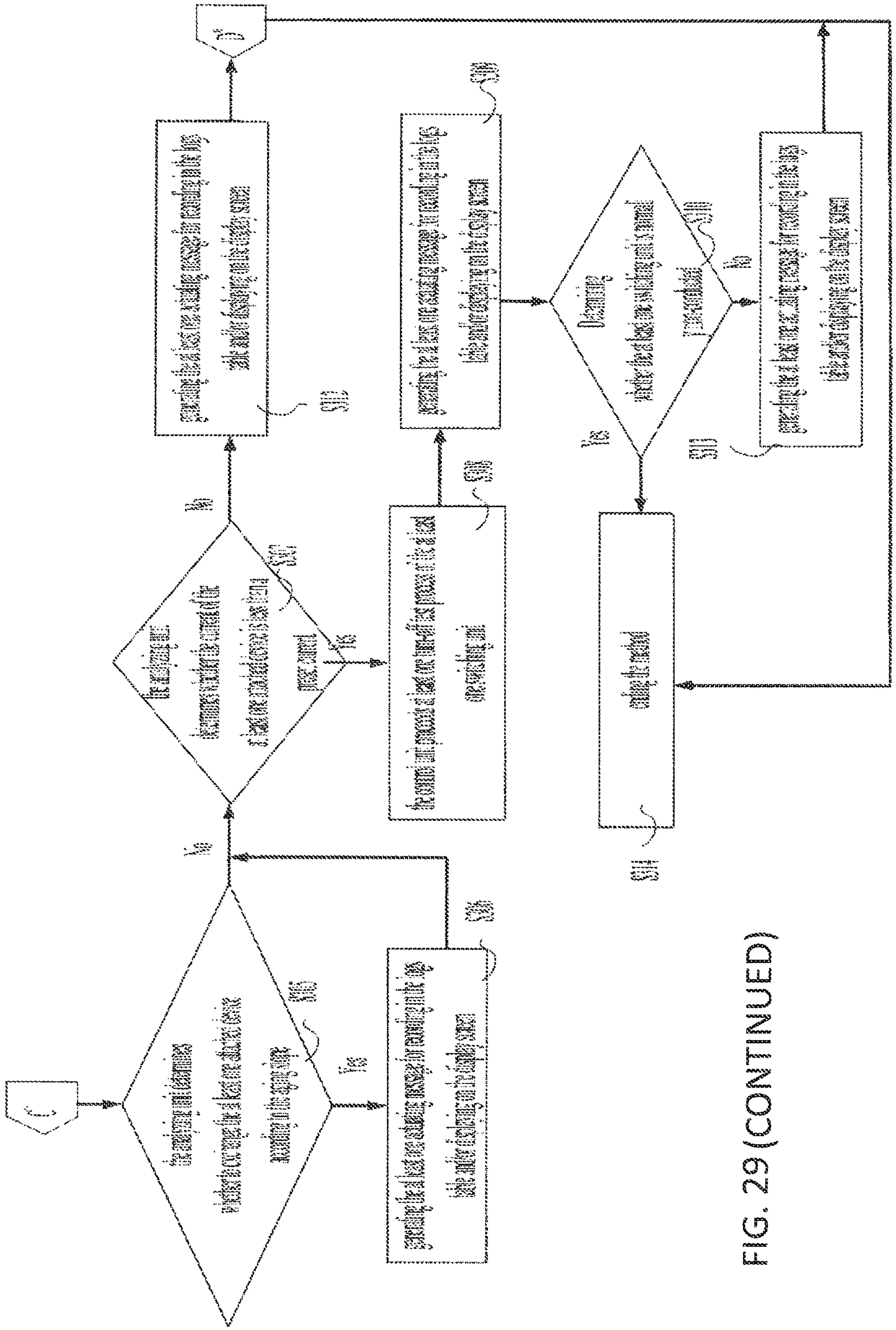

FIG. 29 is a detailed flow diagram of a self-detection method of the massage bathing maintenance system according to one embodiment of the present invention, First, step S301, the control unit 2100 proceeds at least one turn-on test process of the at least one switching unit. Then, step S302, recording in the logs table 1011 and/or displaying on the display screen 1110. Then, step S303, determining whether the at least one switching unit is normally conducted. In step S303, if no, then step S311, generating the at least one actuating message for recording in the logs table 1011 and/or displaying on the display screen 1110. Then, step S314, ending the method. In step S303, if yes, then proceeding to step S304, the analyzing unit 5510 calculates an aging slope of a current-time curve of the at least one attached device 3000 according to the logs table 1011. Then, step S305, the analyzing unit 5510 determines whether to exchange the at least one attached device 3000 according to the aging slope by the analyzing unit 5510. In step S305, if yes, then proceeding to step S306, generating the at least one actuating message for recording in the logs table 1011 and/or displaying on the display screen 1110, Then, step S307, the analyzing unit 5510 determines whether the current of the at least one attached device 3000 is less than a preset current. In step 3305, if no, then proceeding to step S307. In step S307, if no, then proceeding to step S312, generating the at least one actuating message for recording in the logs table 1011 and/or displaying on the display screen 1110. Then, step 3314, ending the method. In step S307, if yes, then proceeding to step S308, the control unit 2100 proceeds at least one turn-off test process of the at least one switching unit. Then, step S309, generating the at least one detecting message for recording in the logs table 1011 and/or displaying on the display screen 1110. Then, step S310, determining whether the at least one switching unit is normally non-conducted. In step S310, if no, then proceeding to step S313, generating the at least one detecting message for recording in the logs table 1011 and/or displaying on the display screen 1110. Then, step S314, ending the method, in step S310, if yes, then proceeding to step S314, ending the method.

Figure 30:
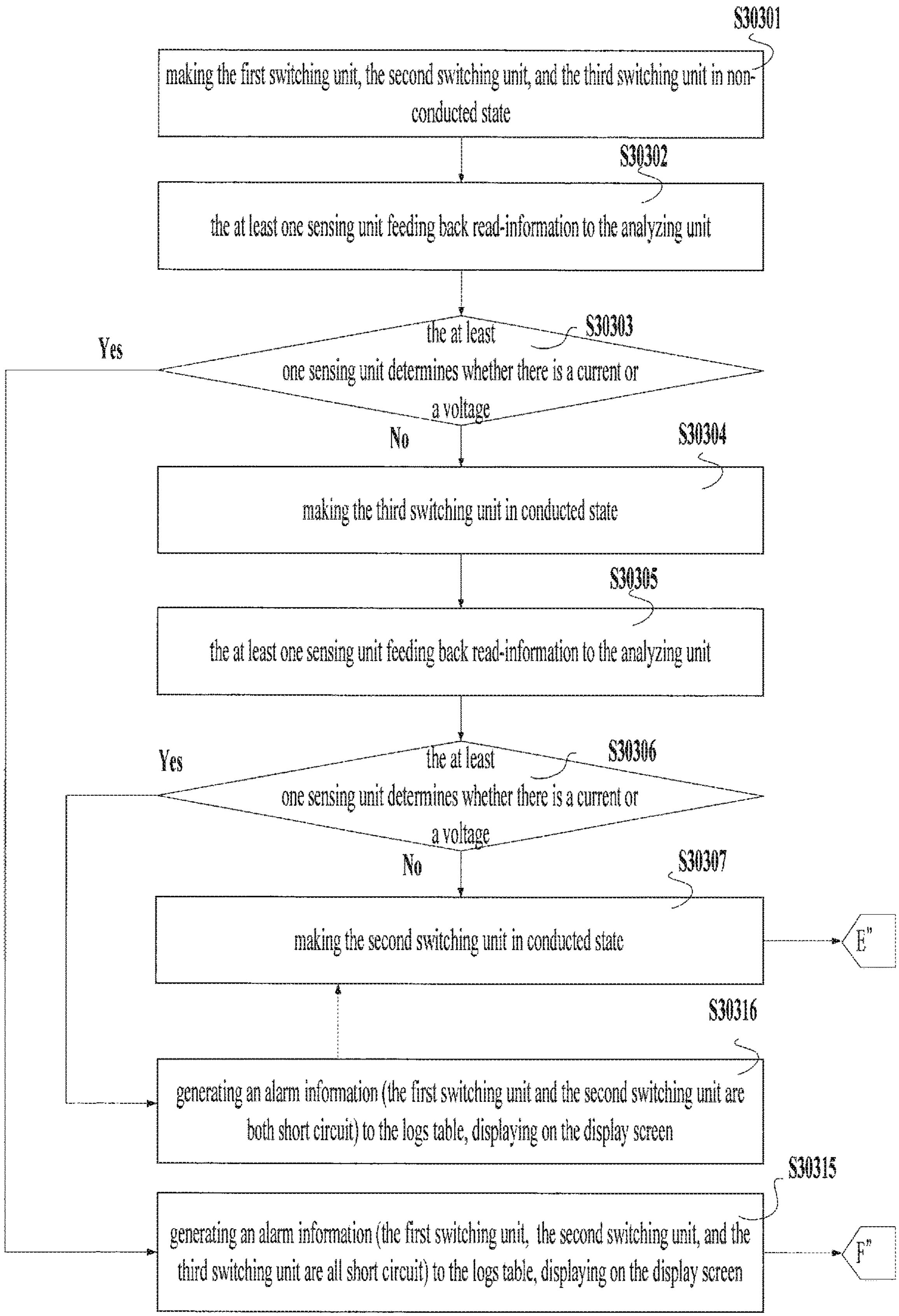
FIG. 30 is a flow diagram of a first detailed detection method of the step S303 of FIG. 29.
Figure 30:
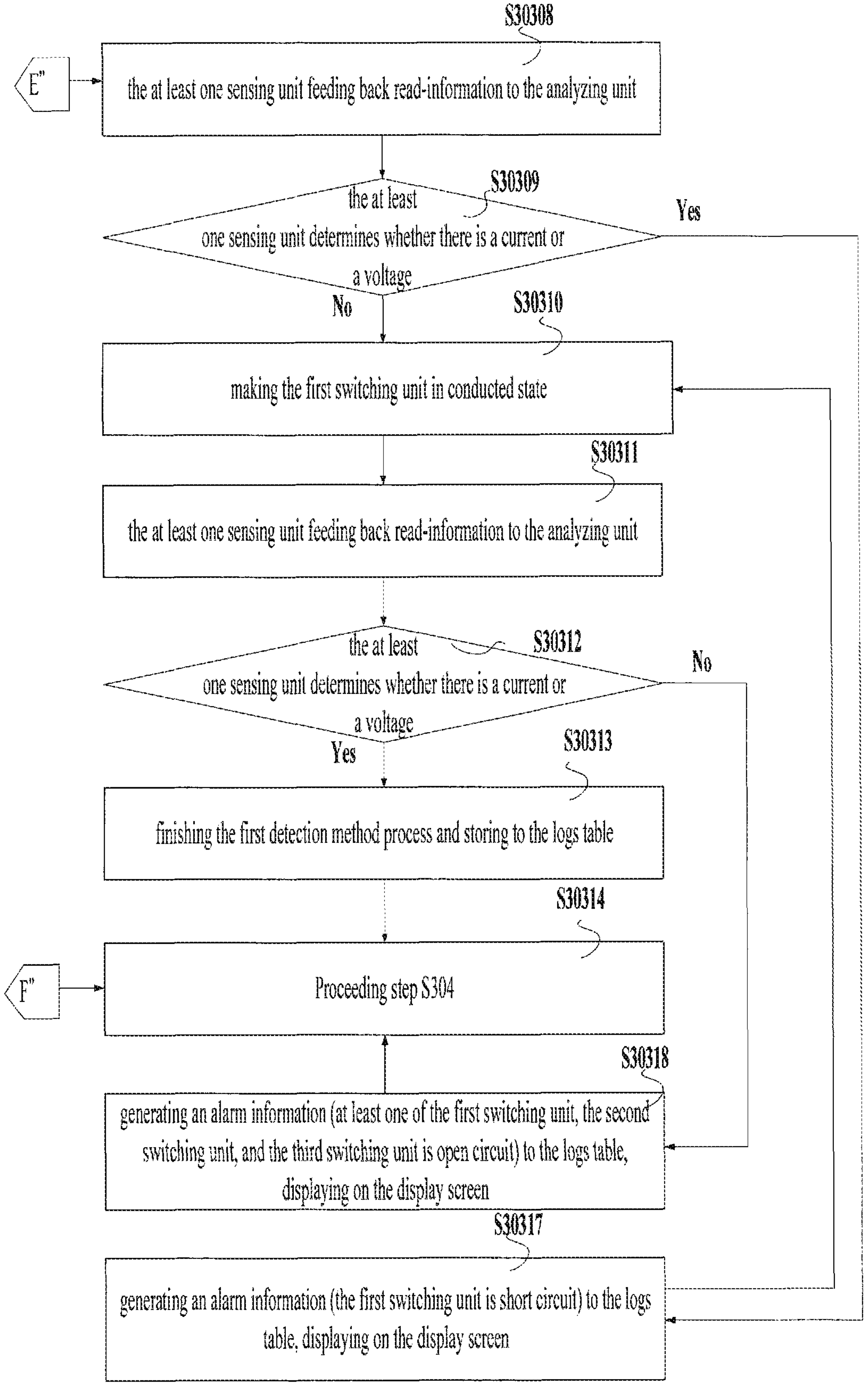

FIG. 30 is a flow diagram of a first detailed detection method of the step S303 of FIG. 29. First, step S30301, making the first switching unit 2010, the second switching unit 2020, and the third switching unit 2030 in non-conducted state. Then, step S30302, the at least one sensing unit 2220 feeding back read-information to the analyzing unit 5510. Then, step S30303, the at least one sensing unit 2220 determines whether there is a current or a voltage. In step S30303, if yes, then proceeding to step S30315, generating an alarm information (the first switching unit 2010, the second switching unit 2020, and the third switching unit 2030 are all short circuit) to the logs table 1011, displaying on the display screen 1110. Then, step S30314, proceeding to step S304. In step S30303, if no, then proceeding to step S30304, making the third switching unit 2030 in conducted state. Then, step S30305, the at least one sensing unit 2220 feeding back read-information to the analyzing unit 5510. Then, step S30306, the at least one sensing unit 2220 determines whether there is a current or a voltage. In step S30306, if yes, then proceeding to step S30316, generating an alarm information (the first switching unit 2010 and the second switching unit 2020 are both short circuit) to the logs table 1011, displaying on the display screen 1110. Then, step S30307, making the second switching unit 2020 in conducted state. In step S30306, if no, then proceeding to step S30307, making the second switching unit 2020 in conducted state. Then, step S30308, the at least one sensing unit 2220 feeding back read-information to the analyzing unit 5510. Then, step S30309, the at least one sensing unit 2220 determines whether there is a current or a voltage. In step S30309, if yes, then proceeding to step S30317, generating an alarm information (the first switching unit 2010 is short circuit) to the logs table 1011, displaying on the display screen 1110. Then, step S30310, making the first switching unit 2010 in conducted state. Then, step S30311, the at least one sensing unit 2220 feeding back read-information to the analyzing unit 5510. Then, step S30312, the at least one sensing unit 2220 determines whether there is a current or a voltage. In step S30312, if no, then proceeding to step S30313, generating an alarm information (at least one of the first switching unit 2010, the second switching unit 2020, and the third switching unit 2030 is an open circuit) to the logs table 1011, displaying on the display screen 1110. Then, step S30314, proceeding to step S304. In step S30312, if yes, then proceeding to step S30313, finishing the first detection method process and storing to the logs table 1011. Then, step S30314, proceeding to step S304.

Figure 31:
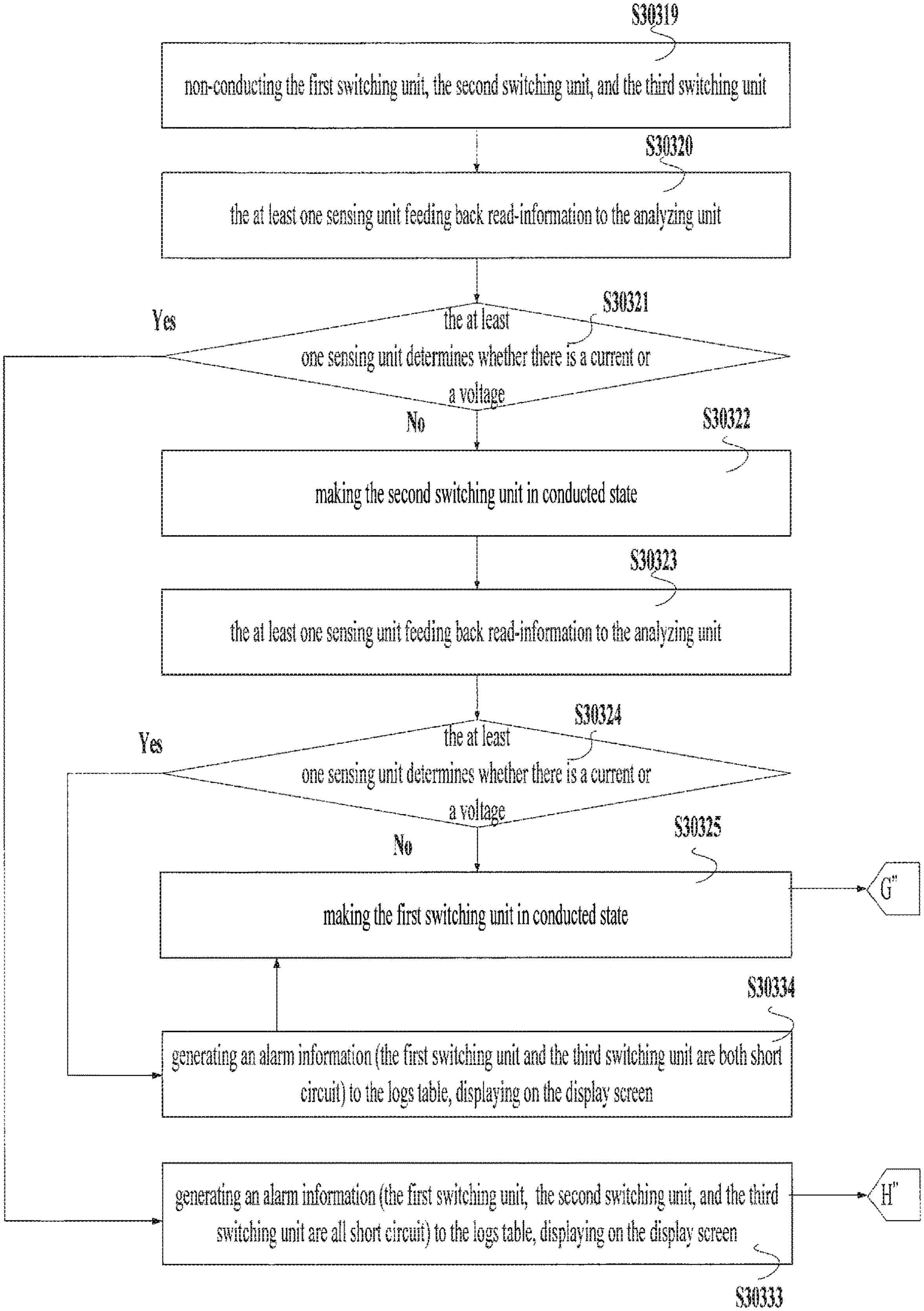
FIG. 31 is a flow diagram of a second detailed detection method of the step 3303 of FIG. 29.
Figure 31:
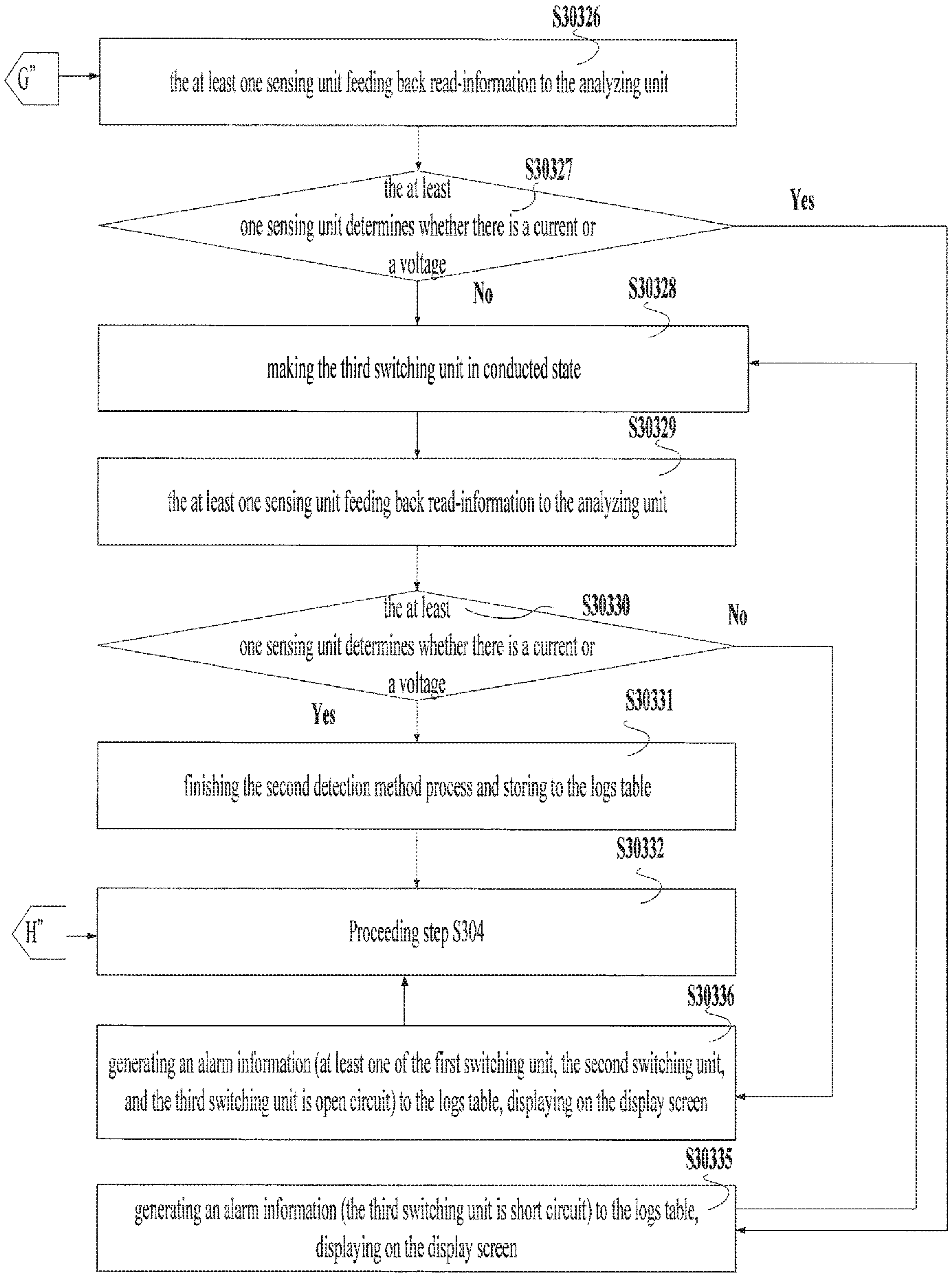

FIG. 31 is a flow diagram of a second detailed detection method of the step 3303 of FIG. 29. First, step S30319, making the first switching unit 2010, the second switching unit 2020, and the third switching unit 2030 in non-conducted state. Then, step S30320, the at least one sensing unit 2220 feeding back read-information to the analyzing unit 5510. Then, step S30321, the at least one sensing unit 2220 determines whether there is a current or a voltage. In step S30321, if yes, then proceeding to step S30333, generating an alarm information (the first switching unit 2010, the second switching unit 2020, and the third switching unit 2030 are all short circuit) to the logs table 1011, displaying on the display screen 1110. Then, step S30332, proceeding to step S304. In step S30321, if no, then step S30322, making the second switching unit 2020 in conducted state. Then, step S30323, the at least one sensing unit 2220 feeding back read-information to the analyzing unit 5510. Then, step S30324, the at least one sensing unit 2220 determines whether there is a current or a voltage. In step S30324, if yes, then step S30334, generating an alarm information (the first switching unit 2010 and the third switching unit 2030 are both short circuit) to the logs table 1011, displaying on the display screen 1110. Then, step S30325, making the first switching unit 2010 in conducted state. In step S30324, if no, then proceeding to step S30325, making the first switching unit 2010 in conducted state. Then, step S30326, the at least one sensing unit 2220 feeding back read-information to the analyzing unit 5510. Then, step S30327, the at least one sensing unit 2220 determines whether there is a current or a voltage. In step S30327, if yes, then proceeding to step S30335, generating an alarm information (the third switching unit 2030 is short circuit) to the logs table 1011, displaying on the display screen 1110. Then, step S30328, making the third switching unit 2030 in conducted state. Then, step S30329, the at least one sensing unit 2220 feeding back read-information to the analyzing unit 5510, Then, step S30330, the at least one sensing unit 2220 determines whether there is a current or a voltage. In step S30330, if no, then proceeding to step S30336, generating an alarm information (at least one of the first switching unit 2010, the second switching unit 2020, and the third switching unit 2030 is an open circuit) to the logs table 1011, displaying on the display screen 1110. Then, step S30332, proceeding to step S304. In step S30330, if yes, then proceeding to step S30331, finishing the second detection method process and storing to the logs table 1011. Then, step S30332, proceeding to step S304.

Figure 32:
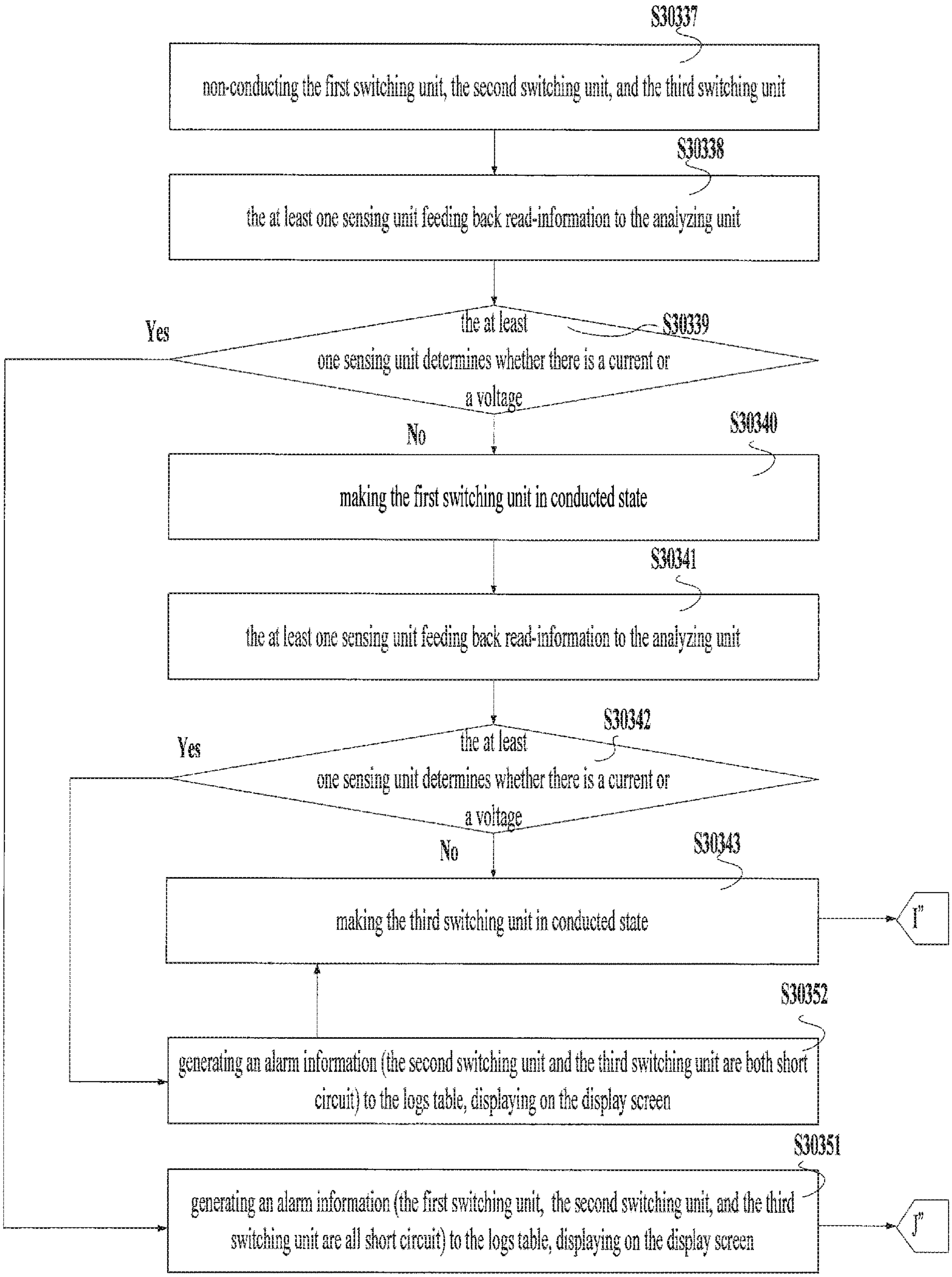
FIG. 32 is a flow diagram of a third detailed detection method of the step S303 of FIG. 29.
Figure 32:
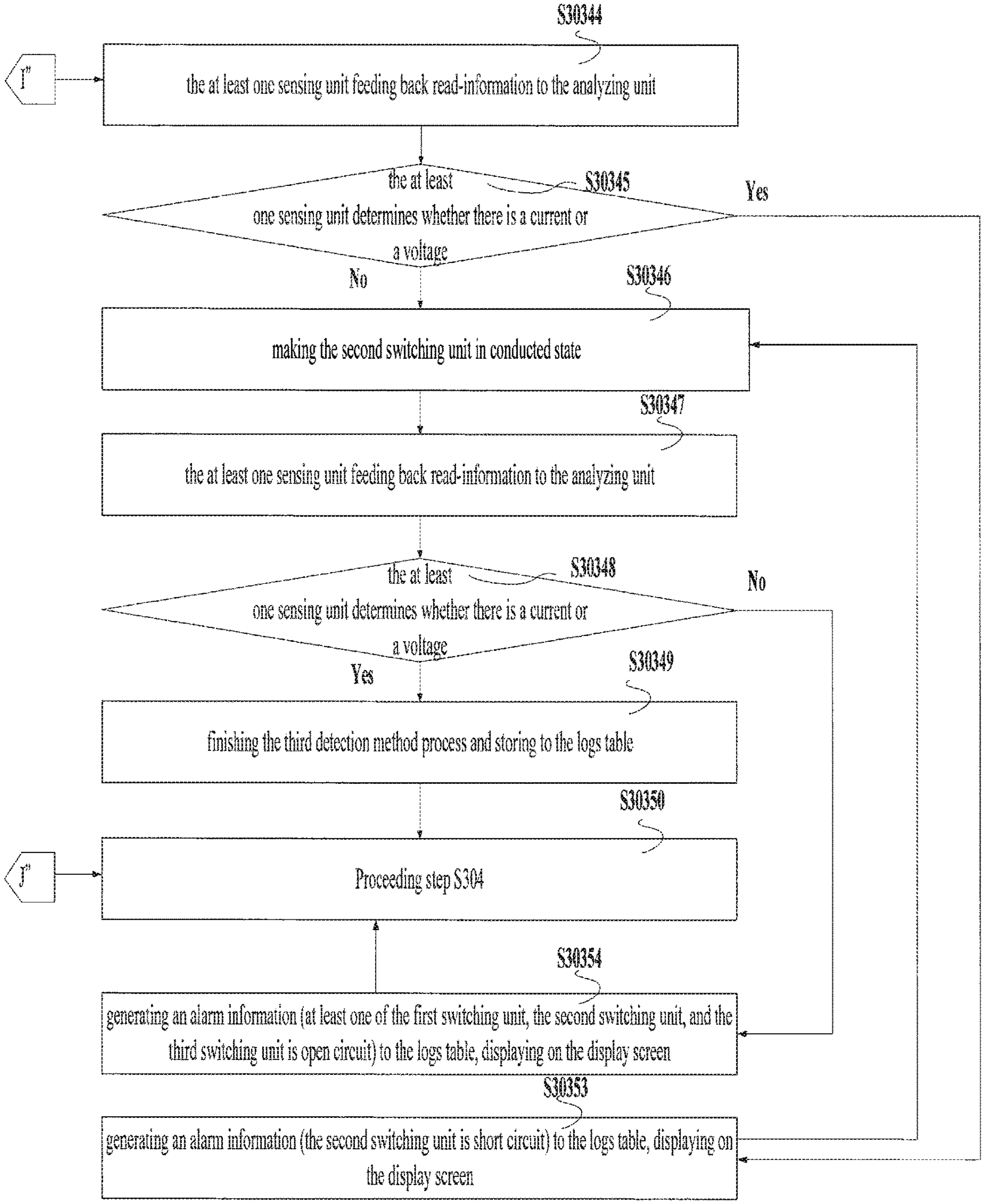

FIG. 32 is a flow diagram of a third detailed detection method of the step S303 of FIG. 29. First, step S30337, making the first switching unit 2010, the second switching unit 2020, and the third switching unit 2030 in non-conducted state. Then, step S30338, the at least one sensing unit 2220 feeding back read-information to the analyzing unit 5510. Then, step S30339, the at least one sensing unit 2220 determines whether there is a current or a voltage. In step S30339, if yes, then step S30351, generating an alarm information (the first switching unit 2010, the second switching unit 2020, and the third switching unit 2030 are all short circuit) to the logs table 1011, displaying on the display screen 1110. Then, step S30350, proceeding to step S304. In step S30339, if no, then proceeding to step S30340, making the first switching unit 2010 in conducted state. Then, step S30341, the at least one sensing unit 2220 feeding back read-information to the analyzing unit 5510. Then, step 330342, the at least one sensing unit 2220 determines whether there is a current or a voltage. In step S30342, if yes, then step S30352, generating an alarm information (the second switching unit 2020 and the third switching unit 2030 are both short circuits) to the logs table 1011, displaying on the display screen 1110. Then, step S30343, making the third switching unit 2030 in conducted state. In step S30342, if no, then step S30343, making the third switching unit 2030 in conducted state. Then, step S30344, the at least one sensing unit 2220 feeding back read-information to the analyzing unit 5510. Then, step S30345, the at least one sensing unit 2220 determines whether there is a current or a voltage. In step S30345, if yes, then proceeding to step S30353, generating an alarm information (the second switching unit 2020 is short circuit) to the logs table 1011, displaying on the display screen 1110. Then, step S30346, making the second switching unit 2020 in conducted state. In step S30345, if no, then proceeding to step S30346, making the second switching unit 2020 in conducted state. Then, step S30347, the at least one sensing unit 2220 feeding back read-information to the analyzing unit 5510. Then, step S30348, the at least one sensing unit 2220 determines whether there is a current or a voltage. In step S30348, if no, then proceeding to step S30354, generating an alarm information (at least one of the first switching unit 2010, the second switching unit 2020, and the third switching unit 2030 is an open circuit) and sends the information to the logs table 1011, displaying on the display screen 1110. Then, step S30350, proceeding to step S304. In step 330348, if yes, then proceeding to step S30349, finishing the third detection method process and storing to the logs table 1011. Then, step S30350, proceeding to step S304.

One of the three detection processes of step S303 is chosen at every power on, the chosen detection process will be proceeded, and the chosen detection process is different from the previous two detection methods.

Figure 33:
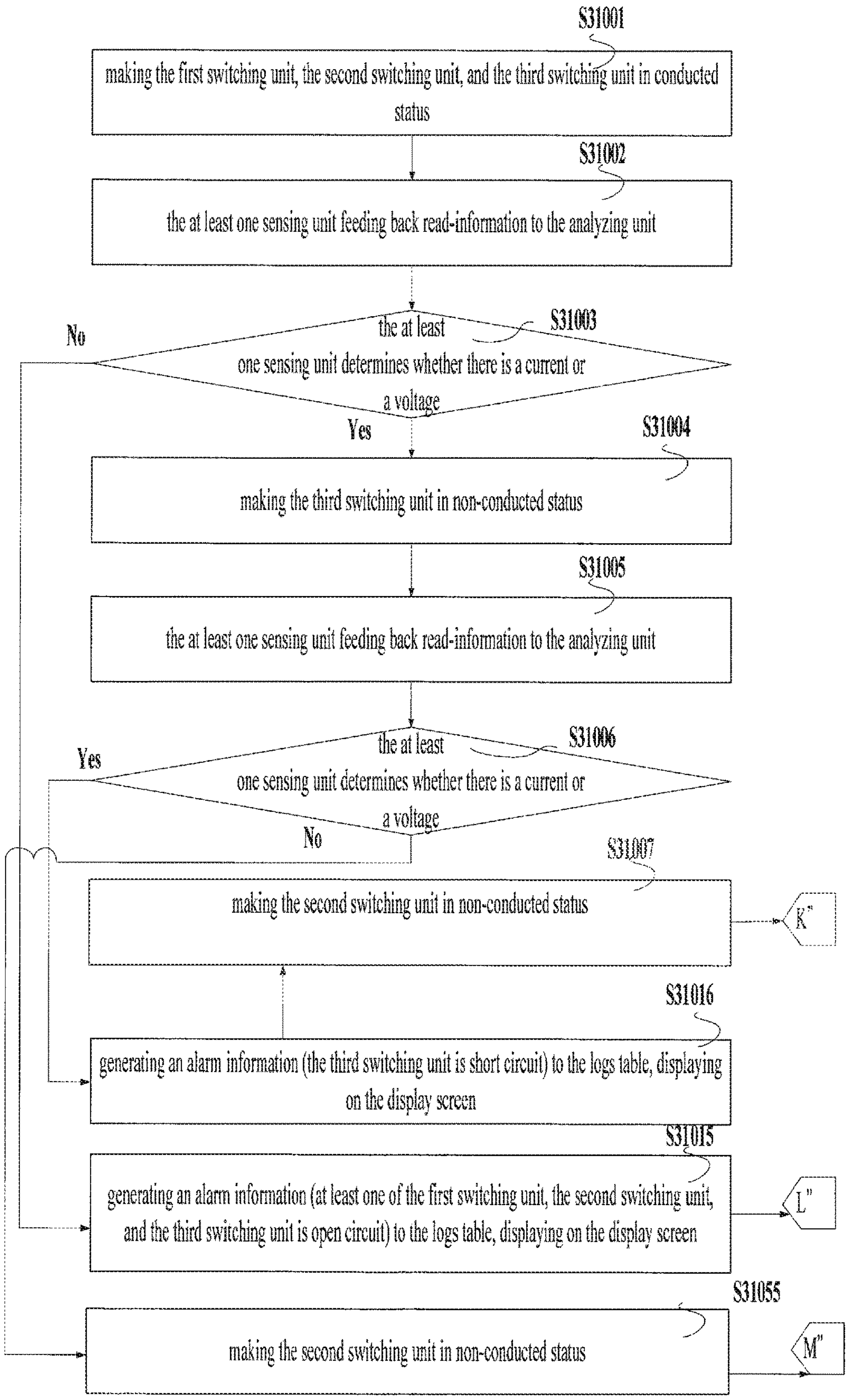
FIG. 33 is a flow diagram of a first detailed detection method of the step S310 of FIG. 29.
Figure 33:
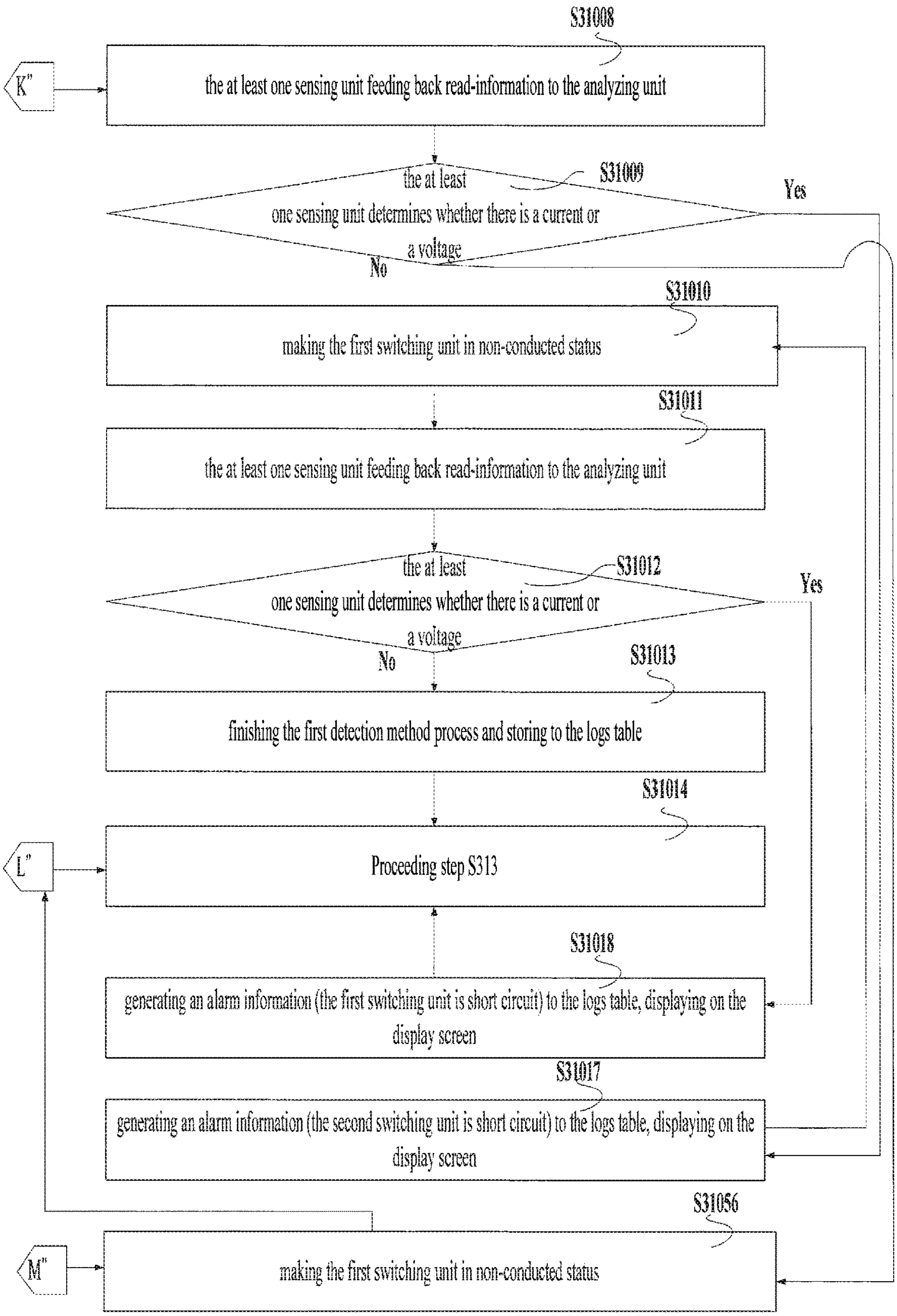

FIG. 33 is a flow diagram of a first detailed detection method of the step S310 of FIG. 29, First, step S31001, making the first switching unit 2010, the second switching unit 2020, and the third switching unit 2030 in conducted state. Then, step S31002, the at least one sensing unit 2220 feeding back read-information to the analyzing unit 5510. Then, step S31003, the at least one sensing unit 2220 determines whether there is a current or a voltage. In step S31003, if no, then step S31015, generating an alarm information (at least one of the first switching unit 2010, the second switching unit 2020, and the third switching unit 2030 is an open circuit) to the logs table 1011, displaying on the display screen 1110. Then, step S31014, proceeding step S313. In step S31003, if yes, then proceeding to step S31004, making the third switching unit 2030 in non-conducted state. Then, step S31005, the at least one sensing unit 2220 feeding back read-information to the analyzing unit 5510. Then, step S31006, the at least one sensing unit 2220 determines whether there is a current or a voltage. In step S31006, if no, then proceeding to step S31055, making the second switching unit 2020 in non-conducted state. Then, step 331056, making the first switching unit 2010 in non-conducted state. Then, step S31014, proceeding to step S313. In step S31006, if yes, then proceeding to step S31016, generating an alarm information (the third switching unit 2030 is short circuit) to the logs table 1011, displaying on the display screen 1110. Then, step S31007, making the second switching unit 2020 in non-conducted state. Then, step S31008, the at least one sensing unit 2220 feeding back read-information to the analyzing unit 5510. Then, step S31009, the at least one sensing unit 2220 determines whether there is a current or a voltage. In step S31009, if no, then proceeding to step S31056, making the first switching unit 2010 in non-conducted state. In step S31009, if yes, then proceeding to step S31017, generating an alarm information (the second switching unit 2020 is short circuit) to the logs table 1011, displaying on the display screen 1110. Then, step S31010, making the first switching unit 2010 in non-conducted state. Then, step S31011, the at least one sensing unit 2220 feeding back read-information to the analyzing unit 5510. Then, step S31012, the at least one sensing unit 2220 determines whether there is a current or a voltage. In step S31012, if yes, then proceeding to step S31018, generating an alarm information (the first switching unit 2010 is short circuit) to the logs table 1011, displaying on the display screen 1110. Then, step S31014, proceeding to step S313. In step S31012, if no, then proceeding to step S31013, finishing the first detection method process and storing to the logs table 1011. Then, step S31014, proceeding to step S313.

Figure 34:
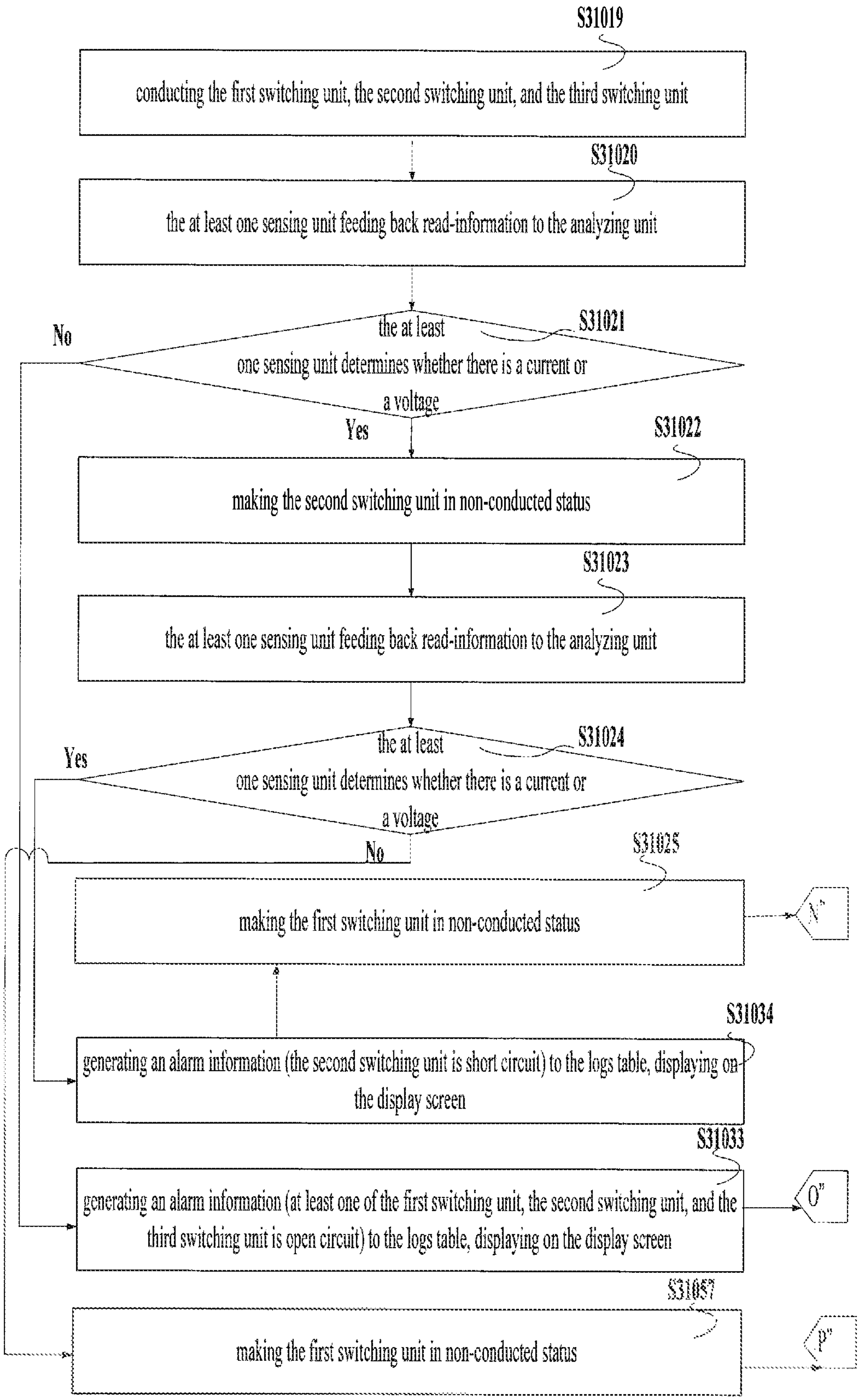
FIG. 34 is a flow diagram of a second detailed detection method of the step S310 of FIG. 29.
Figure 34:
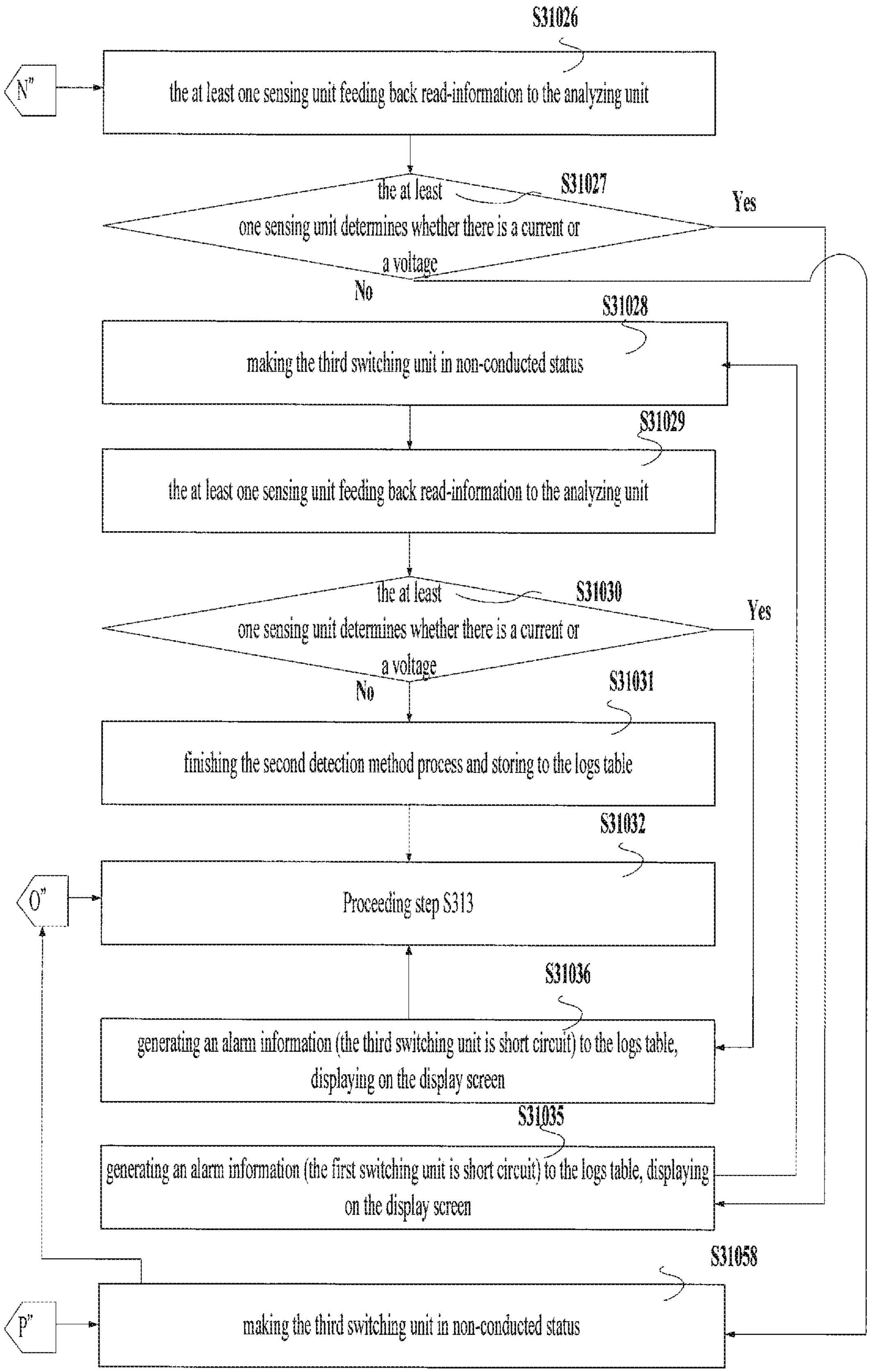

FIG. 34 is a flow diagram of a second detailed detection method of the step S310 of FIG. 29. First, step S31019, making the first switching unit 2010, the second switching unit 2020, and the third switching unit 2030 in conducted state. Then, step S31020, the at least one sensing unit 2220 feeding back read-information to the analyzing unit 5510. Then, step S31021, the at least one sensing unit 2220 determines whether there is a current or a voltage. In step S31021, if no, then proceeding to step S31033, generating an alarm information (at least one of the first switching unit 2010, the second switching unit 2020, and the third switching unit 2030 is an open circuit) to the logs table 1011, displaying on the display screen 1110. Then, step S31032, proceeding to step S313. In step S31021, if yes, then proceeding to step S31022, making the second switching unit 2020 in non-conducted state. Then, step S31023, the at least one sensing unit 2220 feeding back read-information to the analyzing unit 5510. Then, step S31024, the at least one sensing unit 2220 determines whether there is a current or a voltage. In step S31024, if no, then step S31057, making the first switching unit 2010 in non-conducted state. Then, step S31058, making the third switching unit 2030 in non-conducted state. Then, step S31032, proceeding to step S313. In step S31024, if yes, then proceeding to step S31034, generating an alarm information (the second switching unit 2020 is short circuit) to the logs table 1011, displaying on the display screen 1110. Then, step S31025, making the first switching unit 2010 in non-conducted state. Then, step S31026, the at least one sensing unit 2220 feeding back read-information to the analyzing unit 5510. Then, step S31027, the at least one sensing unit 2220 determines whether there is a current or a voltage. In S31027, if no, then processing step S31058, making the third switching unit 2030 in non-conducted state. In step S31027, if yes, then proceeding to step S31035, generating an alarm information (the first switching unit 2010 is short circuit) to the logs table 1011, displaying on the display screen 1110. Then, step S31028, making the third switching unit 2030 in non-conducted state. Then, step S31029, the at least one sensing unit 2220 feeding back read-information to the analyzing unit 5510. Then, step S31030, the at least one sensing unit 2220 determines whether there is a current or a voltage. In step S31030, if yes, then proceeding to step S31030, generating an alarm information (the second switching unit 2030 is short circuit) to the logs table 1011, displaying on the display screen 1110. Then, step S31032, proceeding step S313. In step S31030, if no, then proceeding to step S31031, finishing the second detection method process and storing to the logs table 1011. Then, step S31032, proceeding to step S313.

Figure 35:
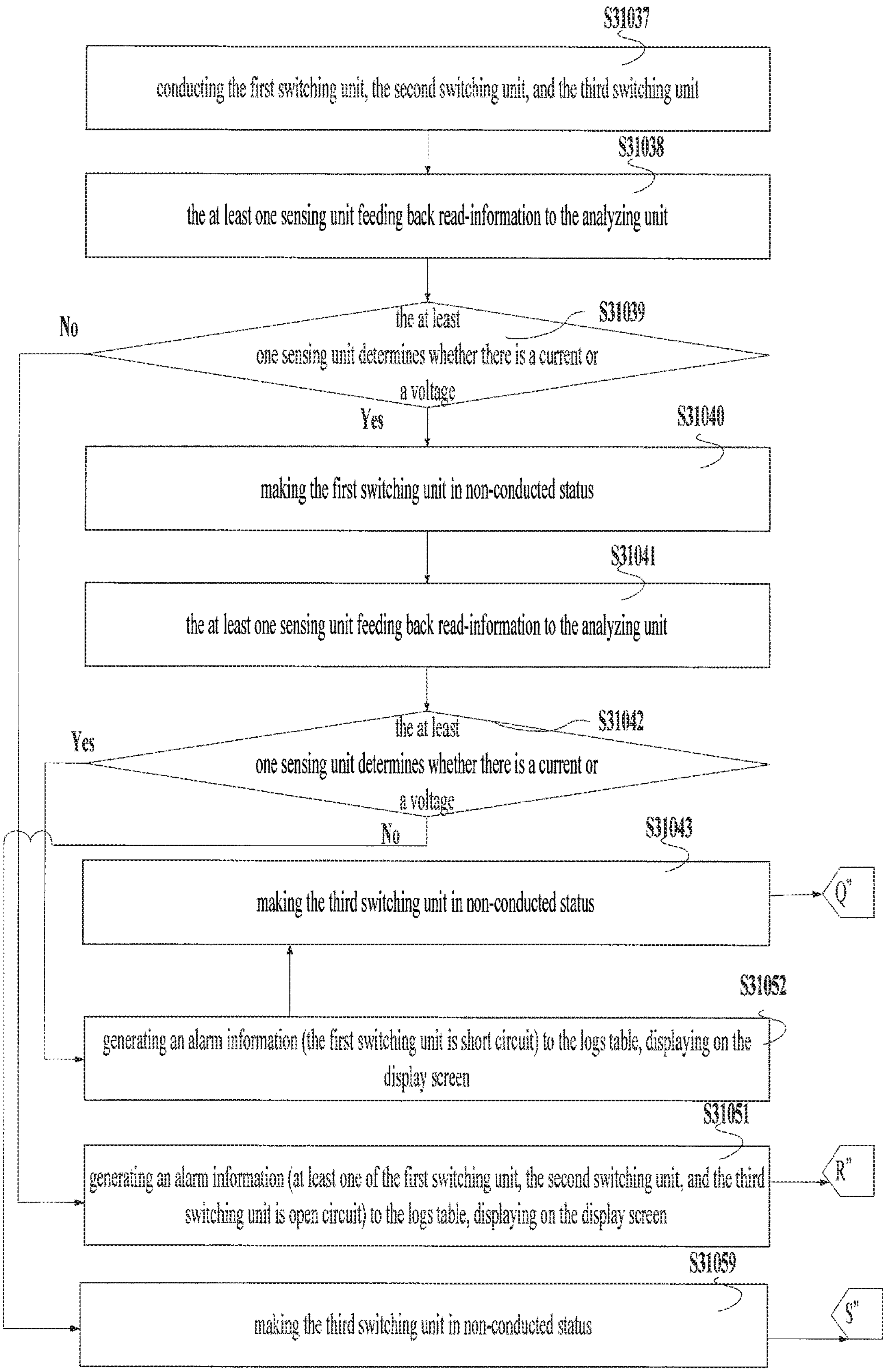
FIG. 35 is a flow diagram of a third detailed detection method of the step S310 of FIG. 29.
Figure 35:
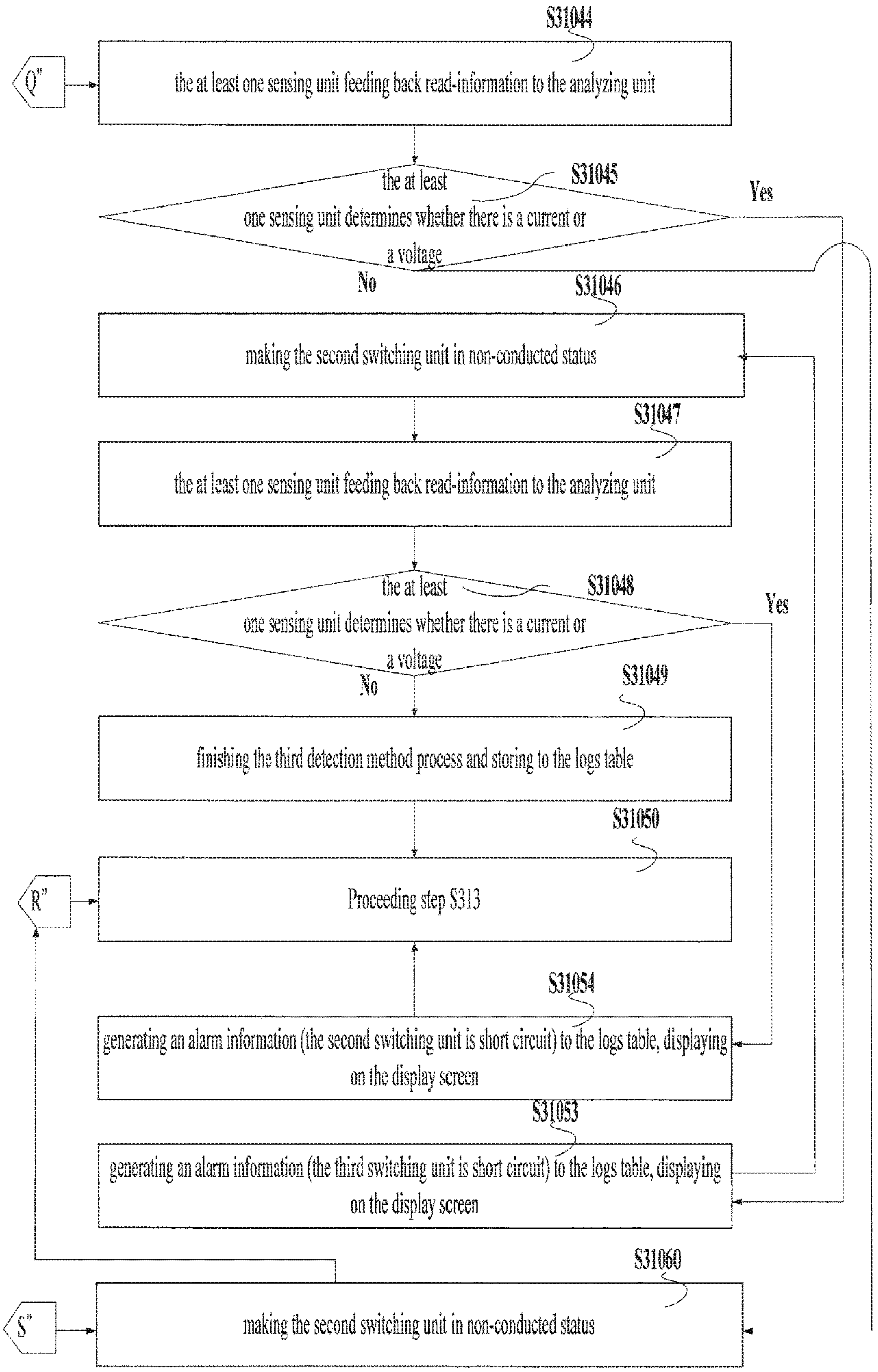

FIG. 35 is a flow diagram of a third detailed detection method of the step S310 of FIG. 29. First, step S31037, making the first switching unit 2010, the second switching unit 2020, and the third switching unit 2030 in conducted state. Then, step S31038, the at least one sensing unit 2220 feeding back read-information to the analyzing unit 5510. Then, step S31039, the at least one sensing unit 2220 determines whether there is a current or a voltage. In step S31039, if no, then step S31051, generating an alarm information (at least one of the first switching unit 2010, the second switching unit 2020, and the third switching unit 2030 is an open circuit) to the logs table 1011, displaying on the display screen 1110. Then, step S31050, proceeding step S313. In step S31039, if yes, then proceeding to step S31040, making the first switching unit 2010 in non-conducted state. Then, step S31041, the at least one sensing unit 2220 feeding back read-information to the analyzing unit 5510. Then, step S31042, the at least one sensing unit 2220 determines whether there is a current or a voltage. In step S31042, if no, then step S31059, making the third switching unit 2030 in non-conducted state. Then, step S31060, making the second switching unit 2030 in non-conducted state. Then, step S31050, proceeding to step S313. In step S31042, if yes, then step S31052, generating an alarm information (the first switching unit 2010 is short circuit) to the logs table 1011, displaying on the display screen 1110. Then, step S31043, making the third switching unit 2030 in non-conducted state. Then, step S31044, the at least one sensing unit 2220 feeding back read-information to the analyzing unit 5510. Then, step S31045, the at least one sensing unit 2220 determines whether there is a current or a voltage. In step S31045, if no, then step S31060, making the second switching unit 2020 in non-conducted state. Then, step S31050, proceeding to step S313. In step S31045, if yes, then step S31053, generating an alarm information (the third switching unit 2030 is short circuit) to the logs table 1011, displaying on the display screen 1110. Then, step S31046, making the second switching unit 2020 in non-conducted state. Then, step 331047, the at least one sensing unit 2220 feeding back read-information to the analyzing unit 5510. Then, step S31045, the at least one sensing unit 2220 determines whether there is a current or a voltage. In step S31048, if yes, then proceeding to step S31054, generating an alarm information (the second switching unit 2020 is short circuit) to the logs table 1011, displaying on the display screen 1110. Then, step S31050, proceeding to step S313. In step S31048, if no, then proceeding to step S31049, finishing the third detection method process and storing to the logs table 1011. Then, step S31050, proceeding to step S313.

One of the three detection process of step S310 is chosen at every power off, the chosen detection process will be proceeded, and the chosen detection process is different from the previous two detection methods.

Figure 36:
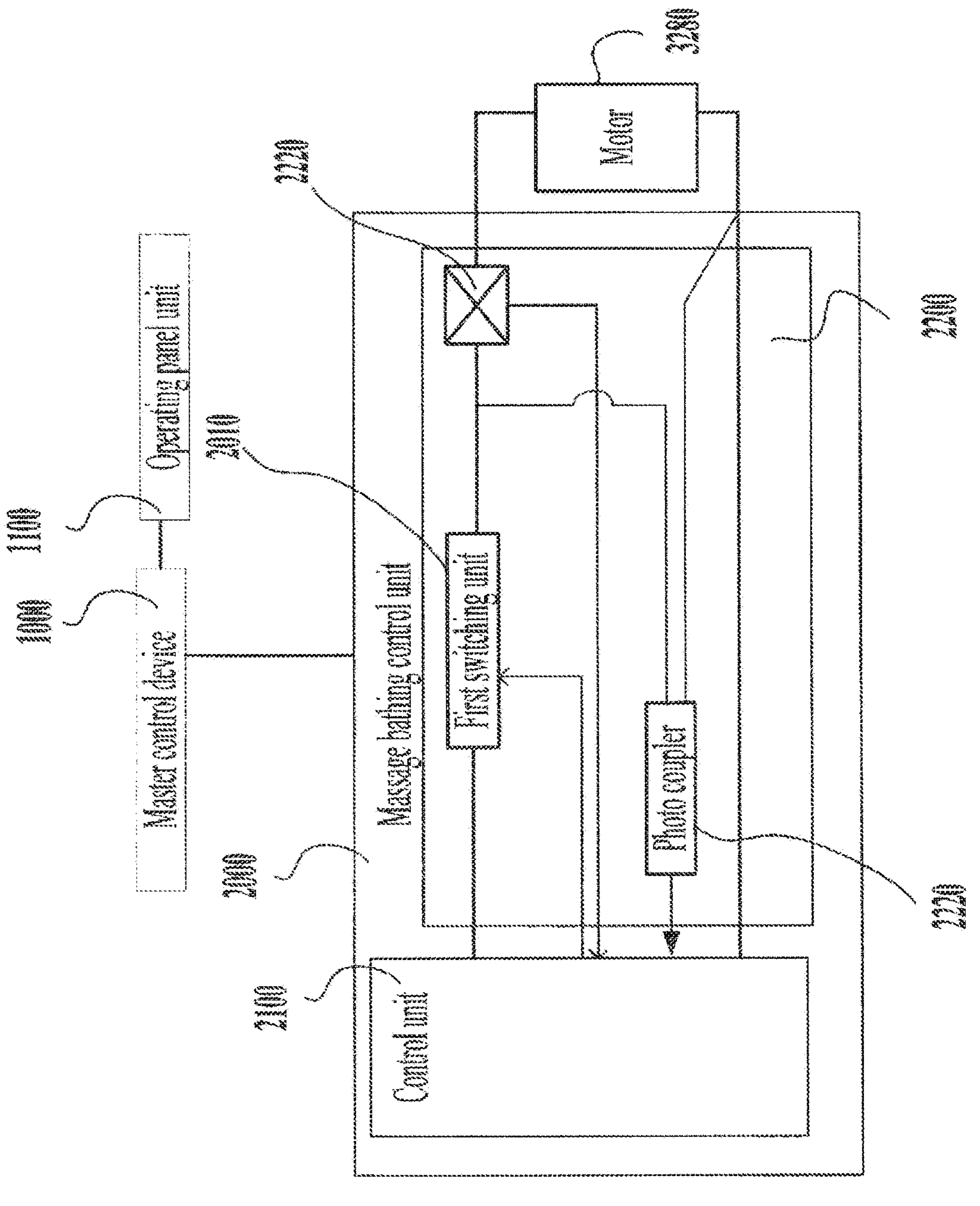
FIG. 36 is a third composing view of the massage bathing control unit of a massage bathing maintenance system of the present invention.
Figure 37:
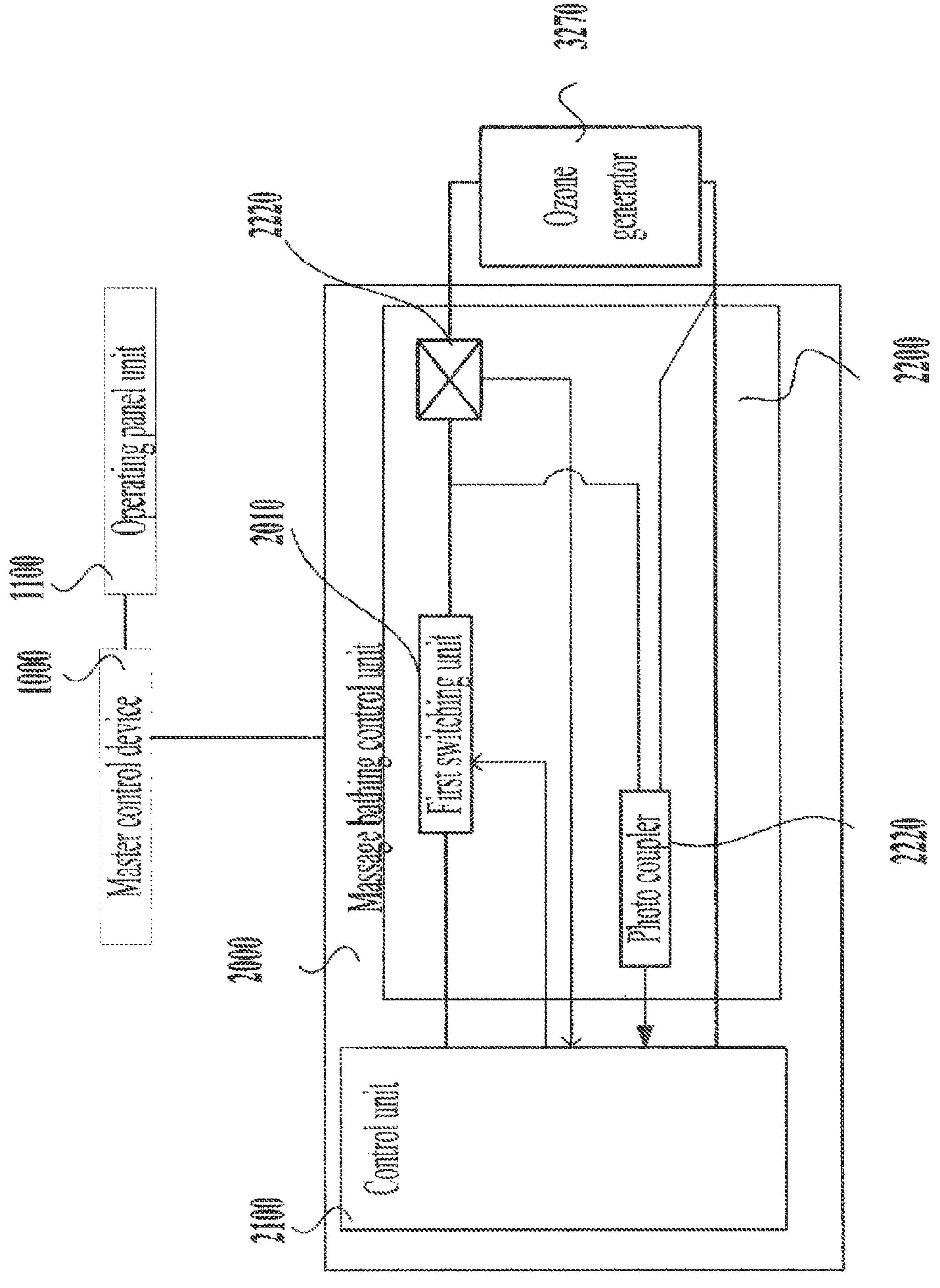
FIG. 37 is a fourth composing view of the massage bathing control unit of a massage bathing maintenance system of the present invention.
Figure 38:
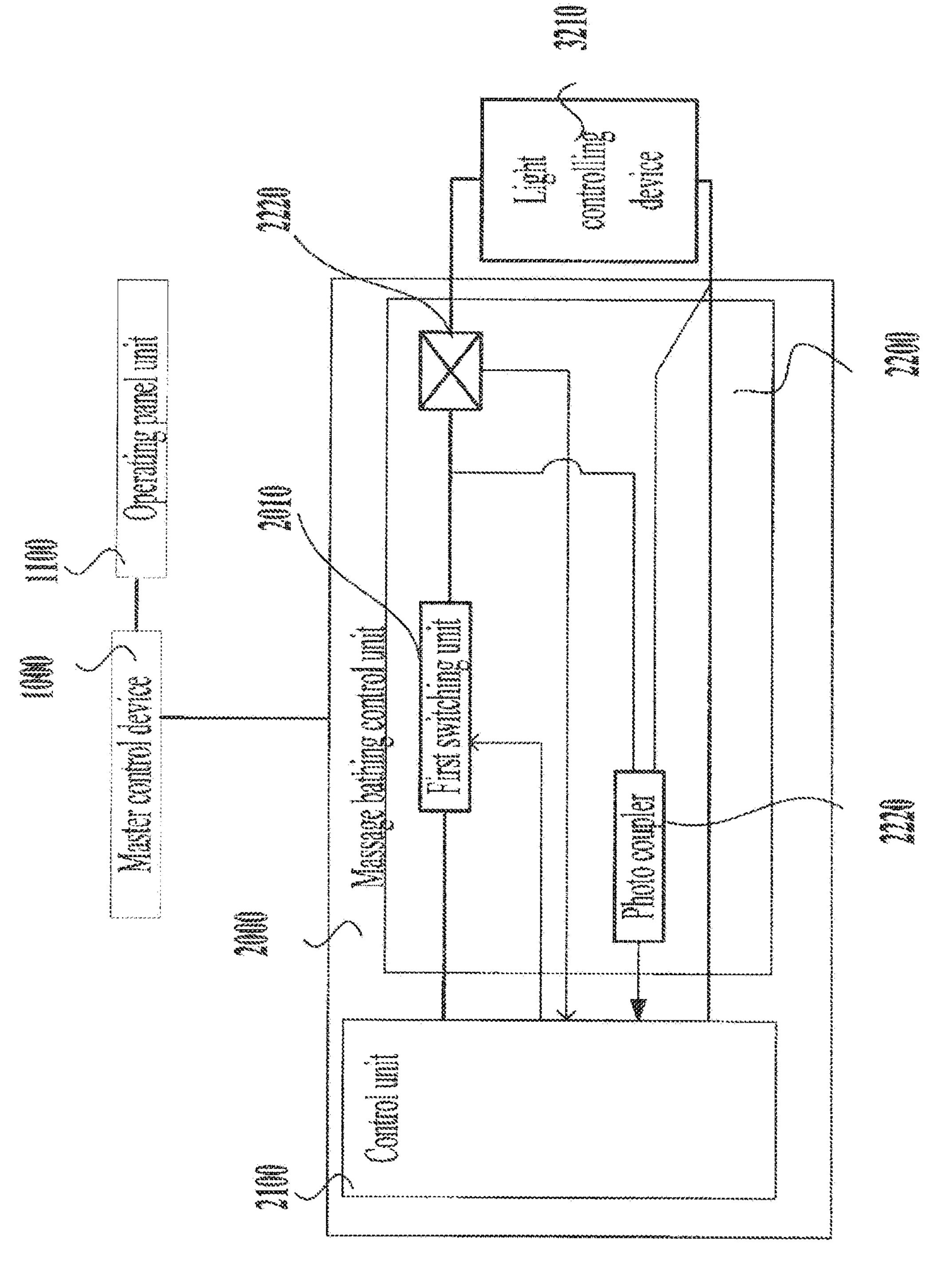
FIG. 38 is a fifth composing view of the massage bathing control unit of a massage bathing maintenance system of the present invention.
Figure 39:
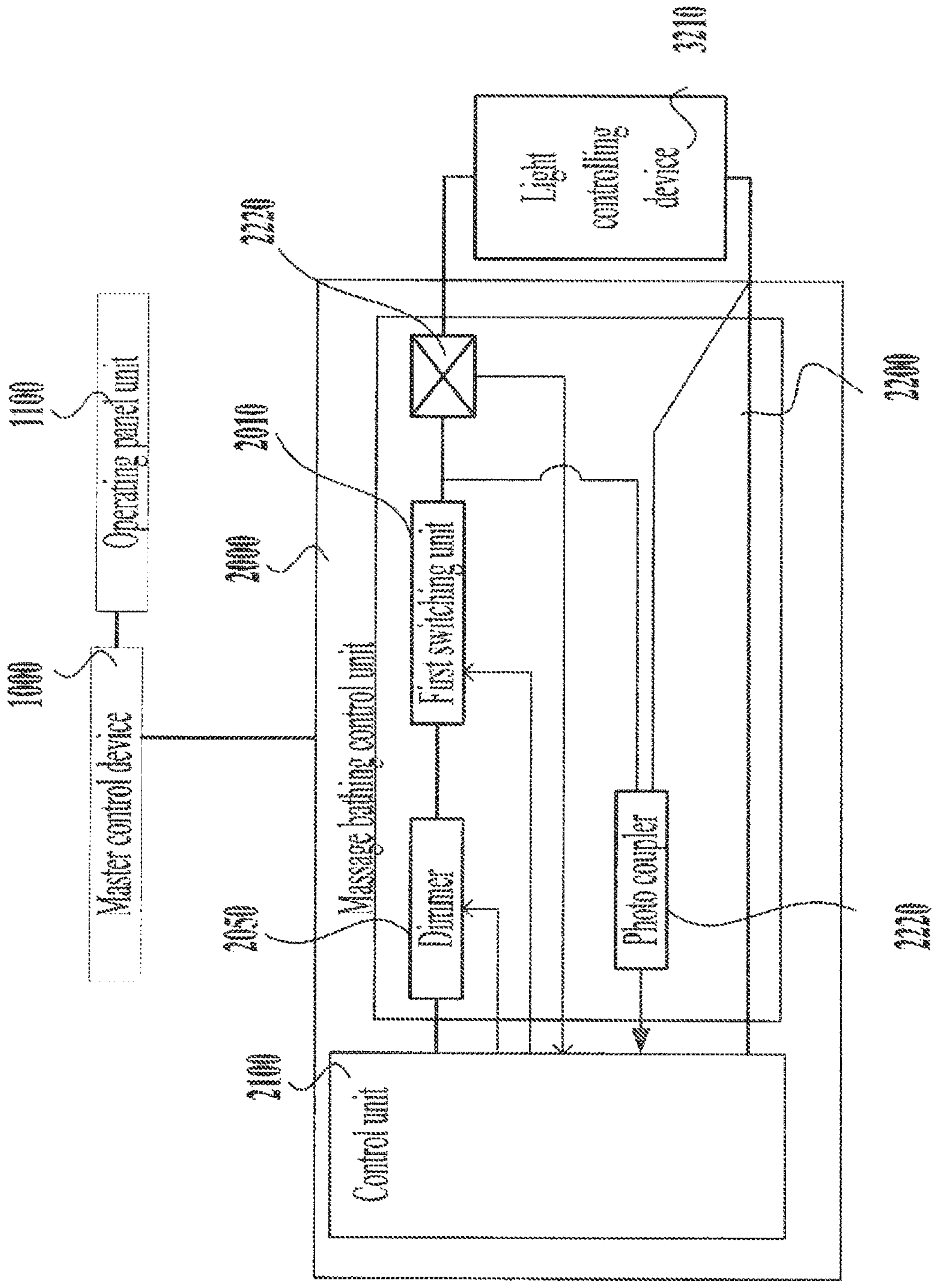
FIG. 39 is a sixth composing view of the massage bathing control unit of a massage bathing maintenance system of the present invention.

With reference of FIGS. 36-39. FIG. 36 is a third composite view of the massage bathing control unit of a massage bathing maintenance system of the present invention. FIG. 37 is a fourth composite view of the massage bathing control unit of a massage bathing maintenance system of the present invention. FIG. 38 is a fifth composite view of the massage bathing control unit of a massage bathing maintenance system of the present invention. FIG. 39 is a sixth composite view of the massage bathing control unit of a massage bathing maintenance system of the present invention. The difference between the four embodiments is: the four embodiments are respectively connecting to the motor 3280, the Ozone generator 3270, and the light controlling device 3210 (with/without a dimmer 2050). The difference between the four embodiments and the second composing is: each of the embodiments of FIGS. 36-39 has only the first switching unit 2010. The control unit 2100 connects to the first switching unit 2010, the first switching unit 2010 connects to a first terminal of the first sensing unit 2220, a second terminal of the first sensing unit 2220 connects to the control unit 2100, a third terminal of the first sensing unit 2220 connects to a first terminal of the second attached device 3200 (motor 3280, Ozone generator 3270, and light controlling device 3210), a second terminal of the second attached device 3200 connects to the control unit 2100. A first terminal of the photo coupler 2220 (as the second sensing unit) connects to the control unit 2100, a second terminal of the photo coupler 2220 connects to the first terminal of the first sensing unit 2220, a third terminal of the photo coupler 2220 connects to the second terminal of the second attached device 3200.

Figure 40:
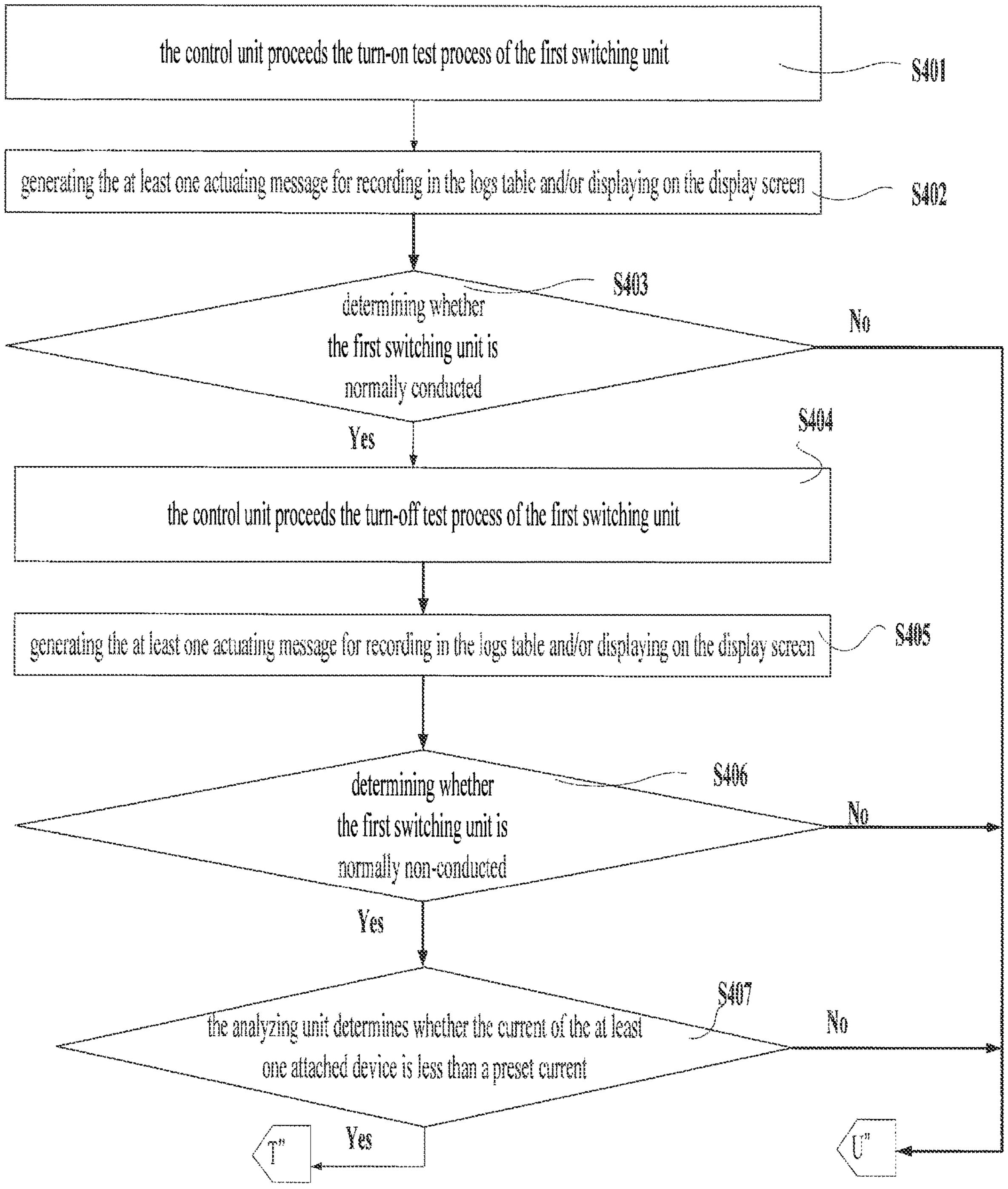
FIG. 40 is a detailed flow diagram of a self-detection method of the massage bathing maintenance system of the present invention while using one switching unit.
Figure 40:
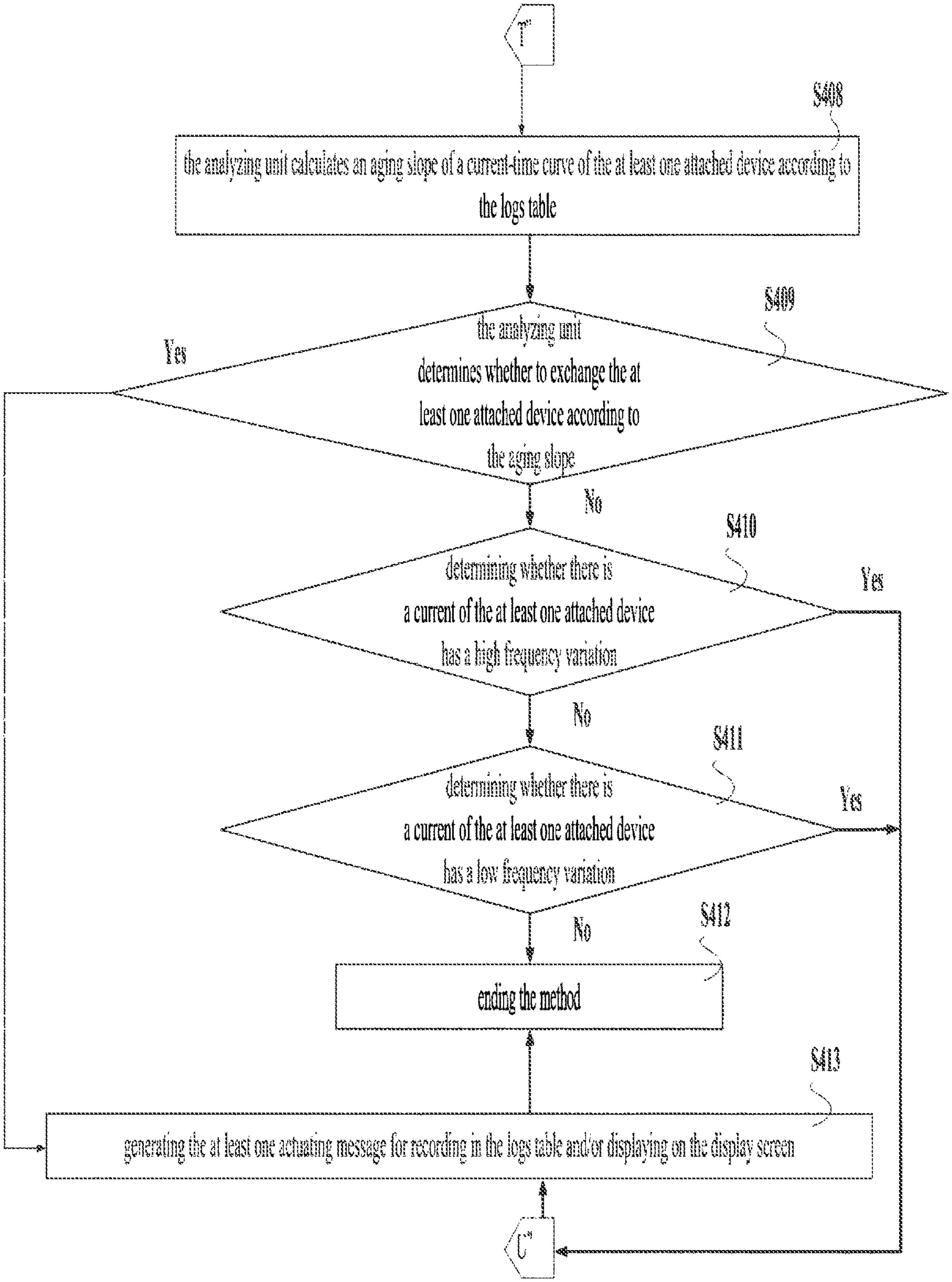

FIG. 40 is a detailed flow diagram of a self-detection method of the massage bathing maintenance system of the present invention while using one switching unit. First, step S401, the control unit 2100 proceeds the turn-on test process of the first switching unit. Then, step 3402, generating the at least one actuating message for recording in the logs table 1011 and/or displaying on the display screen 1110. Then, step S403, determining whether the first switching unit is normally conducted. In step S403, if no, then proceeding to step 3413, generating the at least one actuating message for recording in the logs table 1011 and/or displaying on the display screen 1110. Then, step S412, ending the method. In step S403, if yes, then proceeding to step 3404, the control unit 2100 proceeds the turn-off test process of the first switching unit. Then, step 3405, generating the at least one actuating message for recording in the logs table 1011 and/or displaying on the display screen 1110. Then, step S406, determining whether the first switching unit is normally non-conducted. In step S406, if no, then proceeding to step S413, generating the at least one actuating message for recording in the logs table 1011 and/or displaying on the display screen 1110. Then, step S412, ending the method. In step S406, if yes, then proceeding to step S407, the analyzing unit 5510 determines whether the current of the at least one attached device 3000 is less than a preset current. In step S407, if no, then proceeding to step S413, generating the at least one actuating message for recording in the logs table 1011 and/or displaying on the display screen 1110. Then, step S412, ending the method. In step S407, if yes, then proceeding to step S408, the analyzing unit 5510 calculates an aging slope of a current-time curve of the at least one attached device 3000 according to the logs table 1011. Then, step S409, the analyzing unit 5510 determines whether to exchange the at least one attached device 3000 according to the aging slope by the analyzing unit 5510. In step S409, if yes, then proceeding to step S413, generating the at least one actuating message for recording in the logs table 1011 and/or displaying on the display screen 1110. Then, step S412, ending the method. In step S409, if no, then proceeding to step S410, determining whether there is a current of the at least one attached device has a high frequency variation. In step S410, if yes, then proceeding to step S413, generating the at least one actuating message for recording in the logs table 1011 and/or displaying on the display screen 1110. Then, step S412, ending the method. In step S410, if no, then proceeding to step S411, determining whether there is a current of the at least one attached device has a low frequency variation. In step S411, if yes, then proceeding to step S413, generating the at least one actuating message for recording in the logs table 1011 and/or displaying on the display screen 1110. Then, step S412, ending the method. In step S411, if no, then proceeding to step S412, ending the method.

The massage bathing maintenance system and method of the same is able to quickly derive the operational situation, then giving quick and suitable maintenance.

As described above, although the present invention has been described with the preferred embodiments thereof, those skilled in the art will appreciate that various modifications, additions, and substitutions are possible without departing from the scope and the spirit of the invention. Accordingly, the scope of the present invention is intended to be defined only by reference to the claims.

What is claimed is:

1. A massage bathing maintenance system, which is applied for a massage bathing equipment, comprising:

at least one attached device attached to the massage bathing equipment and provided for actuating to the massage bathing equipment;

at least one slave control device, which comprises a control unit and a detection-feedback device, wherein the control unit is configured to generate and transmit at least one actuating message according to at least one actuating-status of the at least one attached device;

a master control device configured to control the at least one slave control device, through a master-slave connection therebetween, for receiving the at least one actuating message, and the master control device comprising a log-collecting unit configured to record the at least one actuating message of the at least one slave control device into a logs table; and an analyzing unit configured to analyze the at least one actuating message of the logs table to determine the actuating-status of the at least one attached device;

wherein the control unit controls the detection-feedback device in a manner that detects the at least one attached device, generates the at least one actuating message including a result of the detection, and transmits the at least one actuating message to the master control device, wherein the actuating message contains a physical value or a chemical value, wherein the master control device generates at least one controlling message to the at least one slave control device according to at least one preset remote detecting and maintaining management process, and the master control device requests the control unit of the at least one slave control device to proceed a detection so that the at least one slave control device generates the at least one actuating message including the detection result, wherein the detection-feedback device comprises at least one switch unit and at least one sensing unit, the at least one switching unit is controlled by the control unit to turn on or off a power source supplied to the at least one attached device, the at least one sensing unit detects the physical value between the at least one switch unit and the at least one attached device, and transmits the physical value to the control unit, and the control unit treats the physical value as the detection result to generate the at least one actuating message according to the detection result and provides the at least one actuating message to the master control device; or the detection-feedback device comprises at least one switch unit and at least one sensing unit, the at least one switching unit is controlled by the control unit to turn on or off a power source supplied to the at least one attached device, the at least one sensing unit detects the physical value of the at least one attached device, and transmits the physical value to the control unit, and the control unit treats the physical value as the detection result to generate the at least one actuating message according to the detection result and provides the at least one actuating message to the master control device; or the detection-feedback device comprises at least one switch unit and at least one sensing unit, the at least one switching unit is controlled by the control unit to turn on or off a power source supplied to the at least one attached device, the at least one sensing unit detects the physical value between the power source supplied to the at least one attached device and the at least one attach device, and transmits the physical value to the control unit, and the control unit treats the physical value as the detection result to generate the at least one actuating message according to the detection result and provides the at least one actuating message to the master control device.

2. The massage bathing maintenance system according to claim 1, wherein the at least one slave control device is a massage bathing control unit.

3. The massage bathing maintenance system according to claim 2, wherein the at least one attached device comprises one or a combination of several of a blower, a motor, an air valve, a sensor, a pump, an ozone generator, a light controlling device and a heater.

4. The massage bathing maintenance system according to claim 1, wherein the master control device requests the at least one slave control device to feed back the at least one actuating message.

5. The massage bathing maintenance system according to claim 1, wherein the at least one attached device is disposed inside the at least one slave control device.

6. The massage bathing maintenance system according to claim 1, wherein the system further comprises at least one wireless communication transceiver and a cloud server, the cloud server comprises at least one cloud database, a certificate managing unit, an device-managing unit, an instant-message transceiving management unit, and a remote detecting and maintaining management unit, the remote detecting and maintaining management unit comprises the analyzing unit, the at least one cloud database is configured to store a corresponding serial number of the massage bathing equipment, and the at least one wireless communication transceiver is configured to be connected with the cloud server, for transmitting the logs table via the master control device to the at least one cloud database of the cloud server, and for storing the logs table in the at least one cloud database of the cloud server.

7. The massage bathing maintenance system according to claim 6, wherein the remote detecting and maintaining management unit of the cloud server sends a request via the master control device to the at least one slave control device, for transmitting the at least one actuating message back to the cloud server.

8. The massage bathing maintenance system according to claim 6, wherein the cloud server makes the remote detecting and maintaining management unit to proceed the at least one preset remote detecting and maintaining management process according to a determined result, made by the analyzing unit, with respect to the at least one actuating message of the logs table.

9. The massage bathing maintenance system according to claim 6, wherein the master control device further requests the control unit of the at least one slave control device to proceed warm reboots.

10. The massage bathing maintenance system according to claim 8, wherein the master control device proceeds at least one maintenance operation according to the at least one preset remote detecting and maintaining management process, and after the at least one maintenance operation is proceeded, the master control device requests the control unit of the at least one slave control device to proceed the detection so that the at least one slave control device generates the at least one actuating message including the detection result, wherein the at least one maintaining operation comprises one or a combination of several of wrong setup corrections, cold reboots, source code reinstallations and software version updates.

11. The massage bathing maintenance system according to claim 10, wherein the master control device proceeds the at least one maintaining operation via a maintain interface.

12. The massage bathing maintenance system according to claim 11, wherein the maintain interface is one or both of JTAG and RESET.

13. The massage bathing maintenance system according to one of claims 1, wherein the at least one switch unit is a relay, the physical value is a current value or a logical determined value.

14. The massage bathing maintenance system according to claim 1, wherein the detection-feedback device further comprises a temperature-measurement-offset confirming device, which is electrically connected with the control unit and is configured to detect a temperature status of a temperature meter to be the detection result, and the control unit generates the at least one actuating message according to the detection result and transmits the at least one actuating message to the master control device.

15. The massage bathing maintenance system according to claim 14, wherein the temperature-measurement-offset confirming device comprises a temperature sensor and a voltage detection unit, both of which detect data for determining status of the temperature sensor.

16. The massage bathing maintenance system according to claim 1, wherein the analyzing unit looks up a built-in table according to the at least one actuating message, to determine the at least one actuating-status of the at least one attached device and/or aging situation of the at least one attached device.

* * * * *